US009951341B2

(12) United States Patent
Horvath et al.

(10) Patent No.: US 9,951,341 B2
(45) Date of Patent: Apr. 24, 2018

(54) *LACTOCOCCUS* CRISPR-CAS SEQUENCES

(75) Inventors: Philippe Horvath, Chatellerault (FR);
Dennis Romero, Oregon, WI (US);
Anne M. Millen, Madison, WI (US)

(73) Assignee: DUPONT NUTRITION BIOSCIENCES APS (DK)

( * ) Notice: Subject to any disclaimer, the term of this patent is extended or adjusted under 35 U.S.C. 154(b) by 467 days.

(21) Appl. No.: 13/880,391

(22) PCT Filed: Oct. 20, 2011

(86) PCT No.: PCT/US2011/057102
§ 371 (c)(1),
(2), (4) Date: Jul. 3, 2013

(87) PCT Pub. No.: WO2012/054726
PCT Pub. Date: Apr. 26, 2012

(65) Prior Publication Data
US 2013/0288251 A1  Oct. 31, 2013

Related U.S. Application Data

(60) Provisional application No. 61/394,976, filed on Oct. 20, 2010, provisional application No. 61/405,317, filed on Oct. 21, 2010.

(51) Int. Cl.
*C12N 15/74* (2006.01)
*C07K 14/195* (2006.01)

(52) U.S. Cl.
CPC .......... *C12N 15/746* (2013.01); *C07K 14/195* (2013.01); *C12N 15/74* (2013.01)

(58) Field of Classification Search
None
See application file for complete search history.

(56) References Cited

U.S. PATENT DOCUMENTS 5,474,796 A * 12/1995 Brennan .................... 427/2.13

FOREIGN PATENT DOCUMENTS

| WO | 2006/073445 A2 | 7/2006 |
| WO | 2007/136815 A2 | 11/2007 |
| WO | 2008/108989 A2 | 9/2008 |
| WO | 2010/054154 A2 | 5/2010 |

OTHER PUBLICATIONS

NEB catalog (1998/1999), pp. 121, 284.*
Database EMBL [Online]; Oct. 7, 1996 (Oct. 7, 1996), "L.lactis abiH gene", XP002667677, retrieved from EBI accession No. EMPRO:X97651, Database accession No. X97651.
Prevots Fabien et al: "Cloning and sequencing of the novel abortive infection gene abiH of *Lactococcus lactis* ssp. *Lactis biovar*. diacetylactis S94", FEMS Microbiology Letters, Blackwell Publishing, Amsterdam, NL, vol. 142, No. 2-3, Jan. 1, 1996 (Jan. 1, 1996), pp. 295-299, XP002543326, ISSN: 0378-1097, DOI: 10.1111/J.1574-6968.1996.TB08446.X.
Database EMBL [Online]; Dec. 20, 2004 (Dec. 20, 2004), "Sequence 122 from Patent W02004106367.", XP002667678, retrieved from EBI accession No. EMBL:CQ969547, Database accession No. CQ969547.
Database EMBL [Online]; Oct. 8, 2008 (Oct. 8, 2008), "CATNI1705.rev CATN Nectria haematococca mpVI Sporulation (PDB) 77-13-4 Mycelia 24 hour culture Nectria haematococca mpVl cDNA clone CATNI1705 3', mRNA sequence.", XP002667679, retrieved from EBI accession No. EMBL: GE217086; Database accession No. GE217086.
Database Geneseq [Online]; Feb. 13, 2002 (Feb. 13, 2002), "DNA encoding novel human diagnostic protein #2179.", XP002667680, retrieved from EBI accession No. GSN:AAS66375; Database accession No. AAS66375
Horvath P et al: "Comparative analysis of CRISPR loci in lactic acid bacteria genomes", International Journal of Food Microbiology, Elsevier Science Publishers, Amsterdam, NL, vol. 131, No. I, Apr. 30, 2009 (Apr. 30, 2009), pp. 62-70, XP026052665, ISSN: 0168-1605, DOI: 10.1016/J. IJFOODMICRO.2008.05.030 [retrieved on Jul. 16, 2008].
P. Horvath et al: "CRISPR/Cas, the Immune System of Bacteria and Archaea" , SCIENCE, vo 1. 327, No. 5962, Jan. 7, 2010 (Jan. 7, 2010), pp. 167-170, XP55016971, ISSN: 0036-8075, DOI: 10.1126/science.1179555.
Fedor V. Kargi Nov et al: "The CRISPR System: Small RNA-Guided Defense in Bacteria and Archaea" , Molecular Cell, vo 1. 37, No. I, Jan. 1, 2010 (Jan. 1, 2010), pp. 7-19, XP55016972 , ISSN: 1097-2765, DOI: 10.1016/j.molce1.2009.12.033.
Grissa I et al: "CRISPRFinder: a web tool to identify clustered regularly interspaced short palindromic repeats", Nucleic Acids Research, Oxford University Press, Surrey, GB, vol. 35, May 31, 2007 (May 31, 2007), pp. W52-W57, XP002490217, ISSN: 0305-1048, DOI: 10.1093/NAR/GKM360.
International Search Report and Written Opinion of the International Searching Authority for PCT/US2011/057102.
Millen, AM et al., "Mobile CRISPR/Cas-Mediated Bacteriophage Resistance in *Lactococcus lactis* ," PLOS ONE, Dec. 2012, vol. 7, No. 12, pp. 1-9.
Clewell, D. B., S. E. Flannagan, L. O. Zitzow, Y. A. Su, P. He, E. Senghas, and K. E. Weaver. 1991. Properties of conjugative transposon Tn916, p. 39-44. In G. M. Dunny, P. Patrick, and L. L. Cleary (ed.), Genetics and molecular biology of streptococci, lactococci, and enterococci. American Society for Microbiology, Washington, D.C.
Chopin, A., M.-C. Chopin, A. Moillo-Batt, and P. Langella. 1984. Two plasmid-determined restriction and modification systems in *Streptococcus lactis*. Plasmid 11:260-263.
Crutz-Le Coq, A.-M., B. Cesselin, J. Commissaire. and J. Anba. 2002. Sequence analysis of the lactococcal bacteriophage bIL170: insights into structural proteins and HNH endonucleases in dairy Phages. Microbiol. 148:985-1001.
Dinsmore, P. K., D. A. Romero, and T. R. Klaenhammer. 1993. Insertional mutagenesis in *Lactococcus lactis* subsp. *lactis* mediated by IS946. FEMS Microbiol. Lett. 107:43-48.
Higgins, D.G., and P.M. Sharp. 1989. Fast and sensitive multiple sequence alignents on a microcomputer. Comput Appl Biosci. 5:151-153.

(Continued)

Primary Examiner — Nancy A Treptow

(57) ABSTRACT

The present invention relates to a nucleic acid comprising a *Lactococcus* CRISPR repeat region and/or a *Lactococcus* CRISPR spacer region.

27 Claims, 4 Drawing Sheets

(56) References Cited

OTHER PUBLICATIONS

Marraffini, L.A., and E.J. Sontheimer. 2010. Self versus non-self discrimination during CRISPR RNA-directed immunity. Nature 463:568-571.
Shah, S.A., Hansen, N.R., Garrett, R.A., 2009. Distributions of CRISPR spacer matches in viruses and plasmids of crenarchaeal acidothermophiles and implications for their inhibitory mechanism. Biochem. Soc. Trans. 37: 23-28.
Trotter, M., O. McAuliffe, M. Callanan, R. Edwards' G.F. Fitzgerald, A. Coffey, and R.P. Ross. 2006. Genome analysis of the obligately lytic bacteriophage 4268 of *Lactococcus lactis* provides insight into its adaptable nature. Gene 366:189-199.

\* cited by examiner ously incorporated herein by reference in its entirety.

LACTOCOCCUS CRISPR-CAS SEQUENCES

CLAIM FOR PRIORITY

This application claims priority under 35 USC 371 to International Application No. PCT/US2011/057102, filed on Oct. 20, 2011, which claims priority to U.S. Patent Application No. 61/394,976, filed Oct. 20, 2010, and U.S. Patent Application No. 61/405,317, filed Oct. 21, 2010, each of which is hereby incorporated by reference in its entirety.

FIELD OF THE INVENTION

The present invention relates to the CRISPR-Cas loci of *Lactococcus*, particularly *Lactococcus chungangensis, Lactococcus fujiensis, Lactococcus garvieae, Lactococcus lactis, Lactococcus lactis* subsp. *cremoris, Lactococcus lactis* subsp. *hordniae, Lactococcus lactis* subsp. *lactis, Lactococcus lactis* subsp. *tructae, Lactococcus piscium, Lactococcus plantarum, Lactococcus raffinolactis* and uses of these sequences.

BACKGROUND OF THE INVENTION

A CRISPR (Clustered Regularly Interspaced Short Palindromic Repeats) is a distinctive DNA locus (i.e., an array or cluster of repeated DNA sequences) found in the genomes of many bacteria and archaea (for recent reviews see e.g., Horvath and Barrangou, 2010; Karginov and Hannon, 2010).

Recently, it has been shown that CRISPR sequences can function as a type of "immune system" that help bacteria to defend themselves against phage infections (see e.g., Barrangou et al., 2007); Deveau et al., 2008; Horvath et al., 2008). At least eight distinct CRISPR loci have been identified in the genomes of lactic acid bacteria (see Horvath et al., 2009).

Furthermore, it has been shown that phage resistance in bacteria can be modified by introducing CRISPR sequences into the bacterial genome. For example, removal or addition of particular CRISPR sequences from *Streptococcus. thermophilus* strains resulted in a modified phage-resistance phenotype (see e.g., Barrangou et al., 2007; Deveau et al., 2008). International Publ. No. WO 2007/025097 A2, published Mar. 1, 2007 (which is hereby incorporated by reference herein) discloses inter alia the use of CRISPR loci to modulate the resistance of a bacterial strain against an exogenous nucleic acid (e.g., phage infection).

The structure of a CRISPR array includes a number of short repeating sequences referred to as "repeats." The repeats occur in clusters and up to 249 repeats have been identified in a single CRISPR array (see e.g., Horvath and Barrangou, 2010) and are usually regularly spaced by unique intervening sequences referred to as "spacers." Typically, CRISPR repeats vary from about 24 to 47 by in length and are partially palindromic (Horvath and Barrangou, 2010). The repeats are generally arranged in clusters (up to about 20 or more per genome) of repeated units (Horvath and Barrangou, 2010). The spacers are located between two repeats and typically each spacer has a unique sequence of about 21-72 by in length (Horvath and Barrangou, 2010). Many spacers are identical to or have high similarity with known phage sequences. It has been shown that the insertion of a spacer sequence from a specific phage into a bacterial CRISPR can confer resistance to that phage (see e.g., Barrangou et al., 2007).

In addition to repeats and spacers, a CRISPR array may also include a leader sequence and often a set of two to six associated cas genes. Typically the leader sequence is an AT-rich sequence of up to 550 by directly adjoining the 5' end of the first repeat (Horvath and Barrangou, 2010). New repeat-spacer unit is almost always added to the CRISPR array between the leader and the first repeat (see e.g. Horvath and Barrangou, 2010). However, it has been found acquisition of phage resistance also can occur associated with new spacer addition and concomitant spacer deletion away from the CRISPR leader sequence (see e.g., Deveau et al., 2008).

It is believed that the proteins encoded by the associated cas genes act as a bacterial "immune system" that confer resistance against phages. It has been suggested that the array of repeat-spacer sequences are transcribed into a long RNA and the repeats assume a secondary structure which the Cas proteins recognize and process to form small RNAs that function via an RNA-interference-like mechanism (see Karginov and Hannon, 2010). Brouns et al. (2008) have reported that a complex of five Cas proteins (CasA, CasB, CasC, CasD, and CasE) in the *Escherichia coli* K12 CRISPR-Cas system referred to as "Cascade" cleaves a CRISPR RNA precursor in each repeat and retains the cleavage product containing a virus-derived sequence. It is proposed that assisted by the Cas3 helicase, these mature CRISPR RNAs then serve as small guide RNAs that enable Cascade to interfere with virus proliferation, (see e.g., Brouns et al., 2008).

CRISPR sequences are among the most rapidly evolving genomic structures in bacteria. Because of this, and their relative sequence simplicity (i.e., repeat-spacer-repeat) CRISPR sequences provide an ideal genomic system for detecting, typing and tracking specific strains of bacteria. Methods for using CRISPR sequences to detect, type, and track bacterial strains have been disclosed in e.g., U.S. published application 2006/01990190 A1, published Sep. 7, 2006, which is hereby incorporated by reference herein.

A CRISPR array also provides a very convenient, durable, natural and easy to detect genomic tagging system that does not impact other physiological properties of the tagged host. Methods for using known phage to induce a CRISPR tag (e.g., addition of a repeat-spacer unit) in a bacterial strain have been disclosed in e.g., U.S. published application 2008/0124725 A1, published May 29, 2008, which is hereby incorporated by reference herein.

SUMMARY OF THE INVENTION

Figure 1:
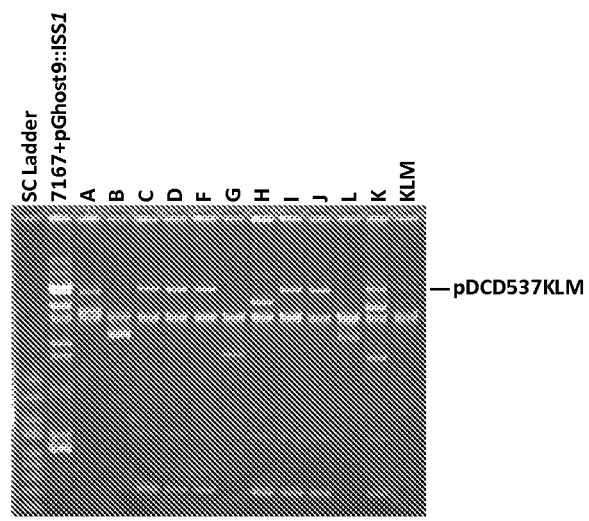
FIG. 1 shows the plasmid profile of 1403-S4 transconjugants A, B, C, D, E, F, G, H, I, J, L, and K, following conjugal mating between donor *L. lactis* DGCC7167+pG-host9::ISS1 and plasmid-free recipient IL1403-S4. Isolate KLM is a transconjugant from conjugal mating of between donor K and plasmid-free recipient LM2345.

The present invention is based on the extremely surprising finding of the inventors that *Lactococcus lactis* subsp. *cremoris* DGCC7167 (available as part of the CHOOZIT™ starter culture from Danisco A/S, Langebrogade 1, Copenhagen K, Denmark) comprises a CRISPR array. Prior to the inventors identifying this CRISPR region, the genomes of five *Lactococcus* lactis strains had been sequenced and no CRISPR locus nor cas gene had been identified. These strains were *Lactococcus lactis* subsp. *cremoris* strain MG1363 (accession AM406671), *Lactococcus lactis* subsp. *cremoris* strain NZ9000 (accession CP002094), *Lactococcus lactis* subsp. *cremoris* strain SK11 (accession Nos. CP000425 chromosome, CP000426 (plasmid1), CP000427 (plasmid2), CP000428, (plasmid3), CP000429 (plasmid4), CP000430 (plasmid5)), *Lactococcus lactis* subsp. *lactis* strain IL 403; (accession AE005176) and *Lactococcus lactis* subsp. *lactis* strain KF147 (accession CP001834 (chromosome), CP001835 (plasmid pKF147A)). Subsequently, a sixth strain was sequenced; *Lactococcus lactis* subsp. *lactis* CV56 (accession Nos. CP002365 chromosome, CP002366 (plasmidA), CP002367 (plasmidB), CP002368 (plasmidC), CP002369 (plasmidD), CP2370 (plasmidE)). In addition, no CRISPR/cas sequence could be detected among the 4076 GenBank entries (as of Oct. 11, 2011) classified as belonging to the *Lactococcus lactis* species.

Thus, the skilled person was led to believe that the CRISPR/Cas systems may be absent in *Lactococcus lactis*. Furthermore, based on global observations (Mojica et al., 2005; Makarova et al., 2006; Horvath et al., 2008; Shah et al., 2009; Horvath and Barrangou, 2010; Stern et al., 2010,) and specific experiments (Marraffini and Sontheimer, 2008; Marraffini and Sontheimer, 2010; Garneau et al., 2010), it is well-known and accepted that CRISPR-Cas loci are active against plasmids, possibly leading to plasmid loss. Because most of the industrially relevant traits are plasmid-encoded in *Lactococcus lactis*, a species in which plasmids are diverse, frequent and numerous, the skilled person would consider that it was likely that *Lactococcus lactis* is a species devoid of CRISPR-Cas loci because of the antagonism between CRISPR-Cas loci and plasmid maintenance. Also highly surprising is the identification in *Lactococcus lactis* of the CRISPR/Cas locus on a lactococcal native conjugative plasmid enabling natural dissemination to nonCRISPR/Cas harboring bacteria.

Also, *Lactococcus lactis* is amongst the lactic acid bacteria (LAB) species' possessing the highest number of different phage resistance mechanisms (restriction-modification systems, abortive infection systems, etc) (Sturino and Klaenhammer, 2004).

Therefore, according to a first aspect of the present invention there is provided a nucleic acid comprising a *Lactococcus* CRISPR repeat region and/or a *Lactococcus* CRISPR spacer region and/or a *Lactococcus* CRISPR cas gene.

According to a second aspect of the present invention there is provided a nucleic acid comprising:—
a) a nucleic acid sequence consisting of SEQ ID No: 24 or a sequence having at least 70%, 75%, 80%, 85%, 90%, 95%, 97%, 98%, 99% identity to SEQ ID No: 24, or a sequence capable of hybridizing under stringent conditions to SEQ ID No: 24; and/or
b) at least one nucleic acid sequence selected from the group consisting of SEQ ID Nos: 25 to 60 or a sequence having at least 70%, 75%, 80%, 85%, 90%, 95%, 97%, 98%, 99% identity to any one of SEQ ID Nos: 25 to 60, or a sequence capable of hybridizing under stringent conditions to any one of SEQ ID Nos: 25 to 60; and/or
c) at least one nucleic acid sequence selected from the group consisting of SEQ ID Nos: 2, 3, 5, 7, 9, 11, 13, 15, 17, and/or 21, or a sequence having at least 70%, 75%, 80%, 85%, 90%, 95%, 97%, 98%, 99% identity to any one of SEQ ID No: 2, 3, 5, 7, 9, 11, 13, 15, 17, and/or 21, or a sequence capable of hybridizing under stringent conditions to any one of SEQ ID No: 2, 3, 5, 7, 9, 11, 13, 15, 17, and/or 21.

According to a third aspect of the present invention there is provided a vector (e.g. a plasmid) comprising a nucleic acid sequence according to the first or second aspect.

According to a fourth aspect of the present invention there is provided a host cell having altered phage resistance comprising a nucleic acid according to the first or second aspect or the vector according to the third aspect.

According to a fifth aspect of the present invention there is provided a method for preparing a variant bacterial strain with altered phage resistance comprising:
(a) transforming bacteria with a nucleic acid comprising a *Lactococcus* CRISPR spacer sequence or with a vector (e.g. plasmid) comprising a nucleic acid sequence according to the first or second aspect (optionally further comprising a selection marker);
(b) contacting the transformed bacteria with a phage; and
(c) isolating transformed bacteria that exhibit altered resistance to the phage.

According to a sixth aspect there is provided a variant bacterial strain obtained using the method according to the fifth aspect.

According to a seventh aspect of the present invention there is provided a method for strain typing *Lactococcus*, comprising:
(a) amplifying genomic DNA from a strain of interest using at least one primer pair, wherein the genomic DNA comprises at least a portion of a sequence of a CRISPR array;
(b) detecting an amplicon generated in step (a), whereby said detected amplicon indicates the strain type,
wherein each primer of a pair is complementary to at least a portion of a repeat sequence of the CRISPR array, whereby the amplicon generated comprises at least one spacer sequence located of the CRISPR array and wherein the repeat sequence of the CRISPR array is corresponding to SEQ ID NO: 24.

According to an eighth aspect of the present invention there is provided a method for strain typing kit comprising:
(a) a container of an amplification mixture comprising a DNA polymerase, an amplification buffer, and at least one primer pair, wherein each primer of the pair is complementary to a portion of genomic DNA such that the primer pair amplifies at least a portion of a repeat or spacer sequence of a CRISPR array selected from at least one of SEQ ID Nos: 24 to 60; and
(b) a container of a detection mixture comprising a probe capable of hybridizing under stringent conditions to at least a portion of the CRISPR array amplified by the primer pair.

According to a ninth aspect of the present invention there is provided a method for tagging a lactococcal strain comprising:

(a) exposing a parent lactococcal strain to a phage;
(b) selecting a phage insensitive mutant;
(c) comparing a CRISPR array sequence or a portion thereof from the parent strain and the phage insensitive mutant strain; whereby the presence of an additional repeat-spacer unit in the CRISPR array sequence of the phage insensitive mutant indicates that the strain is tagged.

In a tenth aspect there is provided a method for tagging a bacterial strain comprising the steps of:
(a) transforming bacteria with a nucleic acid comprising a *Lactococcus* CRISPR spacer sequence or with a vector (e.g. plasmid) comprising a nucleic acid sequence according to the first or second aspect (optionally further comprising a selection marker); and
(b) isolating transformed bacteria that exhibit altered resistance to the phage or
(c) isolating transformed bacteria containing the *Lactococcus* CRISPR spacer sequence.

In an eleventh aspect there is provided a variant bacterial (preferably lactococcal) cell comprising a nucleic acid sequence described herein or a vector described herein or a *Lactococcus* CRISPR array described herein.

In a twelfth aspect there is provided the use of a cell, a *Lactococcus* CRISPR spacer or a *Lactococcus* CRISPR repeat or a *Lactococcus* CRISPR array or a vector (e.g. plasmid) comprising a *Lactococcus* CRISPR spacer or a *Lactococcus* CRISPR repeat or a *Lactococcus* CRISPR array for modulating the resistance of a cell (e.g. a bacterial cell, preferably a lactococcal cell) against a target nucleic acid or a transcription product thereof.

In a thirteenth aspect there is provided a cell culture comprising a variant bacterial cell (suitably a lactococcal cell) comprising a *Lactococcus* CRISPR spacer or a *Lactococcus* CRISPR repeat or a *Lactcoccus* CRISPR array or a vector (e.g. plasmid) comprising a *Lactococcus* CRISPR spacer or a *Lactococcus* CRISPR repeat or a *Lactococcus* CRISPR array.

In a fourteenth aspect there is provided a bacterial culture (such as a starter culture, a probiotic culture, a dietary supplement culture or other useful cultures) comprising a variant bacterial cell (suitably a lactococcal cell) comprising a *Lactococcus* CRISPR spacer or a *Lactococcus* CRISPR repeat or a *Lactcoccus* CRISPR array.

In a fifteenth aspect there is provided a product (such as a food product or feed product or, personal care product, or health care product, or veterinary product or dietary supplement) comprising the cell culture or bacterial culture (such as a starter culture, a probiotic culture or a dietary supplement culture) described herein.

In a sixteenth aspect there is provided a process for preparing a product (such as a food product or feed product or, personal care product, or health care product, or veterinary product or dietary supplement) comprising the use of the variant bacterial cell, the cell culture or the culture described herein.

In a seventeenth aspect there is provided a product (such as a food product or feed product or, personal care product, or health care product, or veterinary product or dietary supplement) obtained or obtainable by the process described herein.

In an eighteenth aspect there is provided a host cell into which has been incorporated one or more of the nucleotide sequences described herein or vector or the CRISPR array described herein.

In a nineteenth methods for generating CRISPR-escape phage mutants comprising: (a) obtaining at least one parent phage and a phage-resistant lactococcal bacterial strain comprising at least one CRISPR locus, wherein the CRISPR locus comprises a nucleic acid sequence that is at least about 95% identical to at least one protospacer sequence in the genome of the at least one parent phage; (b) exposing the at least one parent phage to the phage-resistant lactococcal bacterial strain, under conditions such that at least one phage variant is produced; and (c) selecting the at least one phage variant, wherein the at least one phage variant exhibits the ability to infect the phage-resistant lactococcal bacterial strain and is a CRISPR-escape phage mutant.

In a twentieth aspect there is provided a CRISPR-escape phage mutants obtained using the methods set forth herein.

In a twenty-first aspect there is provided a method for controlling bacterial (preferably lactococcal) populations in a product comprising exposing compositions comprising at least one CRISPR-escape phage mutant to a fermentation medium, wherein the fermentation medium contains at least one population of undesirable bacteria, under conditions such that the population of the undesirable bacteria is reduced, and the fermentation medium is used to generate the product.

DETAILED DESCRIPTION

According to a first aspect of the present invention there is provided a nucleic acid comprising a *Lactococcus* CRISPR repeat region and/or a *Lactococcus* CRISPR spacer region and/or a *Lactococcus* CRISPR cas gene.

In one embodiment the nucleic acid may comprises a *Lactococcus* CRISPR spacer or repeat or a *Lactococcus* CRISPR cas gene obtainable (preferably obtained) from *Lactococcus lactis* species.

In another embodiment the nucleic acid may comprise a *Lactococcus* CRISPR spacer or repeat or a *Lactococcus* CRISPR cas gene obtainable (preferably obtained) from *Lactococcus lactis* subsp. *lactis* or *Lactoccocus lactis* subsp. *cremoris*.

In another embodiment the nucleic acid may comprise a *Lactococcus* CRISPR spacer or repeat or a *Lactococcus* CRISPR cas gene obtainable (preferably obtained) from *Lactococcus lactis* subsp. *lactis* strain DGCC 7285, DGCC 7296, DGCC 7519, DGCC 6237, or DGCC 7341 or *Lactoccocus lactis* subsp. *cremoris* strain DGCC 7167.

In one preferred embodiment the *Lactococcus* CRISPR spacer region is selected from the group consisting of SEQ ID Nos: 25 to 60 or a sequence having at least 70%, 75%, 80%, 85%, 90%, 95%, 97%, 98%, 99% identity to any one of SEQ ID Nos: 25 to 60, or a sequence capable of hybridizing under stringent conditions to any one of SEQ ID Nos: 25 to 60.

In a further preferred embodiment, the *Lactococcus* CRISPR repeat region comprises or consists of SEQ ID No: 24, or a sequence having at least 70%, 75%, 80%, 85%, 90%, 95%, 97%, 98%, 99% identity to SEQ ID No: 24, or a sequence capable of hybridizing under stringent conditions to SEQ ID No: 24.

According to a second aspect of the present invention there is provided a nucleic acid comprising:—
a) nucleic acid sequence shown as SEQ ID No: 24, or a sequence having at least 70%, 75%, 80%, 85%, 90%, 95%, 97%, 98%, 99% identity to SEQ ID No: 24, or a sequence capable of hybridizing under stringent conditions to SEQ ID No: 24; and/or
b) at least one nucleic acid sequence selected from the group consisting of SEQ ID Nos: 25 to 60 or a sequence having at least 70%, 75%, 80%, 85%, 90%, 95%, 97%, 98%, 99% identity to any one of SEQ ID Nos: 25 to 60, or a sequence capable of hybridizing under stringent conditions to any one of SEQ ID Nos: 25 to 60; and/or c) at least one nucleic acid sequence selected from the group consisting of SEQ ID Nos: 2, 3, 5, 7, 9, 11, 13, 15, 17, and/or 21, or a sequence having at least 70%, 75%, 80%, 85%, 90%, 95%, 97%, 98%, 99% identity to any one of SEQ ID No: 2, 3, 5, 7, 9, 11, 13, 15, 17, and/or 21, or a sequence capable of hybridizing under stringent conditions to any one of SEQ ID No: 2, 3, 5, 7, 9, 11, 13, 15, 17, and/or 21.

Preferably, the nucleic acid according to the first or second aspect further comprises SEQ ID NO: 22 or a portion thereof comprising at least 10, 15, 20, 30, 40, 50, 60, 70, 80, 90, 100, 120, 140, 160, 180 or 200 nucleotides.

Preferably the nucleic acid according to the first or second aspect further comprises at least one nucleic acid sequence selected from the group consisting of SEQ ID NOs: 2, 3, 5, 7, 9, 11, 13, 15, 17, and/or 21, or a sequence having at least 70%, 75%, 80%, 85%, 90%, 95%, 97%, 98%, 99% identity to any one of SEQ ID No: 2, 3, 5, 7, 9, 11, 13, 15, 17, and/or 21, or a sequence capable of hybridizing under stringent conditions to any one of SEQ ID No: 2, 3, 5, 7, 9, 11, 13, 15, 17, and/or 21.

In one embodiment the CRISPR repeat may be used together with at least one cas gene—thus forming a functional pair.

In one aspect, preferably the nucleic acid sequence according to the present invention is in an isolated form. The term "isolated" means that the nucleic acid sequence is at least substantially free from at least one other component with which the nucleic acid sequence is naturally associated in nature and as found in nature. The nucleic acid sequence of the present invention may be provided in a form that is substantially free of one or more contaminants with which the substance might otherwise be associated. Thus, for example it may be substantially free of one or more potentially contaminating polypeptides and/or nucleic acid molecules.

According to a third aspect of the present invention there is provided a vector (e.g. plasmid) comprising a nucleic acid sequence according to the first or second aspect.

In one embodiment of the invention, the vector comprises the CRISPR/Cas locus on a lactococcal native conjugative plasmid enabling natural dissemination to non-CRISPR/Cas harboring bacteria.

In a second embodiment, the vector may be in the form of a transposable element.

According to a fourth aspect of the present invention there is provided a host cell having altered phage resistance comprising a nucleic acid according to the first aspect or the vector according to the third aspect.

In one embodiment the host cell is recombinant.

In a preferred embodiment said host cell is a bacterial cell. More preferably said bacterial cell is a lactic acid bacterial cell. In one embodiment the lactic acid bacterial cell may be selected from the group consisting of *Bifidobacterium* species, a *Brevibacterium* species, a *Propionibacterium* species, a *Lactococcus* species, a *Streptococcus* species, a *Lactobacillus* species including the *Enterococcus* species, *Pediococcus* species, a *Leuconostoc* species and *Oenococcus* species. Suitable species include, but are not limited to *Lactococcus lactis*, including *Lactococcus lactis* subsp. *lactis* and *Lactococcus lactis* subsp. *cremoris*, *Lactococcus lactis* subsp. *cremoris*, *Leuconostoc* sp., *Lactococcus lactis* subsp. *lactis* biovar, *Streptococcus thermophilus*, *Lactobacillus delbrueckii* subsp. *bulgaricus* and *Lactobacillus helveticus*, *Bifidobacterium lactis*, *Lactobacillus acidophilus*, *Lactobacillus casei*.

Even more preferably the lactic acid bacterial cell is a *Lactococcus* cell, most preferably a *Lactococcus chungangensis*, *Lactococcus fujiensis*, *Lactococcus garvieae*, *Lactococcus lactis*, *Lactococcus lactis* subsp. *cremoris*, *Lactococcus lactis* subsp. *hordniae*, *Lactococcus lactis* subsp. *lactis*, *Lactococcus lactis* subsp. *tructae*, *Lactococcus piscium*, *Lactococcus* plantarum, *Lactococcus raffinolactis* cell.

In a most preferred embodiment the cell is a *Lactococcus lactis* cell.

According to a fifth aspect of the present invention there is provided a method for preparing a variant bacterial strain with altered phage resistance comprising:

(a) transforming bacteria with a nucleic acid comprising a *Lactococcus* CRISPR spacer sequence sequence or with a vector (e.g. plasmid) comprising a nucleic acid sequence according to the first or second aspect (optionally further comprising a selection marker);

(b) contacting the transformed bacteria with a phage; and (c) isolating transformed bacteria that exhibit altered resistance to the phage.

It will be understood that in some embodiments, the recombinant bacteria strain has increased phage resistance (e.g., complete resistance), and in other embodiments phage resistance is decreased (e.g., no resistance to phage infection).

In one embodiment the *Lactococcus* CRISPR spacer sequence is selected from at least one of SEQ ID NOs: 25-60 or a sequence having at least 70%, 75%, 80%, 85%, 90%, 95%, 97%, 98%, 99% identity to any one of SEQ ID Nos: 25 to 60 or a sequence capable of hybridizing under stringent conditions to any one of SEQ ID Nos: 25 to 60.

In a further embodiment the nucleic acid comprises a repeat-spacer unit sequence, wherein the repeat sequence comprises or consists of SEQ ID NO: 24 or a sequence having at least 70%, 75%, 80%, 85%, 90%, 95%, 97%, 98%, 99% identity to SEQ ID No: 24 or a sequence capable of hybridizing under stringent conditions to SEQ ID No: 24, and the spacer sequence is selected from at least one of SEQ ID NOs: 25 to 60 or a sequence having at least 70%, 75%, 80%, 85%, 90%, 95%, 97%, 98%, 99% identity to any one of SEQ ID Nos: 25 to 60 or a sequence capable of hybridizing under stringent conditions to any one of SEQ ID Nos: 25 to 60.

In a further embodiment the nucleic acid comprises SEQ ID NO: 22 or a portion thereof comprising at least 10, 15, 20, 30, 40, 50, 60, 70, 80, 90, 100, 120, 140, 160, 180 or 200 nucleotides.

In a still further embodiment the nucleic acid further comprises at least one cas gene selected from the group consisting of SEQ ID Nos: 2, 3, 5, 7, 9, 11, 13, 15, 17, 19 and/or 21.

Preferably, the bacterial strain is a lactic acid bacterial strain, more preferably a *Lactococcus* species strain, most preferably a *Lactococcus chungangensis*, *Lactococcus fujiensis*, *Lactococcus garvieae*, *Lactococcus lactis*, *Lactococcus lactis* subsp. *cremoris*, *Lactococcus lactis* subsp. *hordniae*, *Lactococcus lactis* subsp. *lactis*, *Lactococcus lactis* subsp. *tructae*, *Lactococcus piscium*, *Lactococcus plantarum*, *Lactococcus raffinolactis* strain.

In a most preferred embodiment the cell is a *Lactococcus lactis* cell.

According to a sixth aspect there is provided a variant bacterial strain obtained using the method according to the fifth aspect.

According to a seventh aspect of the present invention there is provided a method for strain typing strain detecting, and/or strain tracking *Lactococcus* comprising:

(a) amplifying genomic DNA from a strain of interest using at least one primer pair, wherein the genomic DNA comprises at least a portion of a sequence of a CRISPR array;
(b) detecting an amplicon generated in step (a), whereby said detected amplicon indicates the strain type,
wherein each primer of a pair is complementary to at least a portion of a repeat sequence of the CRISPR array, whereby the amplicon generated comprises at least one spacer sequence located of the CRISPR array and wherein the repeat sequence of the CRISPR array is corresponding to SEQ ID NO: 24.

In some embodiments of the method, detecting an amplicon is carried out using a method selected from: measurement of relative size by gel electrophoresis (e.g., agarose gels) or mass spectrometric analysis; hybridization to probes of known sequence (e.g., immobilized probes on a microarray); and sequencing (e.g., determination of partial or complete sequence of the amplicon. In some embodiments of the method, each primer of the pair is complementary to at least a portion of a sequence of a CRISPR array. In some embodiments, one primer of the pair is complementary to the first repeat and the other primer of the pair is complementary to the terminal repeat of the CRISPR array, whereby the amplicon generated comprises all of the CRISPR array, or at least a portion of every repeat and spacer of the CRISPR array.

In some embodiments of the methods for strain typing, strain detecting, and/or strain tracking, each primer of a pair is complementary to a portion of genomic DNA such that the primer pair amplifies at least a portion of a CRISPR array. Typically, said portions of genomic DNA will comprise sequences directly adjacent to and/or part of the CRISPR array sequence. In some embodiments of the methods, each primer of a pair is complementary to at least a portion of a repeat sequence of the CRISPR array, whereby amplification generates an amplicon comprising at least one spacer sequence of the CRISPR array. In some embodiments of the methods, primer pair sequences are selected wherein each primer is complementary to at least a portion of a different end (i.e., either 5' or 3') of the CRISPR array repeat sequence, whereby amplification generates a plurality of amplicons having sequences of a plurality of the spacers located between the repeats of the CRISPR array. In such an embodiment, the plurality of amplicons are detected by sequencing or hybridization to a plurality of probes complimentary to the spacer sequences. In one embodiment of the method, the plurality of amplicons is hybridized to a plurality of immobilized probes (e.g., a microarray), whereby the plurality of spacer sequences detected indicates the specific strain of interest.

In other embodiments of the method, each primer of a pair is complementary to at least a portion of a spacer sequence of the CRISPR array, and in some embodiments, each primer of a pair is complementary to at least a portion of a different spacer sequence, whereby the amplicon generated comprises at least one repeat sequence located between the two spacer sequences. In some embodiments of the method, one primer of the pair is complementary to the spacer sequence adjacent to the first repeat of the CRISPR array. In some embodiments, one primer of the pair is complementary to the spacer sequence adjacent to the first repeat of the CRISPR array and the other primer of the pair is complementary to the spacer sequence adjacent to the terminal repeat of the CRISPR array, whereby the amplicon generated comprises all of, or at least a portion of every spacer in the CRISPR array More preferably, the CRISPR array comprises at least two spacer sequences, and each primer of a pair is complementary to at least a portion of a different spacer sequence, whereby the amplicon generated comprises at least one repeat sequence located between the two spacer sequences.

In one embodiment one primer of the pair is complementary to the spacer sequence adjacent to the first repeat of the CRISPR array.

In a preferred embodiment, the CRISPR array comprises SEQ ID NO: 22 or a portion thereof comprising at least 10, 15, 20, 30, 40, 50, 60, 70, 80, 90, 100, 120, 140, 160, 180 or 200 nucleotides.

More preferably, the amplicon is detected by hybridization to an immobilized probe.

According to an eighth aspect of the present invention there is provided a method for strain typing kit comprising:
(a) a container of an amplification mixture comprising a DNA polymerase, an amplification buffer, and at least one primer pair, wherein each primer of the pair is complementary to a portion of genomic DNA such that the primer pair amplifies at least a portion of a repeat or spacer sequence of a CRISPR array selected from at least one of SEQ ID Nos: 24 to 60; and
(b) a container of a detection mixture comprising a probe capable of hybridizing under stringent conditions to at least a portion of the CRISPR array amplified by the primer pair.

According to an ninth aspect of the present invention there is provided a method for tagging a lactococcal strain comprising:
(a) exposing a parent lactococcal strain to a phage;
(b) selecting a phage insensitive mutant;
(c) comparing a CRISPR array sequence or a portion thereof from the parent strain and the phage insensitive mutant strain; whereby the presence of an additional repeat-spacer unit in the CRISPR array sequence of the phage insensitive mutant indicates that the strain is tagged.

In an alternative embodiment, there is provided a method for tagging a lactococcal strain comprising the steps of:
 (a) exposing a parent lactococcal strain comprising at least a portion of a CRISPR array to at least one nucleic acid sequence to produce a mixture of *Lactococcus* comprising at least one bacteriophage resistant strain comprising a modified CRISPR array;
 (b) selecting said bacteriophage resistant strain from said mixture of bacteria;
 (c) selecting said bacteriophage resistant strains comprising an additional nucleic acid fragment in said modified CRISPR array from said bacteriophage resistant strains selected in step (b) whereby the presence of a modified CRISPR array sequence of the phage insensitive mutant indicates that the strain is tagged; and
 (d) isolating said tagged strain, wherein said strain comprises an additional nucleic acid fragment in said modified CRISPR array.

In another alternative embodiment, there is provided a method for tagging a bacterial strain comprising the steps of:
(a) transforming bacteria with a nucleic acid comprising a *Lactococcus* CRISPR spacer sequence; and
(b) isolating transformed bacteria that exhibit altered resistance to the phage, or
(c) isolating transformed bacteria containing the *Lactococcus* CRISPR spacer sequence. Suitably the bacterial strain that is to be tagged may not naturally comprise a CRISPR array.

Suitably the bacteria strain may be a lactococcal strain.

It will be understood that the CRISPR array comprises SEQ ID NO: 22 or a portion thereof comprising at least 10, 15, 20, 30, 40, 50, 60, 70, 80, 90, 100, 120, 140, 160, 180 or 200 nucleotides.

In a further aspect, the invention provides an isolated nucleic acid encoding a csm/cas gene of the *Lactococcus lactis* CRISPR array. In some embodiments, the csm/cas gene of the *Lactococcus lactis* CRISPR array encodes an amino acid sequence selected from group consisting of SEQ ID NOs: 4, 6, 8, 10, 12, 14, 16, 18, and 20 or sequence having at least 70%, 75%, 80%, 85%, 90%, 95%, 97%, 98% or 99% identity thereto.

In some embodiments, the invention provides an isolated nucleic acid comprising a nucleic acid sequence comprising two or more csm/cas genes, wherein the csm/cas genes encode two or more amino acid sequences selected from group consisting of SEQ ID NOs: 4, 6, 8, 10, 12, 14, 16, 18, and 20 or sequence having at least 70%, 75%, 80%, 85%, 90%, 95%, 97%, 98% or 99% identity thereto. In one embodiment, the isolated nucleic acid comprises at least 2 csm/cas genes, suitably at least 3, at least 4, at least 5, at least 6, at least 7 or all eight csm/cas genes of the *Lactococcus lactis* CRISPR array.

In an eleventh aspect there is provided a variant bacterial (preferably lactococcal) cell comprising a nucleic acid sequence described herein or a vector described herein or a *Lactococcus* CRISPR spacer described herein.

In a twelfth aspect there is provided the use of a cell, a *Lactococcus* CRISPR spacer or a *Lactococcus* CRISPR repeat or a *Lactococcus* CRISPR array for modulating the resistance of a cell (e.g. a bacterial cell, preferably a lactococcal cell) against a target nucleic acid or a transcription product thereof.

In a thirteenth aspect there is provided a cell culture comprising a variant bacterial cell (suitably a lactococcal cell) comprising a *Lactococcus* CRISPR spacer or a *Lactococcus* CRISPR repeat or a *Lactcoccus* CRISPR array or a vector described herein.

In a fourteenth aspect there is provided a bacterial culture (such as a starter culture, a probiotic culture, a dietary supplement culture or other useful cultures) comprising a variant bacterial cell (suitably a lactococcal cell) comprising a *Lactococcus* CRISPR spacer or a *Lactococcus* CRISPR repeat or a *Lactcoccus* CRISPR array or a vector described herein.

In a fifteenth aspect there is provided a product (such as a food product or feed product or, personal care product, or health care product, or veterinary product or dietary supplement) comprising the cell culture or bacterial culture (such as a starter culture, a probiotic culture or a dietary supplement culture) described herein.

In a sixteenth aspect there is provided a process for preparing a product (such as a food product or feed product or, personal care product, or health care product, or veterinary product or dietary supplement) comprising the use of the variant bacterial cell, host cells, the cell culture or the culture described herein. In some embodiments the product is inoculated with the variant bacterial cell, host cells, the cell culture or the culture of the present invention. In some embodiments the product is fermented by the variant bacterial cell, host cells, the cell culture or the culture of the present invention.

In a seventeenth aspect there is provided a product (such as a food product or feed product or, personal care product, or health care product, or veterinary product or dietary supplement) obtained or obtainable by the process described herein.

In an eighteenth aspect there is provided a host cell into which has been incorporated one or more of the nucleotide sequences described herein or the vector described herein or the CRISPR array described herein.

In a nineteenth, methods for generating CRISPR-escape phage mutants comprising: (a) obtaining: at least one parent phage and a phage-resistant lactococcal bacterial strain comprising at least one CRISPR locus, wherein the CRISPR locus comprises a nucleic acid sequence that is at least about 95% identical to at least one protospacer sequence in the genome of the at least one parent phage; (b) exposing the at least one parent phage to the phage-resistant lactococcal bacterial strain, under conditions such that at least one phage variant is produced; and (c) selecting the at least one phage variant, wherein the at least one phage variant exhibits the ability to infect the phage-resistant lactococcal bacterial strain and is a CRISPR-escape phage mutant.

In some embodiments the phage-resistant lactococcal bacterial strain is a bacteriophage-resistant variant strain obtained using the methods set forth herein.

In some embodiments, the methods further comprise the step of comparing at least a portion of the at least one protospacer sequence and a CRISPR motif positioned near the at least one protospacer sequence in the phage variant with the at least one protospacer sequence and CRISPR motif of the parent phage.

In yet additional embodiments, the methods further comprise the step of selecting the variant phages that infect the phage resistant lactococcal bacterial strain, wherein the variant phages comprise the CRISPR-escape phage mutants, and wherein the CRISPR-escape phages comprise at least one mutation in the at least one protospacer sequence and/or in the CRISPR motif of the CRISPR-escape phage mutants.

In yet additional embodiments, the methods are iteratively repeated one or more times using the CRISPR-escape phage mutants and different CRISPR phage-resistant bacterial (suitably lactococcal) strains comprising at least one CRISPR locus, wherein the CRISPR locus comprises a nucleic acid sequence that is at least about 95% identical to at least one protospacer sequence in the genome of the CRISPR-escape phage mutants.

In yet additional embodiments, at least one bacteriophage is selected from the group of virus families consisting of: Corticoviridae, Cystoviridae, Inoviridae, Leviviridae, Microviridae, Myoviridae, Podoviridae, Siphoviridae, and Tectiviridae. In some preferred embodiments, the phage-resistant bacterial strain is selected from *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Enterococcus, Clostridium, Camplyobacter, Corynebacterium, Mycobacterium, Treponema, Borrelia, Francisella, Brucella, Klebsiella, Frankia, Bartonella, Rickettsia, Shewanella, Serratia, Enterobacter, Proteus, Providencia, Brochothrix, Bifidobacterium, Brevibacterium, Propionibacterium, Lactococcus, Lactobacillus, Pediococcus, Leuconostoc, Streptococcus,* and *Oenococcus*.

In a twentieth aspect there is provided a CRISPR-escape phage mutants obtained using the methods set forth herein.

In some embodiments, the CRISPR-escape phage mutants comprise two or more mutations present in at least two protospacer sequences and/or in the CRISPR spacer.

The present invention also provides CRISPR-escape phage mutants, wherein the genome of the CRISPR-escape phage mutants is genetically engineered to comprise mutations in at least one protospacer and/or the CRISPR motif.

In some embodiments, at least one CRISPR motif is mutated in the CRISPR-escape phage mutants, while in some alternative embodiments, at least one CRISPR motif is deleted in the CRISPR-escape phage mutants. The present invention also provides compositions comprising at least one CRISPR-escape phage mutants.

The present invention also provides methods for controlling bacterial (preferably lactococcal) populations in a product comprising exposing compositions comprising at least one CRISPR-escape phage mutant to a fermentation medium, wherein the fermentation medium contains at least one population of undesirable bacteria, under conditions such that the population of the undesirable bacteria is reduced, and the fermentation medium is used to generate the product.

In some embodiments, the product is selected from foods, feeds, cosmetics, personal care products, health care products, veterinary products, and dietary supplements. In some further embodiments, the methods are repeated at least once and the different compositions and/or compositions comprising different CRISPR-escape phage mutants are used in rotation.

It will be readily apparent to the skilled person that repeat sequences or spacer sequences according to the present invention can be used in combination with repeat or spacer sequences known from the prior art, for example as described in WO2998/08989 or WO2010/054154, to provide variant bacterial strains having altered phage resistance.

It will further be apparent that any preferred features described in relation to one aspect or embodiment may be considered to be equally applicable to any other aspect or embodiment described herein.

All patents and publications, including all sequences disclosed within such patents and publications, referred to herein are expressly incorporated by reference. Unless defined otherwise herein, all technical and scientific terms used herein have the same meaning as commonly understood by one of ordinary skill in the art to which this invention belongs (see e.g., Singleton and Sainsbury, 2006 and Hale and Margham, 1991) both of which provide one of skill with a general dictionary of many of the terms used herein). Any methods and materials similar or equivalent to the various embodiments described herein can be used in the practice or testing of the present invention.

It is intended that every maximum (or minimum) numerical limitation disclosed in this specification includes every lower (or higher) numerical limitation, as if such lower (or higher) numerical limitations were expressly written herein. Moreover, every numerical range disclosed in this specification is intended include every narrower numerical range that falls within such broader numerical range, as if such narrower numerical ranges were all expressly written herein.

As described herein in greater detail, CRISPR loci typically consist of several non-contiguous direct repeats separated by stretches of variable sequences called spacers, and are often times adjacent to cas genes (CRISPR-associated). In silico analyses of the spacers have revealed sequence homology with foreign elements, including bacteriophage and plasmid sequences (see e.g., Bolotin et al., 2005; Mojica et al., 2005; Pourcel et al., 2005). Based exclusively on in silico analyses, several hypotheses had been put forward proposing roles for CRISPR and cas genes, that include providing immunity against foreign genetic elements via a mechanism based on RNA interference (Makarova et al., 2006). Subsequently, it has been biologically demonstrated that the CRISPR and cas genes function as a microbial defense mechanism against foreign nucleic acids (Barrangou et al., 2007, Marraffini and Sontheimer, 2008, Garneau et al., 2010).

Current strategies used in industry to minimize bacteriophage infection and the resultant failure of bacterial cultures, include the use of: (i) mixed starter cultures; and (ii) the use of alternating strains having different phage susceptibility profiles (i.e., strain rotation). Traditionally, starter cultures used in the dairy industry are mixtures of lactic acid bacterial strains. The complex composition of mixed starter cultures ensures that a certain level of resistance to phage attack is provided. However, repeated sub-culturing of mixed strain cultures leads to unpredictable changes in the distribution of individual strains and eventually often to undesired strain dominance. This in turn may lead to increased susceptibility to phage attack and risk of fermentation failures.

The rotation of selected bacterial strains which are sensitive to different phages is another approach currently used to limit phage development. However, it is difficult and cumbersome to identify and select a sufficient number of strains having different phage type profiles to provide an efficient and reliable rotation program. In addition, the continuous use of strains requires careful monitoring for new infectious phages and the need to quickly substitute an infected strain with a resistant bacterial strain. In manufacturing plants where large quantities of bulk starter cultures are prepared long before use, such a quick response is usually not possible. Thus, several attempts have been made to improve the resistance of cultures for use in industry.

In addition, although it would be useful to have starter cultures that are labelled such that their origin could be determined, this has not been done. Indeed, although it is feasible to insert a synthetic oligonucleotide into a strain to tag or label it, using recombinant DNA technologies, the labelled strain would be considered to be a genetically modified organism and may thereby face regulatory issues in commercial applications. Thus, there is a need in the art for natural methods and compositions suitable for introducing a unique sequence into bacteria that could be used to identify and/or track bacteria.

Bacteriophages are arguably the most abundant biological entity on the planet (see, Breitbart and Rohwer, 2005). Their ubiquitous distribution and abundance have an important impact on microbial ecology and the evolution of bacterial genomes (Chibani-Chemoufi et al., 2004). Consequently, bacteria have developed a variety of natural defense mechanisms that target diverse steps of the phage life cycle, notably blocking adsorption, preventing DNA injection, restricting the incoming DNA and abortive infection systems. These antiviral barriers can also be engineered and manipulated to better control phage populations (see e.g., Chibani-Chemoufi et al., 2004; Sturino and Klaenhammer, 2006).

Numerous bacteria have been selected by humans and used extensively for fermentation and biotechnology processes. Unfortunately, domesticated bacteria used in industrial applications are often susceptible to phage attack, including those genera and species widely used as dairy cultures (Brussow2001). Accordingly, the industry has devised various strategies to combat phage based on strain diversity, bacteriophage insensitive mutants, and plasmids bearing phage-resistance mechanisms.

Definitions

As used herein, the singular "a", "an" and "the" includes the plural reference unless the context clearly dictates otherwise. Thus, for example, reference to a "host cell" includes a plurality of such host cells.

As used herein the phrase "at least" when used in combination with a list of values or terms is meant to apply to each value or term in the list. For example, the phrase "at least 85%, 90%, 95% and 99% sequence identity" is used to denote at least 85%, at least 90%, at least 95% and/or at least 99% sequence identity.

As used herein the term "comprising" and its cognates are used in their inclusive sense; that is, equivalent to the term "including" and its corresponding cognates.

Unless otherwise indicated, nucleic acids are written left to right in 5' to 3' orientation; amino acid sequences are written left to right in amino to carboxyl orientation, respectively.

The headings provided herein are not limitations of the various aspects or embodiments of the invention that can be had by reference to the specification as a whole. Accordingly, the terms defined immediately below are more fully defined by reference to the Specification as a whole.

As used herein when describing proteins and genes that encode them, the term for the gene is generally italicized. The term for the protein is generally not italicized and the first letter is generally capitalized.

As used herein, "nucleic acid" refers to a nucleotide or polynucleotide sequence, and fragments or portions thereof, as well as to DNA and RNA of genomic or synthetic origin which may be double-stranded or single-stranded, whether representing the sense or antisense strand. The terms nucleic acid and isolated nucleic acid are used to refer to a nucleic acid removed from at least one other component with which it is naturally associated.

As used herein, "derived from" encompasses "originated from," "obtained from," or "isolated from."

As used herein, "bacteria" refers to any of the prokaryotic microorganisms that exist as a single cell or in a cluster or aggregate of single cells.

As used herein, the term "CRISPR array" refers to the DNA segment which includes all of the CRISPR repeats and spacers, starting with the first nucleotide of the first CRISPR repeat and ending with the last nucleotide of the last (terminal) CRISPR repeat. Typically, each spacer sequence in a CRISPR array is located between two repeats and consequently, a locus includes one more repeat than spacer sequence. In one embodiment the CRISPR array may also include a CRISPR leader sequence and/or a set of two to six associated cas genes.

As used herein, the terms "CRISPR repeat," "repeat sequence," or "repeat" have the conventional meaning as used in the art—i.e., multiple short direct repeating sequences, which show very little or no sequence variation within a given CRISPR array.

As used herein, "CRISPR spacer," "spacer sequence," or "spacer" refer to the non-repetitive sequences that are located between the repeats of a CRISPR array.

In some embodiments of the present invention, a "spacer" refers to the nucleic acid segment that is flanked by two repeats. CRISPR spacer sequences often have significant homology to naturally occurring phage or plasmid sequences. Typically, spacers are located between two identical or nearly identical repeat sequences. Thus, spacers often are identified by sequence analysis of the DNA segments located between two CRISPR repeats.

As used herein the term "repeat-spacer" refers to spacer sequence associated with at least one repeat sequence.

As used herein, the term "csm/cas gene" has its conventional meaning as used in the art where it refers to the one or more genes that are coupled to, associated with, close to, or in the vicinity of a CRISPR array. It will be understood that csm and cas are synonymous and are used interchangeably herein. A comprehensive review of the Cas protein family is presented by Haft et al. (2005; see also, Brouns et al., 2008).

As used herein, a "CRISPR leader," "leader sequence," or "leader" refers to the non-coding sequence located directly upstream of the 5' end of the CRISPR array. Typically, the CRISPR leader sequence is located between the first nucleotide of the first repeat in the CRISPR array and the stop codon of the last cas gene.

As used herein, "CRISPR trailer" refers to the non-coding sequence located directly downstream of the 3' end of the CRISPR array—i.e., right after the last nucleotide of the last CRISPR repeat. This last CRISPR repeat is also referred to as a "terminal repeat."

As used herein, the term "bacteriophage" or "phage" has its conventional meaning as understood in the art—i.e., a virus that selectively infects one or more bacterial species.

As used herein, the terms "tagged bacteria," "tagged bacterium," and "labelled bacteria" are all used interchangeably to refer to a bacteria that has been exposed to a phage and in which one or more CRISPR loci or a portion thereof have been modified in such a way that the bacteria are resistant to the phage. As described in further detail herein, in some embodiments, the tagged bacteria are exposed to more than one phage (e.g., either iteratively, sequentially or simultaneously), such that more than one genomic modifications accumulate within its CRISPR loci in such a way that it becomes insensitive to each of the phages to which it has been exposed. As used herein, the terms "tagged bacteria," "tagged bacterium," and "labelled bacteria" are all used interchangeably to refer to a bacteria that has acquired the CRISPR loci and/or cas genes and in which the CRISPR/Cas loci may or may not confer the bacteria resistant to phage.

As used herein, the terms "tagged bacteria," "tagged bacterium," and "labelled bacteria" are all used interchangeably to refer to a bacteria that has acquired the CRISPR loci or CRISPR array and/or cas genes and in which the CRISPR-Cas loci may or may not confer the bacteria resistant to phage.

As used herein, the terms "altered" or "altering" used in the context of a cell's resistance to a nucleic acid may refer to suppressing, reducing, decreasing, inducing, conferring, restoring, elevating, increasing or otherwise affecting the resistance of a cell to a target nucleic acid.

As used herein, the term "resistance to a target nucleic acid" means that resistance conferred against any entity that comprises or produces the target nucleic acid or a transcription product thereof (e.g., a cell, a phage, plasmids, "naked" DNA). The types of entities are not limited to living entities, such as cells and phage, but also include non-living entities e.g., plasmids, or transposable elements. Thus, in some embodiments, the CRISPR sequences of the present invention can provide resistance against any amino-acid containing entity and even free or "naked" nucleic acid sequences that include a target nucleic acid. Resistance can be measured in terms of the survival of the resistant cell or in terms of the prevention of the maintenance and/or survival of the incoming nucleic acid (e.g., prevention of the target nucleic acids replication and/or transcription and/or expression). Resistance is not intended to indicate that foreign DNA is necessarily precluded from entering into the resistant cell (i.e., penetration through the cell membrane). Furthermore, the term "resistance" is not meant to imply that a cell is 100% resistant to a target nucleic acid or a transcription product thereof, but includes cells that are tolerant of the target nucleic acid or a transcription product thereof. In some embodiments the term resistance means 100% resistant.

As used herein, "amplification" refers to the production of additional copies of a nucleic acid sequence. Amplification is used in many of the applications of CRISPR sequences (see e.g., Mojica et al., 2005; and Pourcel et al., 2005) including the embodiments disclosed herein (e.g., strain detecting, typing, tracking, and tagging). In the embodiments of the present invention, amplification typically is carried out using the "polymerase chain reaction" ("PCR") method well-known to those in the art. In addition, other amplification methods, including but not limited to ligase chain reaction ("LCR") and isothermal amplification methods find use in the present invention. Well-known isothermal amplification methods useful in the present invention include, but are not limited to, strand displacement amplification (SDA), Q-beta-replicase, nucleic acid-based sequence amplification (NASBA), and self-sustained sequence replication.

In some other preferred embodiments of the present invention, the CRISPR array or a portion thereof from the parent bacterium and the labelled bacterium are compared by sequencing the CRISPR array or a portion thereof of the present invention, the CRISPR array or a portion thereof from the parent bacterium and the labelled bacterium are compared by amplifying and then sequencing the CRISPR array or a portion thereof. In some embodiments, one end of the CRISPR array are compared, while in other embodiments, both the 5' and 3' ends of the loci are compared. In some preferred embodiments, one end (e.g., the 5' end) of the CRISPR array are compared. In yet other embodiments, at least the last CRISPR repeat at the 3' end of the CRISPR array and/or at least the last CRISPR spacer (e.g., the last CRISPR spacer core) at the 3' end of the CRISPR array and/or at least the first CRISPR repeat at the 5' end of the CRISPR array and/or at least the first CRISPR spacer (e.g., the first CRISPR spacer core) at the 5' end of the CRISPR array are compared. In some preferred embodiments, at least the first CRISPR repeat at the 5' end of the CRISPR array and/or at least the first CRISPR spacer (e.g., the first CRISPR spacer core) at the 5' end of the CRISPR array are compared. In some additional preferred embodiments, at least the last CRISPR spacer (e.g., the last CRISPR spacer core) at the 3' end of the CRISPR array and/or at least the first CRISPR spacer (e.g., the first CRISPR spacer core) at the 5' end of the CRISPR array are compared. In some further preferred embodiments, at least the first CRISPR spacer (e.g., the first CRISPR spacer core) at the 5' ends of the CRISPR loci are compared.

In some embodiments, the CRISPR loci comprise DNA, while in other embodiments, the CRISPR loci comprise RNA. In some embodiments, the nucleic acid is of genomic origin, while in other embodiments, it is of synthetic or recombinant origin. In some embodiments, the CRISPR loci are double-stranded, while in other embodiments, they are single-stranded, whether representing the sense or antisense strand or combinations thereof. In some embodiments, CRISPR loci are prepared by use of recombinant DNA techniques (e.g., recombinant DNA), as described herein.

The present invention also provides methods for generating CRISPR variants. These variants are expressed, isolated, cloned, and/or sequenced using any suitable method known in the art. In some particularly preferred embodiments, the CRISPR variants are phage resistant mutant strains that have a modified CRISPR array with an additional spacer. In some additional embodiments, these variants find use as targets for detection/identification purposes, or for engineering resistance against nucleic acid molecules. In still further embodiments, these variants find use in the development of biocontrol agents.

As used herein, "primer" refers to an oligonucleotide, which is naturally occurring (e.g., from a purified restriction digest) or produced synthetically, which is capable of acting as a point of initiation of synthesis (e.g., for an amplification) when placed under conditions in which synthesis of a primer extension product which is complementary to a nucleic acid strand (e.g., an amplicon) is induced (i.e., at a suitable temperature, pH, and in the presence of nucleotides and an inducing agent such as DNA polymerase). PCR primers can be made up of ribonucleotides, deoxyribonucleotides, or synthetic analogs thereof, and typically are at least about 10 nucleotides in length, and most typically at least about 20 nucleotides in length. Methods for designing and conducting PCR are well known in the art, and include, but are not limited to methods using paired primers, nested primers, single specific primers, degenerate primers, gene-specific primers, vector-specific primers, partially mismatched primers, etc.

In various embodiments of the present invention, pairs of primers are used in PCR to amplify all or a portion of a CRISPR array. In some embodiments, the primer can be single stranded, e.g., for maximum efficiency in amplification, however in other embodiments, the primer can be double-stranded. In some embodiments, the primer can be an oligodeoxyribonucleotide. Generally, the primer must be an oligonucleotide that is sufficiently long to prime the synthesis of extension products in the presence of the inducing agent. The selected length of the primer used in embodiments of the present invention will depend on factors, including temperature, source of primer, and the particular application.

As used herein, the term variant when referring to a bacterial strain refers to a strain which is a phage resistant bacterial strain having a modified CRISPR array comprising at least one additional spacer. It will be understood that the term variant encompasses recombinant bacterial strains. The term variant is used when referring to a bacterial strain which is modified to introduce (e.g. by conjugation, transformation, competence or other means) a nucleic acid sequence in accordance with the present invention, or a *Lactococcus* CRISPR spacer, or a *Lactococcus* CRISPR repeat or a *Lactococcus* CRISPR array, which bacterial strain prior to modification did not comprise said nucleic acid sequence or did not comprise said *Lactococcus* CRISPR spacer, or said *Lactococcus* CRISPR repeat or said *Lactococcus* CRISPR array.

As used herein, "recombinant" used in reference to a cell, nucleic acid, or protein, refers to a cell, nucleic acid, or protein modified by the introduction of a nucleic acid or protein (either native or heterologous) using a vector (e.g. a plasmid), or is derived from a cell so modified. Thus, a "recombinant strain of bacteria" refers to a bacterial strain that has been modified by using a vector (e.g. a plasmid) to introduce of a nucleic acid (e.g., a CRISPR spacer sequence) or protein.

As used herein, the term "vector" refers to any nucleic acid molecule into which another nucleic acid molecule (e.g., a CRISPR repeat-spacer unit sequence) can be inserted and which can be introduced into and replicate within cells. Thus, the term refers to any nucleic acid construct (and, if necessary, any associated delivery system) capable of use for transferring of genetic material between different host cells. Many prokaryotic vectors are commercially available for the production of recombinant strains of bacteria. Selection of appropriate vectors is within the knowledge of those having skill in the art. It will be understood that the term vector may encompass bacteriophage. In some embodiments the vector may be a plasmid.

As used herein, the term "plasmid" refers to a circular double-stranded (ds) DNA construct that can be used as a vector for introducing DNA into a cell. Plasmids act as extrachromosomal self-replicating genetic element in many bacteria and some eukaryotes. In some embodiments, one or more plasmids can be integrated into the genome of the host cell into which it is introduced.

As used herein, "host," "host cell," or "host strain" refer to a cell that can replicate and/or express a DNA sequence introduced into the cell. In some embodiments the host cell is a lactic acid bacteria, such as a bacterial cell selected from *Bifidobacterium* species, a *Brevibacterium* species, a *Propionibacterium* species, a *Lactococcus* species, a *Streptococcus* species, a *Lactobacillus* species including the *Enterococcus* species, *Pediococcus* species, a *Leuconostoc* species and *Oenococcus* species. Suitable species include, but are not limited to *Lactococcus lactis*, including *Lactococcus lactis* subsp. *lactis* and *Lactococcus lactis* subsp. *cremoris*, *Lactococcus lactis* subsp. *cremoris*, *Leuconostoc* sp., *Lactococcus lactis* subsp. *lactis* biovar, *Streptococcus thermophilus*, *Lactobacillus delbrueckii* subsp. *bulgaricus* and *Lactobacillus helveticus*, *Bifidobacterium lactis*, *Lactobacillus acidophilus*, *Lactobacillus casei*. In some embodiments of the present invention, the host cells are *Lactococcus* cells, preferably *Lactococcus chungangensis*, *Lactococcus fujiensis*, *Lactococcus garvieae*, *Lactococcus lactis*, *Lactococcus lactis* subsp. *cremoris*, *Lactococcus lactis* subsp. *hordniae*, *Lactococcus lactis* subsp. *lactis*, *Lactococcus lactis* subsp. *tructae*, *Lactococcus piscium*, *Lactococcus plantarum*, *Lactococcus raffinolactis*.

In a most preferred embodiment the cell is a *Lactococcus lactis* cell.

As used herein, the term "corresponding parent strain" refers to the strain from which a recombinant strain is derived (e.g., the originating and/or wild-type strain). In some embodiments, the corresponding parent strain can be a strain that itself has been engineered or modified.

As used herein, "homologous sequence" refers to a nucleotide or polypeptide sequence having at least about 60%, at least about 70%, at least about 80%, at least about 85%, at least about 88%, at least about 90%, at least about 92%, at least about 94%, at least about 95%, at least about 96%, at least about 97%, at least about 98%, at least about 99%, or even greater sequence identity to a subject nucleotide or amino acid sequence when optimally aligned for comparison. In some embodiments, homologous sequences have between about 80% and 100% sequence identity, in some embodiments between about 90% and 100% sequence identity, and in some embodiments, between about 95% and 100% sequence identity.

The term "homologue" or "homologous sequence" means an entity having a certain homology with the subject sequences. As used herein, the term "homology" can be equated with "identity" or "similarity".

Sequence similarity can be determined using standard techniques known in the art (see e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, Wis.); and Devereux et al., 1984]). Useful algorithms for determining sequence homology include: PILEUP and BLAST (Altschul et al., 1990); and Karlin and Altschul 1993). PILEUP uses a simplification of the progressive alignment method of Feng and Doolittle (1987). The method is similar to that described by Higgins and Sharp (1989). Useful PILEUP parameters including a default gap weight of 3.00, a default gap length weight of 0.10, and weighted end gaps.

A particularly useful BLAST program is the WU-BLAST-2 program (see, Altschul and Gish, 1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. An amino acid sequence % identity value is determined by the number of matching identical residues divided by the total number of residues of the "longer" sequence in the aligned region. The longer sequence is the one having the most actual residues in the aligned region (gaps introduced by WU-Blast-2 to maximize the alignment score are ignored).

Suitably, the degree of identity or similarity with regard to a sequence is determined over at least 5 contiguous amino acids or nucleotides, determined over at least 10 contiguous amino acids or nucleotides, over at least 15 contiguous amino acids or nucleotides, over at least 20 contiguous amino acids or nucleotides, over at least 30 contiguous amino acids or nucleotides, over at least 40 contiguous amino acids or nucleotides, over at least 50 contiguous amino acids or nucleotides, or over at least 60 contiguous amino acids or nucleotides.

Suitably the degree of identity or similarity is determined using over the full length of the sequences taught herein.

As used herein, the term "hybridization" refers to the process by which a nucleic acid strand binds with another strand through complementary (e.g., Watson-Crick) base pairing between the strands.

As used herein, "selectively hybridizable" refers to two nucleic acids having sequences that specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° C. below the Tm of the probe); "high stringency" at about 5-10° C. below the Tm; "intermediate stringency" at about 10° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, the term "introducing" (and in past tense, "introduced") used in the context of "introducing a nucleic acid sequence into a cell," refers to any method suitable for transferring the nucleic acid sequence into the cell, including but not limited to conjugation, transformation including electroporation, nuclear microinjection, transfection, (e.g., lipofection mediated and DEAE-Dextrin mediated transfection), incubation with calcium phosphate DNA precipitate, high velocity bombardment with DNA-coated microprojectiles, *Agrobacterium* mediated transformation, transduction, natural or artificial competence, and protoplast fusion.

As used herein, the terms "transforming" and "transform" refer to any suitable means of introducing a nucleic acid comprising a CRISPR/Cas region or portion thereof into a cell. Such methods include, but are not limited to natural competence or induced competence using chemical or mechanical (electroporation) means. This term also includes conjugation which is a specific method of natural DNA exchange requiring physical cell-to-cell contact and transduction which is the introduction of DNA via a bacteriophage infection which is also a natural method of DNA exchange. Further included within this definition is the use of a transposable element, comprising a CRISPR/Cas region or portion thereof.

In various embodiments of the present invention, an exogenous nucleic acid (e.g., a construct or vector) comprising a CRISPR array sequence or at least a portion thereof are introduced into cells of a bacterial strain. Methods of transforming bacterial cells with nucleic acids resulting in integration into the genome via e.g., homologous recombination are well documented in the art, for example see Sambrook et al (1989) and Ausubel et al., (1995). Transformed cells may be cultured under conditions well-known for the replication and/or expression of an integrated nucleic acid sequence in a bacterium.

As used herein "an incoming sequence" refers to a DNA sequence that is being introduced into a host cell. The incoming sequence can be a DNA construct, can be a CRISPR sequence, can encode one or more proteins of interest (e.g., a recombinant version of a native protein), and can include flanking sequences such as a promoter and terminator around a protein of interest. As used herein, a "flanking sequence" or "flanking region" refers to any sequence that is either upstream or downstream of the sequence being discussed (e.g., any spacer has repeats as flanking sequences). In some embodiments, a flanking sequence is present on only a single side (either 3' or 5'), and in other embodiments, it is on each side of the sequence being flanked.

As used herein, the term "integrated" used in reference to a nucleic acid sequence means incorporated into the chromosomal DNA of a host cell. In one embodiment of the present invention, a recombinant CRISPR spacer sequence native to a bacterial species is inserted in a plasmid, used to transform a bacterial cell that does not have that spacer in its endogenous CRISPR loci genome, and the spacer is integrated into the transformed cell's genomic DNA.

Functional Combination

In some embodiments a given *Lactococcal cas* gene or protein or set of *Lactococcal cas* genes or proteins is always associated with a given *Lactoccocal* repeated sequence within a particular CRISPR locus. Hence in some embodiments a cas gene(s) or protein(s) and the repeated sequence form a functional pair.

Accordingly, particular combinations of one or more *Lactococcus cas* genes or proteins and one or more, preferably, two or more *Lactococcus* CRISPR repeats may be used in order for a CRISPR spacer to confer resistance against a target nucleic acid or transcription product thereof in a cell (e.g. a recipient cell).

In the context of the *Lactococcus* CRISPR repeat-cas gene or protein combination described herein, the term "functional" means that the combination is able to confer resistance to a target nucleic acid or a transcription product thereof when used together with a CRISPR spacer which at least a portion of which aligns with or is homologous to a target nucleic acid or transcription product thereof.

As used herein the term "functional CRISPR repeat-cas combination" and "functional CRISPR repeat-cas gene combination" includes a functional combination in which cas is a *Lactococcus cas* gene or a *Lactococcus* Cas protein.

Suitably, the one or more *Lactococcus cas* genes or proteins and/or the one or more, preferably, two or more, *Lactococcus* CRISPR repeats are or are derivable (preferably, derived) from the same cell (e.g. the same recipient cell).

General Methods and Embodiments of the Inventions

In some aspects, the present invention relies on routine techniques and methods used in the field of genetic engineering and molecular biology. The following resources include descriptions of general methodology useful in accordance with the invention: Sambrook et al. (1989), Kreigler (1990), and Ausubel et al. (1995). These general references provide definitions and methods known to those in the art. However, it is not intended that the present invention be limited to any particular methods, protocols, and reagents described, as these may vary.

Various methods for identifying CRISPR loci are known in the art. For example, Jansen et al. (2002) describe a computer-based approach in which nucleotide sequences are searched for CRISPR motifs using the PATSCAN program at the server of the Mathematics and Computer Science Division at the Argonne National Laboratory, Argonne, Ill., USA (see e.g., Jansen et al., 2002; Jansen et al., 2002). An exemplary algorithm that can be used for identifying CRISPR motifs was p1=a . . . b e . . . dpi c . . . dpi c . . . dpi, where a and b were the lower and upper size limit of the repeat and p1 and c and d were the lower and upper size limit of the spacer sequences. The values of a, b, c and d may be varied from about 15 to about 70 by increments of about 5 bp. In some embodiments, CRISPR loci are identified using dotplots (Dotter, Sonnhammer and Durbin, 1995) and other computer program. (e.g. CRISPRFinder, Grissa et al, 2007; CRISPR Recognition Tool, Bland et al., 2007; PILER-CR, Edgar, 2007).

Any suitable method known in the art finds use in analyzing sequence similarity. For example, analysis may be performed using NCBI BLAST with a microbial genomes database and GenBank, as known in the art. In addition, nucleotide sequences, including those provided herein are included in databases (e.g., GenBank or the JGI genome website). As used herein, "upstream" means in the 5' direction and "downstream" means in the 3' direction.

In additional embodiments, the methods of the present invention utilize amplification procedures (see e.g., Mojica et al., 2005; and Pourcel et al., 2005). Amplification of the desired region of DNA may be achieved by any method known in the art, including polymerase chain reaction (PCR). "Amplification" refers to the production of additional copies of a nucleic acid sequence. This is generally carried out using PCR technologies well known in the art. The "polymerase chain reaction" ("PCR") is well-known to those in the art. In the present invention, oligonucleotide primers are designed for use in PCR reactions to amplify all or part of a CRISPR array.

The CRISPR array is a distinct class of interspersed short sequence repeats (SSRs) that were first recognized in *E. coli* (Ishino et al., 1987; and Nakata et al., 1989). Similar interspersed SSRs have been identified in *Haloferax mediterranei, Streptococcus pyogenes, Anabaena*, and *Mycobacterium tuberculosis* (Groenen et al. 1993; Hoe et al., 1999; Masepohl et al., 1996; Mojica et al., 1995). The CRISPR loci differ from other SSRs by the structure of the repeats, which have been termed short regularly spaced repeats (SRSRs) (Jansen et al., 2002; and Mojica et al., 2000). The repeats are short elements that occur in clusters that are always regularly spaced by unique intervening sequences with a constant length (Mojica et al., 2000). Although the repeat sequences are highly conserved between strains, the number of interspersed repeats and the sequences of the spacer regions differ from strain to strain (van Embden et al., 2000).

CRISPR loci consist of short and highly conserved partially palindromic DNA repeats typically of 23 to 47 bp, containing inner and terminal inverted repeats of up to 11 bp. These repeats have been reported to occur from 1 to 375 times. Although isolated elements have been detected, they are generally arranged in clusters (up to about 20 or more per genome) of repeated units spaced by unique intervening 21-72 by sequences. To date, up to 20 distinct CRISPR loci have been found within a single chromosome.

CRISPRs are generally homogenous within a given genome with most of them being identical. However, there are examples of heterogeneity in, for example, the Archaea (Mojica et al., 2000).

Although the biological function of CRISPR loci is unknown, some hypotheses have been proposed. For example, it has been proposed that they may be involved in the attachment of the chromosome to a cellular structure, or in the chromosome replication and replicon partitioning (Jansen et al., 2002; Jansen et al., 2002; and Pourcel et al., 2005). Mojica et al. (2005]) hypothesize that CRISPR may be involved in conferring specific immunity against foreign DNA and Pourcel et al. (2005) hypothesize that CRISPRs are structures that are able to take up pieces of foreign DNA as part of a defense mechanism. Bolotin et al. (2005) suggest that the CRISPR spacer elements are the traces of past invasions by extrachromosomal elements, and hypothesize that they provide a cell with immunity against phage infection, and more generally foreign DNA expression, by coding an anti-sense RNA. Bolotin et al. (2005) also suggest that cas genes are necessary for CRISPR formation. However, it is not intended that the present invention be limited to any particular mechanism, function, theory, nor means of action.

Development of Phage-Resistant Strains and Starter Cultures

Importantly, the present invention provides methods and compositions for the development of phage-resistant strains and starter cultures. In some embodiments, a parental strain "A" is exposed to phage "P" and a phage resistant variant (Variant "A1.0") selected. Variant A1.0 is analyzed (for example by PCR, and/or DNA sequencing) to confirm the presence of an additional inserted spacer within a CRISPR array. The nucleotide sequence of the additional spacer (Spacer Sp1.0) is then determined. Typically, spacer Sp1.0 is a fragment of approximately 30 nucleotides in size from the phage P, and gives resistance to phage P and related phages ("related phages" are those containing the sequence of the spacer in their genomes, and define a family of phages).

Independently from the first phage exposure, the same parental strain A is exposed to the same phage P and a second phage resistant variant (Variant A2.0) is selected. Variant A2.0 is selected in order to also have an additional spacer inserted (Spacer Sp2.0) within a CRISPR array but with the sequence of spacer Sp2.0 being different from that of spacer Sp1.0. Typically, spacer Sp2.0 is a fragment of approximately 30 nucleotides in size from the phage P, and gives resistance to phage P and related phages. Similarly, in some embodiments, variant A3.0 to variant Ax.0 are generated through the exposure of the same strain A to the same phage P. All the "A" variants are selected in order to also have an additional spacer inserted (Spacer Sp3.0 to Spx.0) within a CRISPR array but with the sequence of all the "Sp" spacers being different from each of the others. Typically, "Sp" spacers are fragments of approximately 30 nucleotides in size from the phage P, and all give resistance to phage P and related phages.

Although these variants are useful, they are limited in terms of the scope of their resistance. Thus, in some embodiments, it is advantageous to develop second level phage resistant strains. Indeed, it is advantageous to further develop these phage resistant variants by increasing and expanding their resistance to phages. Typically, it can be estimated that the level of resistance will be approximately that of a single mutation occurring within the phage genome within the sequence corresponding to the spacer (i.e., roughly E-04 to E-06). Consequently, phage resistant strains that accumulate different spacers within the CRISPR array have an increased level of resistance to the phage containing the sequence of these spacers within their genome (i.e., since multiple single mutations need to occur within the phage genome).

In some embodiments, the second level variants are produced by isolating a mutated phage through exposure of variant A1.0 to phage P. Typically, this mutated phage (phage P1.0) has a mutation (deletion, point mutation, etc.) in its genome within the region containing the sequence of spacer Sp1.0. Variant A1.0 is sensitive to phage P1.0. Then, variant A1.0 is exposed to phage P1.0 and a phage resistant variant (Variant A1.1) selected. Variant A1.1 is also selected such that it has an additional spacer inserted (Spacer Sp1.1) within a CRISPR array but with the sequence of spacer Sp1.1 being different from that of spacers Sp1.0, Sp2.0 to Spx.0. Typically, spacer Sp1.1 is a fragment of approximately 30 nucleotides in size from the phage P1.0, and will give resistance to phage P1.0 and related phages. Variant A1.1 is resistant to phage P1.0 and preferably, has an increased resistance to phage P because of the accumulation of spacer Sp1.0 and Sp1.1.

In additional embodiments, a newly mutated phage (phage P1.1) is generated through exposure of variant A1.1 to phage P1.0. Then, upon exposure of variant A1.1 to phage P1.1 a new variant A1.2 is obtained that contains one new additional spacer (Sp1.2). This spacer gives resistance to phage P1.1 and preferably increases the resistance to phage P1.0 and P (i.e., due to the accumulation of spacers Sp1.0, Sp1.1, Sp1.2). In yet additional embodiments, different spacers (e.g., 2, 3 or 4) are iteratively accumulated within strain A through variant A1, then variant A1.1, then variant A1.2, etc to obtain a variant highly resistant to phages (variant A1.n). In still further embodiments, additional different spacers can be accumulated in the same strain through variant A2, then variant A2.1, then variant A2.2, etc to generate another variant of strain A highly resistant to phages (variant A2.n) in parallel. The same strategy finds use with variants A3.0 to Ax.0

In some embodiments, strains that are resistant to more than one family of phages are provided. The lactococcal CRISPR content is shown to confer resistance, as directed by spacer content towards at least three lactococcal phage types. As a given strain can be sensitive to more than one family of phages, in some embodiments, it is desired to enlarge the strain resistance to multiple phage families by introducing additional spacer(s) within a CRISPR array originating from the other families of phages. For example, phages P, Q, and R are representative phages from three families of phages able to infect strain A. Using the method outlined above and herein, variants resistant to all three phage families are produced. In some embodiments, phage P is used to generate variant $A1^P$ (containing spacer Sp1) that is resistant to phage P. Then, variant $A1^P$ is exposed to phage Q and a phage resistant variant (Variant $A1^{Pq}$) is selected. Variant $A1^{Pq}$ has one additional spacer (Sq1) inserted within a CRISPR array. Typically, spacer Sq1 is a fragment of approximately 30 nucleotides in size from the phage Q, and gives resistance to phage Q and related phages. Variant $A1^{Pq}$ is resistant to both P and Q phages. Next, variant $A1^{Pq}$ is exposed to phage R and a phage resistant variant (Variant $A1^{Pqr}$) is selected. Variant $A1^{Pqr}$ has a third additional spacer (Sr1) inserted within a CRISPR array. Typically, Sr1 is a fragment of approximately 30 nucleotides in size from the phage R, and also gives resistance to phage R and related phages. Variant $A1^{Pqr}$ is resistant to all three phages. In some particularly preferred embodiments, the variant is also resistant to related phages.

In additional embodiments, the above methods are used in combination to produce increased and expanded resistance to phages. In some particularly preferred embodiments, these variants have high resistances to multiple phage families. In still further embodiments, strains are produced that are resistant to particular phages or families of phages that are problematic in particular factories and/or fermenters.

In some embodiments, a strain containing the CRISPR-Cas locus serves as a source of CRISPR-Cas to transfer to a phage sensitive parental strain "A". Phage resistance is conferred upon the variant strain A1.0 if in the CRISPR there is a spacer or spacers with sufficient identity against the recipient strain's homologous phage "P". Although these variants are useful, they are limited in terms of the scope of their resistance. Thus, in some embodiments, the CRISPR can be directly modified by the addition of one or more spacers specifically designed with identity to a target phage or phage family and therefore conferring resistance to a specific phages or family of phages. In this manner, the CRISPR-Cas can be further directed by insertion of additional spacers that target specific phage and/or phage-families in order to develop phage resistant variants by increasing and expanding their resistance to phages. Typically, it can be estimated that the level of resistance will be approximately that of a single mutation occurring within the phage genome within the sequence corresponding to the spacer (i.e., roughly E-04 to E-06). Consequently, phage resistant strains that have been engineered to contain different spacers within the CRISPR locus have an increased level of resistance to the phage containing the sequence of these spacers within their genome (i.e., since multiple single mutations need to occur within the phage genome). In some embodiments, the second level variants are produced by isolating a mutated phage through exposure of variant A1.0 to phage P. Typically, this mutated phage (phage P1.0) has a mutation (deletion, point mutation, etc.) in its genome within the region containing the sequence of spacer Sp1.0. Variant A1.0 is sensitive to phage P1.0. A synthetic spacer can then be designed to phage P1.0, either targeting spacer Sp1.0 directly (spacer Sp 1.1) or another region (spacer Sp2.0) which when inserted into the CRISPR can direct resistance to phage P.1.0

In some embodiments, strains that are resistant to more than one family of phages are provided. The lactococcal CRISPR content is shown to confer resistance, as directed by spacer content towards at least three lactococcal phage types. As a given strain can be sensitive to more than one family of phage, in some embodiments, it is desired to enlarge the strain resistance to multiple phage families by introducing additional spacer(s) within a CRISPR locus originating from the other families of phages. For example, phages P, Q, and R are representative phages from three families of phages able to infect strain A. Using the method outlined above and herein, variants resistant to all three phage families are produced. Specifically designed spacers against phages P, Q, and R can be synthesized and inserted into the CRISPR to direct phage resistance.

CRISPR-Mediated Immunity and Applications for Phage-Resistant Strains

Advantageously, the application of one or more CRISPR loci, two or more CRISPR repeats, one or more cas genes or proteins and/or one or more CRISPR spacers in genetic engineering provides means to produce resistant or sensitive variants of cells for use within a wide variety of applications in the biotechnology industry.

As discussed in greater detail below, phages are natural parasites of bacteria that may develop during fermentation. Upon infection by phages, bacteria are killed, which impairs the fermentation process. In dairy fermentation, these phage infections often have major economic impacts, ranging from a reduced quality of the fermented product up to the complete loss of the product.

To overcome phage problems, starter culture companies have developed various strategies. Traditional starter culture programs have depended on phage defence rotation strategies (PDRS) to minimize failures due to phage attack (see e.g., Klaenhammer, 1984; Lawrence et al., 1976; and Whitehead and Hunter, 1947). These strategies rely on multiple genetically unrelated strains that are likely to present different spectrum of phage sensitivity (i.e., different lysotypes). When a phage appears during a fermentation process using a defined strain, a strain which is ideally of a different lysotype (i.e., with a different sensitivity pattern to phages) is use in replacement for the fermentation. History has proven, however, that it is difficult to identify sufficient numbers of different lysotypes to successfully utilize these strategies. Indeed, many strains of industrial interest present rare functional traits (e.g., fast acidifying, texturing, flavor producing, and/or antibacterial producing *Lactococcus lactis*). In addition, not all of the strains present appropriate traits for being produced as starter cultures. Further, because of their rareness and the increase of the size of dairy factories, these strains are intensively used.

There are additional problems with traditional starter culture rotation strategies. Although some stains are not attacked by existing phages when introduced, phage often eventually appear due to phage mutation, modification, and build-up that attack the newly introduced strain (see e.g., Heap and Lawrence, 1976; Limsowtin and Terzaghi, 1976;

Pearce, 1978; and Sanders and Klaenhammer, 1980). Moreover, in many cases, the longevity and starter activity of complex strain rotations is unpredictable and often leads to early failure (see e.g., Limsowtin et al., 1978; and Thunell et al., 1981). Furthermore, prolonged rotations involving numerous strains increase the level and diversity of phage contaminating the plant (see e.g., Heap and Lawrence, 1981; Lawrence et al., 1978; and Thunell et al., 1981).

In order to fight phage proliferation, traditional starter culture programs have depended on the use of strains presenting the same or similar technological functionalities but different phage sensitivities. The strains are used in rotation to perform successive fermentation. These programs traditionally rely on multiple genetically unrelated strains that consequently presents different spectrum of phage sensitivity (lysotype). Alternative approaches (see e.g., U.S. Pat. No. 5,593,885) utilizes starter culture programs based on the use of sets of isogenic strains that present different phage sensitivity, instead of genetically unrelated strains presenting different lysotypes. The term "set of isogenic strains" as used herein defines strains that are identical from a chromosomal point of view but that each differs by the presence of one or more phage resistance mechanisms that are plasmid-borne. In such starter culture rotation program, when a phage appears during a fermentation process using a defined strain, a strain which is ideally of a different lysotype (i.e., with a different spectrum of sensitivity to phages) is used in replacement for the fermentation. Due to this different lysotype, the second strain is not affected by the phages that stay dormant in the environment. Most of the population of dormant phages are then be washed out by successive fermentation and sanitation, and eradicated by the time the first strain is used again for the fermentation, if the system works as intended.

The present invention provides improved methods and compositions suitable for addressing these problems in the fermentation industry. Indeed, the present invention provides methods and compositions for the fermentation industry, and in particular the dairy industry with a selection of strains suitable to fulfil the needs of phage defence rotation strategies. In addition, the present invention provides methods and compositions suitable to customize strains having lysotypes that are adapted to a particular phage environment. In particular, the present invention provides methods and compositions suitable for directing the evolution of a given strain to various lysotypes, in order to produce strains that differ from each other only by their spectrum of phage sensitivity (lysotype). This difference of lysotype is a function of the CRISPR-cas system, as described herein. In some preferred embodiments, different lysotypes are obtained through the "modulation" of phage resistance. In some particularly preferred embodiments, although the lysotypes are different, strains of this type have identical metabolism (e.g., of carbon, nitrogen, etc.) and thus identical functionalities (e.g., acidification, flavour, texture, etc.). This provides means for amplifying the construction of starter rotation. In addition, industrial processability of the phage resistant strain are identical (e.g., nutrition needs, resistance to processing operation, etc.), thus reducing the need of development of specific production processes. Indeed, the present invention provides methods and compositions suitable for minimizing fermentation failures due to phage attack. In some embodiments, methods and compositions are provided for the production of highly phage resistant starter cultures, by the association of multiple phage resistant strains differing by their lysotype. In some alternative embodiments, methods and compositions are provided to produce starter cultures with strictly identical industrial functionalities to be used in rotation dairy fermentation. In further embodiments, methods and compositions are provided that are suitable to replace existing starters by preventing frequent phage attacks in dairy plants, by introducing a new bacterial strain that is resistant to the phages involved in these phage attack. In some embodiments, these methods and compositions are used iteratively, in order to combat sequential phage attacks.

In some additional embodiments, the starter culture is a mixed bacterial culture. In some particularly preferred embodiments, the starter comprises equal amounts of multiple (i.e., at least 2) phage resistant variants that only differ in their CRISPRs and their sensitivity to phages. In some embodiments, these variants are of the first level of phage resistant variants (e.g., variants A1.0 plus A2.0, as described above). In some preferred embodiments, the variants are selected from those in the second level of phage resistant variants (e.g., variants A1.4 plus A2.4, as described above). In some particularly preferred embodiments, the variants are selected among the third level of phage resistant variants. In such mixed bacterial cultures, when one of the variants is attacked by a given phage the other variants are not be attacked by the phage, due to their different phage sensitivities and the fermentation is not adversely affected.

In some further embodiments, a principal starter and a back-up starter are used. The principal starter is composed of a single strain. In some embodiments, this strain is of the first level of phage resistant variants, while in other preferred embodiments the strain is of the second level, and in still other more preferred embodiments, the strain is of the third level. In some preferred embodiments, the back-up starter is based on a phage resistant variant obtained independently from the same parental strain. This second phage resistant variant differs from the other variant by its CRISPRs and is of the first level of phage resistant variants, while in other preferred embodiments the strain is of the second level, and in still other more preferred embodiments, the strain is of the third level. For example, in some embodiments, the principal starter is made of variant A1.4 and the back-up starter is made of strain A2.4. Upon first appearance of a phage during fermentation with the principal starter, this starter is discarded and replaced by the back-up starter. In some more preferred embodiments, a third starter is also prepared as the back-up starter that will serve as a back-up for the backup. In some preferred embodiments, the starters are each made of multiply phage-resistant variants.

In yet further embodiments, the present invention provides methods and compositions suitable in rotation strategies. In some embodiments, instead of discarding the starter often attacked by phages, the starters are used in a cyclic way even if phage attack is observed. This strategy limits the number of starters to be developed. In some particularly preferred embodiments, the starters are each made of multiple phage resistant strains instead of a single one. This provides increased robustness to emerging phage. In still further embodiments, customized starters are provided. In some preferred embodiments, the phage resistant variants are produced to specifically combat phages that are present in a given fermentation plant or facility.

Suitably, the variant bacterial cell or host bacterial cell may be selected from a lactic acid bacteria species, a *Bifidobacterium* species, a *Brevibacterium* species, a *Propionibacterium* species, a *Lactococcus* species, a *Streptococcus* species, a *Lactobacillus* species including the *Enterococcus* species, *Pediococcus* species, a *Leuconostoc* species and *Oenococcus* species.

Suitable species include, but are not limited to *Lactococcus lactis*, including *Lactococcus lactis* subsp. *lactis* and *Lactococcus lactis* subsp. *cremoris*, *Lactococcus lactis* subsp. *cremoris*, *Leuconostoc* sp., *Lactococcus lactis* subsp. *lactis biovar*, *Streptococcus thermophilus*, *Lactobacillus delbrueckii* subsp. *bulgaricus* and *Lactobacillus helveticus*, *Bifidobacterium lactis*, *Lactobacillus acidophilus*, *Lactobacillus casei*.

The cell in which resistance is to be modulated may be a bacterial cell used for the fermentation of meat (including beef, pork, and poultry) including, but not limited to, lactic acid bacteria, *Pediococcus cerevisiae*, *Lactobacillus plantarum*, *Lactobacillus brevis*, *Micrococcus* species, *Lactobacillus sakei*, *Lactobacillus curvatus*, *Pediococcus pentosaceus*, *Staphylococcus xylosus* and *Staphylococcus vitulinus* and mixtures thereof (Food Biotechnology, 538-39 (D. Knorr Ed. 1987); C. Pederson, Microbiology of Fermented Foods, 210-34 (2d ed. 1979); U.S. Pat. No. 2,225,783).

The cell in which resistance is to be modulated may be a bacterial cell used for the fermentation of vegetables (e.g., carrots, cucumbers, tomatoes, peppers, and cabbage) including, but not limited to, *Lactobacillus plantatum*, *Lactobacillus brevis*, *Leuconostoc mesenteroides*, *Pediococcus pentosaceus*, and mixtures thereof (Food Biotechnology, 540 (D. Knorr Ed. 1987); C. Pederson, Microbiology of Fermented Foods, 153-209 (2d ed. 1979); U.S. Pat. No. 3,024,116; U.S. Pat. No. 3,403,032; U.S. Pat. No. 3,932,674; and U.S. Pat. No. 3,897,307).

The cell in which resistance is to be modulated may be a bacterial cell used for the fermentation of dough formed from cereals (e.g., wheat, rye, rice, oats, barley, and corn).

The cell in which resistance is to be modulated may be a bacterial cell used for the production of wine. Typically, this is achieved by the fermentation of fruit juice, typically grape juice.

The cell in which resistance is to be modulated may be a bacterial cell used for the fermentation of milk to produce cheese—such as *Lactobacillus delbrueckii* subsp. *bulgaricus*, *Lactobacillus helveticus*, *Streptococcus thermophilus*, *Lactococcus lactis* subsp. *lactis*, *Lactococcus lactis* subsp. *cremoris*, *Lactococcus lactis* subsp. *lactis biovar diacetylactis*, *Bifidobacteria* and *Enterococci* etc and mixtures thereof (Food Biotechnology, 530 (D. Knorr Ed. 1987); C. Pederson, Microbiology of Fermented Foods, 135-51 (2d ed. 1979)).

The cell in which resistance is to be modulated may be a bacterial cell used for the fermentation of egg—such as *Pediococcus pentosaceus*, *Lactobacillus plantarum*, and mixtures thereof (Food Biotechnology, 538-39 (D. Knorr Ed. 1987)).

The cell in which resistance is to be modulated may be a bacterium for use in cosmetic or pharmaceutical compositions. Such compositions may comprise a cell culture and/or labelled bacterium according to the present invention. Thus the labelled bacterium and/or a cell culture according to the present invention may be compatible in cosmetics or in pharmacy or in therapy. Thus in one embodiment the present invention provides a pharmaceutical composition comprising a variant bacterial cell according the present invention, or a cell culture according the present invention, or a host cell according to the present invention, and optionally a pharmaceutically acceptable diluent or excipient.

In one embodiment the variant bacteria or host cells are harvested (e.g. isolated from the production medium) between 5 to 24 hours after transformation.

In one embodiment the variant bacteria or host cells are concentrated, e.g. by centrifugation In one embodiment the variant bacteria or host cells or cell culture or bacterial culture are stored. Suitably they may be stored at 4° C. Suitably they may be stored in liquid, frozen or lyophilized form.

In one embodiment the variant bacteria or host cells or cell culture or bacterial culture may be packaged. The packaging is preferably suitable for distribution and storage of the variant bacteria or host cells or cell culture or bacterial culture.

Engineering Altered Resistance to Nucleic Acids Using Recombinant *L. lactis* CRISPR Sequences CRISPR loci have been shown to provide resistance in prokaryotes against incoming nucleic acids. For example, it has been shown that specific spacer sequences in CRISPR array confer or modify resistance in *S. thermophilus* strains against specific phage (see e.g., Barrangou et al., 2007). The general methods disclosed to engineer altered resistance in *S. thermophilus* strains to phage can be used to engineer altered resistance in other bacterial strains having CRISPR loci.

Methods for altering bacterial resistance to exogenous nucleic acids (e.g., phage) by adding, deleting, and/or modifying sequences in endogenous CRISPR loci found in the bacteria also are disclosed in e.g., Russell and Klaenhammer, (2001); and PCT publ. no. WO2007/025097 A2, published Mar. 1, 2007, which is hereby incorporated by reference herein. These methods can be used in the embodiments of the present invention.

Generally, the minimal genomic structure required to confer CRISPR associated resistance against a target nucleic acid (or expression product thereof) is at least one cas gene (or one Cas protein) and at least two CRISPR repeats flanking a spacer. Thus, in some embodiments, the present invention provides a method for altering (e.g., conferring or increasing) resistance of a cell against a target nucleic acid or a transcription product thereof, wherein the method comprises: (a) preparing a nucleic acid comprising at least one cas gene and at least two CRISPR repeats together with the CRISPR spacer, wherein the CRISPR spacer sequence is homologous to a target nucleic acid sequence (e.g., a conserved sequence essential to the function or survival of the organism); and (b) transforming a cell with said nucleic acid, whereby the transformed cell is rendered resistant to said target nucleic acid or transcription product thereof. In some embodiments, the method further comprises (c) contacting the transformed bacteria with the target nucleic acid; and (d) isolating transformed bacteria that exhibit altered resistance to the target nucleic acid.

Methods of transforming bacterial cells with nucleic acids comprising CRISPR sequences such that transformation results in integration into the genome (either chromosome or native plasmids) via e.g., homologous recombination are well documented in the art, for example see Sambrook et al (1989) and Ausubel et al., Current Protocols in Molecular Biology (1995), Transformed cells may be cultured under conditions well-known for the replication and/or expression of an integrated or plasmid-encoded nucleic acid sequence in a bacterium.

In some embodiments of the method, a CRISPR spacer previously has been identified that is associated with an organism's resistance to the target nucleic acid or a transcription product thereof. In such a situation, the method may be carried out using the known spacer sequence. In some embodiments of the present invention, the spacer sequence is selected from the group of *L. lactis* spacers consisting of SEQ ID NOs: 25-60.

In prokaryotes where the genome already comprises a CRISPR array and associated cas genes, CRISPR associated resistance can be altered by modifying the existing CRISPR sequences. In embodiments where the sequence of a resistance-associated CRISPR spacer is already known, the sequence of an existing CRISPR spacer in an organism can be modified so that it is homologous or identical to the resistance-associated CRISPR spacer. Alternatively, a repeat-spacer unit having the resistance-associated CRISPR spacer sequence can be inserted in the existing CRISPR array, thereby altering the resistance of the organism. In other embodiments, where it is desired to decrease resistance, a known resistance-associated CRISPR spacer can be modified or deleted (as a repeat-spacer unit) from the existing CRISPR array, thereby decreasing or completely removing the organism's resistance to the target nucleic acid.

The L. lactis locus includes the typical CRISPR elements required for phage resistance, including associated csm/cas genes, conserved repeats, and spacer sequences that exhibit homology to known phage sequences.

A homology analysis carried out on the DGCC7167 CRISPR spacer sequences identified a number of spacers that had significant homology to a known phage sequence (Table 3).

Based on the phage sequence homology of the CRISPR spacers, in some embodiments of the present invention these homologous spacer sequences may be used in the methods to engineer altered phage resistance in bacterial strains described herein.

The L. lactis CRISPR loci sequences disclosed herein provide a source of repeat and spacer sequences that can be used in the methods for engineering altered resistance in other bacterial strains. Additionally, knowledge of the L. lactis CRISPR array provides the necessary CRISPR array "platform" for engineering L. lactis and other lactococci. For example, CRISPR spacers from other organisms with known CRISPR-associated resistance characteristics may be inserted or otherwise engineered in the L. lactis CRISPR array.

In one embodiment, the sequences of the L. lactis locus and its associated csm/cas genes can be used in accordance with the above-described methods to alter resistance in a L. lactis strain against incoming nucleic acids, notably protection against phage attacks. In some embodiments, altered phage resistance is engineered in a bacteria with a CRISPR array by introducing (i.e., inserting using recombinant DNA techniques) a CRISPR spacer into the CRISPR array of the bacterial genome, wherein the CRISPR spacer has a sequence selected from the group consisting of SEQ ID NOs: 25-60.

In some embodiments of the various methods disclosed herein, altered phage resistance is engineered in a bacterial strain with a CRISPR array by introducing a CRISPR repeat-spacer unit into the CRISPR array of the bacterial genome. In such an embodiment, the repeat-spacer unit comprises a repeat sequence corresponding to SEQ ID NO: 24 or sequences which have at least 70%, 75%, 80%, 85%, 90%, 95%, 97%, 98% or 99% identity to SEQ ID No: 24, or a sequence which hybridises under high stringency to at least one of SEQ ID Nos:24, and the spacer sequence selected from SEQ ID NOs: 25-60; or sequences which have at least 70%, 75%, 80%, 85%, 90%, 95%, 97%, 98% or 99% identity to at least one of SEQ ID Nos: 25-60, or a sequence which hybridizes under high stringency to at least one of SEQ ID Nos: 25-60.

In some embodiments of the above-described methods, the L. lactis CRISPR spacer sequence introduced into the existing CRISPR array of a bacterium comprises a sequence having at least 50% identity, or at least 60% identity, or at least 63% identity to a target nucleic sequence of the phage to which resistance is desired. In some embodiments, the target nucleic acid sequence is conserved in the phage, and in some embodiments comprises a sequence essential to phage survival.

In some embodiments a portion of the L. lactis CRISPR spacer sequence may be a sequence having at least 70% identity, or at least 80% identity or at least 90% identity or at least 100% identity to a target nucleic sequence of the phage to which resistance in desired. In some embodiments, the target nucleic acid sequence is conserved in the phage, and in some embodiments comprises a sequence essential to phage survival.

In the various embodiments of the methods disclosed herein for altering resistance in cells, the engineering of a CRISPR array in the cell for which altered resistance is desired may include, but is not limited to, adding (e.g. inserting), deleting (e.g., removing), or modifying (e.g., mutating) sequence of CRISPR spacers in the cell such that the CRISPR array of the cell has homology (e.g., increased homology after the engineering) to at least one CRISPR spacer of an organism with a known CRISPR-associated resistance (e.g., a L. lactis cell). Such engineering can result in a cell that was substantially sensitive to a target nucleic acid or a transcription product thereof being substantially resistant to the target nucleic acid or a transcription product thereof.

In some embodiments, the invention provides a method for altering the resistance of a cell against a target nucleic acid, wherein the cell comprises a CRISPR array and associated csm/cas genes, said method comprising: (a) identifying one or more resistance-associated CRISPR spacers in an organism resistant to the target nucleic acid; and (b) modifying the sequence of at least one spacer in the CRISPR array of the cell such that its sequence is homologous or identical to the sequence of the resistance-associated CRISPR spacer. In embodiments of the present invention, the method is carried out wherein the organism resistant to the target nucleic acid is a Lactococcus (e.g., L. lactis) and the resistance-associated CRISPR spacers are selected from the CRISPR spacers having SEQ ID NOs: 25-60.

In some embodiments, the methods provide for decreasing or reducing the resistance of a cell comprising at least one or more csm/cas genes or proteins and one or more, preferably, two or more CRISPR repeats against a target nucleic acid or a transcription product thereof. According to this embodiment, the method comprises the steps of: (a) identifying one or more CRISPR spacers in an organism that is substantially resistant to the target nucleic acid or a transcription product thereof; and (b) modifying the sequence of one or more CRISPR spacer(s) in the cell such that the CRISPR spacer(s) has a reduced degree of homology to the CRISPR spacer(s) in the organism.

The various embodiments of the methods for engineering altered resistance to a target nucleic acid disclosed herein, can be used in a number of applications: (i) engineering resistance to phage; (ii) engineering resistance to plasmid transfer; (iii) engineering resistance to mobile genetic elements; (iv) engineering resistance to antibiotic resistance genes; (v) engineering resistance to genes encoding virulence factors; and (vii) engineering resistance to novel sequences. The various L. lactis CRISPR loci sequences and the associated repeat and spacer sequences disclosed herein provide a platform for engineering altered resistance in *L. lactis* and related lactococci with related CRISPR loci.

Generally, in embodiments for altering resistance to phage, particular CRISPR spacers derived from bacteriophage DNA are added within a CRISPR array of the bacterial cell so as to provide resistance against this particular bacteriophage and prevent phage attack. Additionally, particular regions within the phage genome (host specificity proteins) can be targeted that provide particular phage-host recognition, or that are highly conserved within phage DNA, such as sequences from helicase or primase genes, head and tail structural proteins, or proteins with conserved domains (e.g., helicase, holin, lysin, and others) or conserved sequences amongst important phage genes. Thus, knowledge of particular phage sequences can be used to modify existing CRISPR spacers to alter resistance to these particular phage.

In some embodiments, engineering altered resistance to plasmid transfer in a bacterial strain can be carried out in accordance to the methods disclosed herein. Particular CRISPR spacers derived from plasmid DNA are added within the existing CRISPR array so as to provide resistance against this particular plasmid, thus preventing transfer of foreign DNA into cells of the strain. In some embodiments, particular regions within the target plasmid DNA, such as sequences within the plasmid's origin of replication, are selected for addition to the CRISPR array so as to provide immunity against the plasmid DNA.

In some embodiments, methods for altering resistance to mobile genetic elements are carried out in the same way. CRISPR spacers derived from mobile genetic element DNA can be added within the existing CRISPR array of the bacterial strain so as to provide resistance against mobile genetic elements such as transposable elements and insertion sequences. Such engineered resistance can prevent transfer of foreign DNA and genetic drift in the engineered bacterial strain. Specifically, particular regions within transposons and insertion sequences can be targeted as to provide immunity against mobile genetic elements. For example, targets can include conjugative transposons (Tn916, Clewell et al., 1991), class II transposons (Tn501, Stanisich et al., 1977), or insertions sequences (IS26, Mollet et al., 1981).

In some embodiments, methods for altering resistance to antibiotic resistance genes are carried out by adding CRISPR spacers derived from antibiotic resistance encoding genes within an existing bacterial strain's CRISPR array. Such altered resistance can prevent transfer of genes conferring resistance to antibiotics into the bacterial host, thus reducing the risk of acquiring antibiotic resistance markers. For example, targets can include vanR, a gene conferring resistance to vancomycin, or tetR, a gene conferring resistance to tetracycline, or targeting beta-lactamase inhibitors.

In some embodiments, CRISPR spacer sequences derived from genes encoding virulence factors can be added within a bacterial CRISPR array as to provide resistance against the transfer of genes conferring virulence into the bacterium. For example, factors commonly contributing to virulence in microbial pathogens can be targeted, such as toxins, internalins and hemolysins, In some embodiments, novel spacer sequences can be synthesized de novo, engineered and integrated into a CRISPR array within a seleed bacterial host as to provide resistance to a particular identical and novel sequence present into an infecting DNA molecule.

Strain Detection, Strain Typing, and/or Strain Tracking Using *L. lactis* CRISPR Sequences In some embodiments of the present invention, the CRISPR array sequences and portions of these sequences (e.g., repeats, spacers, and combinations thereof) can be used for detecting, tracking, and/or typing the bacteria in which they are present. Methods for strain detection, typing, and tracking using CRISPR sequences that can be used in the embodiments of the present invention are disclosed in e.g., U.S. published application 2006/01990190 A1, published Sep. 7, 2006, which is hereby incorporated by reference herein.

The CRISPR array disclosed herein has been identified in *L lactis* subsp. *cremoris* DGCC7167.

In some embodiments, a strain is detected and/or distinguished from another strain (i.e., typed) by amplifying a portion of a CRISPR array sequence in the strain that has been determined to distinguish it. Methods for amplifying specific genomic sequences in bacteria are well-known in the art (e.g., PCR, LCR, isothermal methods). Generally, a CRISPR array or a portion thereof from a known source bacterium (e.g., the parent bacterium) and the unknown bacterium are amplified and/or sequenced using any suitable method known in the art. The determined sequences and/or the determined amplicons (e.g., based on size) are compared to determine if they are the same or different.

In some embodiments of the present invention, the CRISPR array or a portion thereof from the source (or known) bacterium and the unknown bacterium (e.g., the test sample) are compared by amplifying the CRISPR array or a portion thereof and comparing the characteristics of the amplicons (e.g., agarose gel electrophoresis analysis of amplicon size). In other embodiments of the present invention, a CRISPR array or a portion thereof from the known source bacterium and the unknown source bacterium are compared by sequencing the CRISPR array or a portion thereof from each and comparing the sequences.

In some embodiments of the present invention, strain detecting, typing, and/or tracking is carried out by a method comprising: (a) amplifying genomic DNA from a strain of interest using at least one primer pair, wherein the genomic DNA comprises at least a portion of a sequence of a CRISPR array; and (b) detecting an amplicon generated in step (a), whereby said detected amplicon indicates the strain type. In some embodiments, each primer of the pair is complementary to at least a portion of a sequence of a CRISPR array.

Typically, PCR is used to amplify the genomic DNA obtained from the strain of interest. Using the CRISPR sequences disclosed herein, or sequences found in published bacterial genomes, it is straightforward to determine distinguishing CRISPR sequences (e.g., that differ in number of repeats or spacers) and design PCR primer pairs that can be used to amplify the regions that contain these sequences.

In some embodiments, bacteria are compared by amplifying and then sequencing the CRISPR array or a portion thereof. For example both the 5' and 3' ends of the loci may be amplified and/or sequenced and are compared.

In some embodiments, one end (e.g., the 5' end) of the CRISPR arrays are compared. In yet other embodiments, at least the last CRISPR repeat at the 3' end of the CRISPR array and/or at least the last CRISPR spacer at the 3' end of the CRISPR array and/or at least the first CRISPR repeat at the 5' end of the CRISPR array and/or at least the first CRISPR spacer (e.g., the first CRISPR spacer core) at the 5' end of the CRISPR array are compared. In some embodiments, at least the first CRISPR repeat at the 5' end of the CRISPR array and/or at least the first CRISPR spacer (e.g., the first CRISPR spacer core) at the 5' end of the CRISPR array are compared. In some additional embodiments, at least the last CRISPR spacer (e.g., the last CRISPR spacer core) at the 3' end of the CRISPR array and/or at least the first CRISPR spacer (e.g., the first CRISPR spacer core) at the 5' end of the CRISPR array are compared. In some further embodiments, at least the first CRISPR spacer (e.g., the first CRISPR spacer core) at the 5' ends of the CRISPR arrays are compared.

In one embodiment of strain detecting, typing, and/or tracking, the distinguishing CRISPR feature is the number of repeat-spacer units found in the CRISPR array. That is, one strain may have 12 repeats and 11 spacers, and another strain may have only 8 repeats and 7 spacers. Amplification of the CRISPR regions of these two strains will result in PCR amplicons of greatly differing sizes. Detecting this amplicon and determining its size and how it differs from another strain provides one embodiment for strain typing.

Because CRISPR loci generally evolve by adding new repeat-spacer units to the 5' end of the repeat-spacer portion of the CRISPR array, in some embodiments a method for detecting or typing a newly evolved strain includes generating an amplicon that includes the 3' end of the CRISPR leader. Thus, in some embodiments, the method of strain typing comprises using a primer designed to hybridize to a sequence comprising the 3' end of the CRISPR leader. In one embodiment, the primer hybridizes to the sequence comprising the 3' end of the CRISPR leader and the 5' end of the first repeat.

In one embodiment, changes in a strain can be tracked by amplifying samples of the strain over time. Changes in the fast evolving CRISPR sequences will manifest as changes in the size of the detected amplicon. For example, if new repeat-pairs are added to the 5' end of the CRISPR region, this will result in an increase in the size of the largest amplicon detected for a strain.

In one embodiment, this method of strain detecting, typing and/or tracking can be used to detect man-made changes to a CRISPR, e.g., engineering a phage resistance by introduction of a new spacer into an existing CRISPR array. Thus, it is contemplated that the methods of strain detecting, typing and/or tracking can be used to monitor the strain tagging embodiments disclosed herein. For example, where a lactococcal strain is tagged with a CRISPR spacer following exposure to a phage, the incorporation of the new repeat-spacer unit can be monitored by the methods of strain detecting, typing and/or tracking described above.

Generally, in the strain detecting, typing, and tracking embodiments of the present invention, a PCR amplicon is generated using amplicons complementary to region of the CRISPR array sequences found in genomic samples from two L. lactis strains. A detected difference in the amplicons from the two samples (determined based on a difference in the sequence and/or size of the amplicons) is indicative of a difference in the number of repeat-spacer units present in the CRISPR loci from the two strains. Where the two Lactococcus samples are found to be identical, it can be concluded that they are the same type. Where the two samples include an archival sample of a strain and a sample prepared after the lactococcal strain has undergone many generations in an industrial process, the comparison between the two track whether the strain has undergone changes due to phage exposure or other treatments. Where one sample is a parent strain and the other is the same parent strain after exposure to a phage, the comparison can confirm if the strain has been tagged with a CRISPR spacer.

Strain Tagging Using *L. Lactis* CRISPR Sequences

In some embodiments the present invention provides methods of tagging bacterial strains using the CRISPR array sequences, or portions of these sequences (e.g., repeats, spacers, and combinations thereof). Methods for strain tagging with CRISPR sequences useful in the embodiments of the present invention are disclosed in e.g., U.S. published application 2008/0124725 A1, published May 29, 2008 which is hereby incorporated by reference herein.

Typically, in the strain tagging embodiments, a bacterial strain to be tagged is exposed to a phage and the infection induces the addition of a CRISPR sequence (e.g., a repeat-spacer unit) to the CRISPR array in the bacterial strain. This added repeat-spacer acts as a genetic tag (i.e., marker sequence) for that bacterial strain which can be detected using any of the well-known methods described above in the context of strain typing, detecting, and tracking (e.g., PCR, sequencing, immobilized probe hybridization).

Thus, in some embodiments the present invention provides a method for tagging a lactococcal strain comprising: exposing cells of a corresponding parent strain comprising at least a portion of a CRISPR array to at least one exogenous nucleic acid sequence, thereby producing a tagged bacterial cell with a CRISPR array comprising at least one more repeat-spacer unit than the corresponding parent strain cells.

In some embodiments, the present invention provides methods for tagging a bacterial strain comprising: (a) exposing a parent bacterial strain to a phage; (b) selecting a phage insensitive mutant; (c) comparing a CRISPR array or a portion thereof from the parent strain and the phage insensitive mutant strain; and (d) selecting a tagged bacterial strain comprising an additional repeat-spacer unit in the CRISPR array that is not present in the parent bacterial strain.

In alternative embodiments, the present invention provides methods for tagging the CRISPR array of a bacterial strain using recombinant DNA techniques as known in the art rather than exposure to phage. For example, in some embodiments, synthetic oligonucleotides are produced and used to transform parent bacteria to produce CRISPR tagged bacteria.

The *L. lactis* CRISPR array sequences disclosed herein provide a source of repeat and spacer sequences that can be used in the methods for tagging other bacterial strains. Additionally, the CRISPR array sequences disclosed herein provide a target CRISPR array that can be tagged with spacers from other sources. For example, CRISPR spacers from other organisms with may be inserted or otherwise engineered in the *L. lactis* CRISPR array. The knowledge of the CRISPR array sequence disclosed herein thereby provides the background for recognizing whether a strain has been tagged.

Thus, in some embodiments, the present invention provides a tagged bacterial strain, wherein the strain is not *L. lactis* and comprises a CRISPR locus comprising a *L. lactis* CRISPR spacer sequence selected from SEQ ID NOs: 25-60.

Biocontrol Phages

The present invention also provides methods and compositions for the development of phages as biocontrol agents. As indicated herein, bacteria can become resistant to phage attack by incorporating phage derived sequences (spacers) into an active CRISPR-Cas loci. Phage can escape this resistance by mutation within the genome sequence corresponding to the spacer or the CRISPR motif recognition sequence that corresponds to a given CRISPR-Cas system. Through iterative rounds of phage challenge to create host strain CRISPR-mediated phage resistant derivatives and isolation of phage escape mutants, the present invention provides phages that have been altered within CRISPR target sequences and/or putative CRISPR recognition sites that direct spacer insertion. Further, the present invention provides phages that have been synthetically designed such that the CRISPR motif sequence for a given CRISPR-Cas system has been eliminated. These "altered" phages, applied as a cocktail or in a "sequential rotation scheme" reduce the ability of target bacteria to adapt resistance via the CRISPR-Cas system. Indeed, the present invention provides a diverse set of virulent phage for use as biocontrol agents. In particularly preferred embodiments, this diversity is targeted at the CRISPR directed mechanism of phage resistance, such that the ability of the host organism to rapidly evolve against phage attack (via CRISPR) is severely reduced or eliminated. The administration of the diverse phage, either as a cocktail or in a sequential rotation further reduces the possibility of the host organism to adapt or evolve CRISPR-directed phage resistance.

Phages are natural antimicrobial agents that have been extensively studied as an alternative therapeutic agent to antibiotics. This interest has been recently renewed, due to the proliferation of multiple-antibiotic resistant pathogens. As with antibiotics, bacteria have developed multiple mechanisms to overcome phage attack. The present invention provides methods and compositions involving the use of lactococcal CRISPR-Cas in mediating phage resistance to generate a diverse phage population, to create synthetic phages devoid of CRISPR motif sequences, as well as methods for administering such phage that will reduce the ability of a target organism to develop resistance against the phage.

As detailed herein, CRISPR-Cas systems have been described in a wide range of organisms which include examples of pathogenic genera. Upon phage infection, bacteria escaping lysis can be found to contain new spacer sequence(s) within a CRISPR array. The new spacer is typically of a defined length that is characteristic for a given CRISPR array and derived from the attacking phage genome to which it confers resistance. As the level of resistance conferred by a single spacer is often not complete, phage can escape the mechanism. Analysis of "escape-phages" indicated that the genomes were mutated in or proximal to the corresponding spacer sequence found in the resistant host variant. Furthermore, the "escape-phages" are fully virulent to the CRISPR-mediated host variant from which they were derived.

One unique aspect of therapeutic phage, distinguishing it from traditional antibiotics, is the ability to propagate exponentially in conjunction with the infected bacteria. While this can be advantageous from a pharmacological perspective, it also provides unique opportunities for the phage to evolve towards adaptive response of the targeted bacteria to phage attack.

Bacteria have developed several defense mechanisms against virulent phage. As indicated herein, the CRISPR-Cas loci play a role in conferring bacterial phage resistance. Following phage infection, analysis of surviving bacteria found that some isolates had inserted a new spacer element within their resident CRISPR locus, the sequence of which was identical to that found in the corresponding phage genome. When challenged with phage, these first generation CRISPR-mediated phage resistant variants give rise to plaques; the phage of which were found to be fully infective on both parent and derivative. Analysis of these "CRISPR-escape" phage indicated that their genomes were mutated in the sequence corresponding to the CRISPR spacer harbored by the phage resistant variant or in a proximal sequence believed to direct spacer insertion and identified as the CRISPR motif specific to a given Cas-CRISPR system. Therefore the "CRISPR-escape" phage is potentially more virulent than the parent and first-generation variants, as this phage is capable of infecting both the parent strain and the first generation CRISPR variant.

As indicated above, CRISPR loci have been identified in several genera/species of bacteria that include examples of known pathogens and spoilage microorganisms. Also as described herein, the present invention provides methods and compositions for utilization of lactococcal CRISPR array in combination with Cas proteins to confer "immunity" to invading foreign DNA, in particular, bacteriophages. Also as described herein, bacterial strains harbouring "active" CRISPR-Cas loci containing a spacer that is identical to a corresponding sequence within a phage genome (i.e., a "protospacer"), confers upon that bacterial strain, resistance to the phage. In some preferred embodiments, the genome sequences of the biocontrol phage are known. In some particularly preferred methods, the isolated target microorganism is examined for the presence of CRISPR loci. In some preferred embodiments, PCR using specific primers for conserved sequences that flank CRISPR loci of the target microorganism finds use. In some preferred embodiments, amplification product(s) are sequenced compared with the genome sequence of the biocontrol phage. In some preferred embodiments, the generation of CRISPR phage resistant variants and analysis of the spacer/protospacer provides means to identify the specific CRISPR motif. Once identified, the sequence information is used to design and synthesize a phage devoid of the lactococcal CRISPR motif. Thus, the resulting phage is insensitive to CRSPR-Cas mediated resistance. In these assessments, the absence of spacers with similarity to the phage genome indicates the susceptibility of the target microorganism (preferably a lactococcal bacteria) to the biocontrol phage. Thus, the biocontrol phage has a greater degree of virulence and efficacy as a biocontrol agent.

The present invention provides methods and compositions suitable for use in the food, feed, medical and veterinary industries to generate phage with broader host range and method of application for more effective biocontrol of lactococcal bacteria. The present invention provides means to produce a sufficient number of altered phage (in response to CRISPR) to significantly reduce the ability of the native bacteria to evolve an effective CRISPR-mediated resistance. The present invention also provides methods of application/administration designed such that the rate of evolution by the native bacteria is significantly reduced.

Starter Cultures

Starter cultures are used extensively in the food industry in the manufacture of fermented products including milk products—such as yoghurt and cheese, meat products, bakery products, wine and vegetable products.

Starter cultures used in the manufacture of many fermented milk, cheese and butter products include cultures of bacteria, generally classified as lactic acid bacteria. Such bacterial starter cultures impart specific features to various dairy products by performing a number of functions.

Commercial non-concentrated cultures of bacteria are referred to in industry as 'mother cultures', and are propagated at the production site, for example a dairy, before being added to an edible starting material, such as milk, for fermentation. The starter culture propagated at the production site for inoculation into an edible starting material is referred to as the 'bulk starter'.

Suitable starter cultures for use in the present invention may include any organism which is of use in the food, cosmetic or pharmaceutical industry.

For example, the starter culture may be suitable for use in the dairy industry. When used in the dairy industry the starter culture may be selected from a lactic acid bacteria species, a *Bifidobacterium* species, a *Brevibacterium* species, a *Propionibacterium* species. Suitable starter cultures of the lactic acid bacteria group include commonly used strains of a *Lactococcus* species, a *Streptococcus* species, a *Lactobacillus* species including the *Lactobacillus acidophilus, Enterococcus* species, *Pediococcus* species, a *Leuconostoc* species and *Oenococcus* species.

Cultures of lactic acid bacteria are commonly used in the manufacture of fermented milk products—such as buttermilk, yoghurt or sour cream, and in the manufacture of butter and cheese, for example Brie or Harvati. *Lactococcus* species include the widely used *Lactococcus lactis*, including *Lactococcus lactis* subsp. *lactis* and *Lactococcus lactis* subsp. *cremoris*.

Other lactic acid bacteria species include *Leuconostoc* sp., *Streptococcus thermophilus, Lactobacillus delbrueckii* subsp. *bulgaricus* and *Lactobacillus helveticus*. In addition, probiotic strains—such as *Lactococcus* species—include the widely used *Lactococcus lactis*, including *Lactococcus lactis* subsp. *lactis* and *Lactococcus lactis* subsp. *cremoris*. Mesophilic cultures of lactic acid bacteria commonly used in the manufacture of fermented milk products such as buttermilk, yoghurt or sour cream, and in the manufacture of butter and cheese, for example Brie or Harvati. Other *Lactococcus* species include *Lactococcus lactis* subsp. *cremoris, Lactococcus lactis, Leuconostoc* sp., *Lactococcus lactis* subsp. *lactis* biovar, *Streptococcus thermophilus, Lactobacillus delbrueckii* subsp. *bulgaricus* and *Lactobacillus helveticus*. In addition, probiotic strains such as *Bifidobacterium lactis, Lactobacillus acidophilus, Lactobacillus casei* may be added during said manufacturing to enhance flavour or to promote health.

Cultures of lactic acid bacteria commonly used in the manufacture of cheddar and Monterey Jack cheeses include *Streptococcus thermophilus, Lactococcus lactis* subsp. *lactis* and *Lactococcus lactis* subsp. *cremoris* or combinations thereof.

Thermophilic cultures of lactic acid bacteria commonly used in the manufacture of Italian cheeses such as Pasta filata or parmesan, include *Streptococcus thermophilus* and *Lactobacillus delbrueckii* subsp *bulgaricus*. Other *Lactobacillus* species—such as *Lactobacillus helveticus*—may be added during manufacturing to obtain a desired flavour.

Advantageously, the starter culture organism may comprise or consist of a genetically modified strain (prepared according to the methods desired herein) of one of the above lactic acid bacteria strains or any other starter culture strain.

The selection of organisms for the starter culture of the invention will depend on the particular type of products to be prepared and treated. Thus, for example, for cheese and butter manufacturing, mesophillic cultures of *Lactococcus* species, *Leuconostoc* species and *Lactobacillus* species are widely used, whereas for yoghurt and other fermented milk products, thermophillic strains of *Streptococcus* species and of *Lactobacillus* species are typically used.

The starter culture may even be a dried starter culture.

The starter culture may be a concentrated starter culture.

The starter culture may be a concentrated starter culture used in direct inoculation.

The starter culture may be a frozen starter culture.

The starter culture may consist of one bacterial strain, i.e., a pure culture. In this case, substantially all, or at least a significant portion of the bacterial starter culture would generally comprise the same bacterium.

In the alternative, the starter culture may comprise several bacterial strains, i.e., a defined mixed culture.

Lactic Acid Bacteria

Particularly suitable starter cultures, in particular dried starter cultures, for use in the present invention comprise lactic acid bacteria.

As used herein the term "lactic acid bacteria" refers to Gram positive, microaerophillic or anaerobic bacteria which ferment sugar with the production of acids including lactic acid as the predominantly produced acid, acetic acid, formic acid and propionic acid. The industrially most useful lactic acid bacteria are found among *Lactococcus* species, such as *Lactococcus lactis, Lactobacillus* species, *Bifidobacterium* species, *Streptococcus species, Leuconostoc* species, *Pediococcus* species and *Propionibacterium* species.

The starter cultures of the present invention may comprise one or more lactic acid bacteria species such as, *Lactococcus lactis, Lactobacillus delbrueckii* subsp. *bulgaricus* and *Streptococcus* thermophilus or combinations thereof.

Lactic acid bacteria starter cultures are commonly used in the food industry as mixed strain cultures comprising one or more species. For a number of mixed strain cultures, such as yoghurt starter cultures comprising strains of *Lactobacillus delbrueckii* subsp. *bulgaricus* and *Streptococcus thermophilus*, a symbiotic relationship exists between the species wherein the production of lactic acid is greater compared to cultures of single strain lactic acid bacteria (Rajagopal et al., 1990).

Preparing Starter Cultures

Starter cultures may be prepared by techniques well known in the art such as those disclosed in U.S. Pat. No. 4,621,058. By way of example, starter cultures may be prepared by the introduction of an inoculum, for example a bacterium, to a growth medium to produce an inoculated medium and ripening the inoculated medium to produce a starter culture.

Preparing Dried Starter Cultures

Dried starter cultures may be prepared by techniques well known in the art, such as those discussed in U.S. Pat. No. 4,423,079 and U.S. Pat. No. 4,140,800.

Dried starter cultures for use in the present invention may be in the form of solid preparations. Examples of solid preparations include, but are not limited to tablets, pellets, capsules, dusts, granules and powders which may be wettable, spray-dried, freeze-dried or lyophilised.

The dried starter cultures for use in the present invention may be in either a deep frozen pellet form or freeze-dried powder form. Dried starter cultures in a deep frozen pellet or freeze-dried powder form may be prepared according to the methods known in the art.

The starter cultures for use in the present invention may be in the form of concentrates which comprise a substantially high concentration of one or more bacteria. Suitably the concentrates may be diluted with water or resuspended in water or other suitable diluents, for example, an appropriate growth medium or mineral or vegetable oils, for use in the present invention. The dried starter cultures of the present invention in the form of concentrates may be prepared according to the methods known in the art, for example by centrifugation, filtration or a combination of such techniques.

Product

Suitable products according to the present invention include, but are not limited to, a foodstuffs, cosmetic products or pharmaceutical products.

Any product, which is prepared from, or comprises, a culture is contemplated in accordance with the present invention. These include, but are not limited to, fruits, legumes, fodder crops and vegetables including derived products, grain and grain-derived products, dairy foods and dairy food-derived products, meat, poultry, seafood, cosmetic and pharmaceutical products.

The term "food" is used in a broad sense and includes feeds, foodstuffs, food ingredients, food supplements, and functional foods.

As used herein the term "food ingredient" includes a formulation, which is or can be added to foods and includes formulations which can be used at low levels in a wide variety of products that require, for example, acidifying or emulsifying.

As used herein, the term "functional food" means a food which is capable of providing not only a nutritional effect and/or a taste satisfaction, but is also capable of delivering a further beneficial effect to consumer. Although there is no legal definition of a functional food, most of the parties with an interest in this area agree that there are foods marketed as having specific health effects.

The term "food" covers food for humans as well as food for animals (i.e. a feed). In a preferred aspect, the food is for human consumption.

The cells described herein may be—or may be added to—a food ingredient, a food supplement, or a functional food.

The food may be in the form of a solution or as a solid—depending on the use and/or the mode of application and/or the mode of administration.

The cells described herein can be used in the preparation of food products such as one or more of: confectionery products, dairy products, meat products, poultry products, fish products and bakery products.

By way of example, the bacterium can be used as ingredients to soft drinks, a fruit juice or a beverage comprising whey protein, health teas, cocoa drinks, milk drinks and lactic acid bacteria drinks, yoghurt, drinking yoghurt and wine.

There is also provided a method of preparing a food, the method comprising admixing the cells according to the present invention with a food ingredient (such as a starting material for a food). The method for preparing a food is also another aspect of the present invention.

Suitably a food as described herein is a dairy product. More preferably a dairy product as described herein is one or more of the following: a yoghurt, a cheese (such as an acid curd cheese, a hard cheese, a semi-hard cheese, a cottage cheese), a buttermilk, quark, a sour cream, kefir, a fermented whey-based beverage, a koumiss, a milk drink and a yoghurt drink. The term feed as used herein includes raw and processed plant material and non-plant material. The feed may be any feed suitable for consumption by an animal, including livestock (animal) feed, for example poultry feed, fish feed or crustacean feed for example.

Example 1

Isolation and Identification of a Novel Plasmid-Encoded CRISPR-Cas in *Lactococcus lactis*

*Lactococcus lactis* subsp. *cremoris* DGCC7167 has been identified as containing at least 7 (possibly 9) native plasmids. DGCC7167 was electroporated with the antibiotic (Em=erythromycin) resistance encoding vector pGhost9::ISS1 and used as a donor in, conjugative mating to a plasmid-free strain (IL1403-S4) and selecting for transfer of Em resistance using standard laboratory techniques. Em resistant transconjugants were screened for phage resistance. A representative phage resistant isolate (designated K) was selected. Isolate K contained multiple plasmids (FIG. 1) and exhibited resistance to at least four different phage types (bIL67, bIL170, 949, and P335, Table 1). De novo resistance against four different phage types indicated that the phenotype was likely not the result of spontaneous mutation, but acquired through conjugal transfer of one or more plasmids from DGCC7167

To determine which if any of the multiple plasmids encoded phage resistance, Isolate K was used as a conjugative donor for transfer of Em resistance into another plasmid-free strain, LM2345. Em resistant transconjugants were screened for phage resistance to homologous phage p2 (936-type). A representative phage resistant transconjugant (designated KLM) was isolated. Strain KLM contained a single plasmid, designated pDCD537KLM, which was purified and submitted to DNA sequencing.

Figure 2:
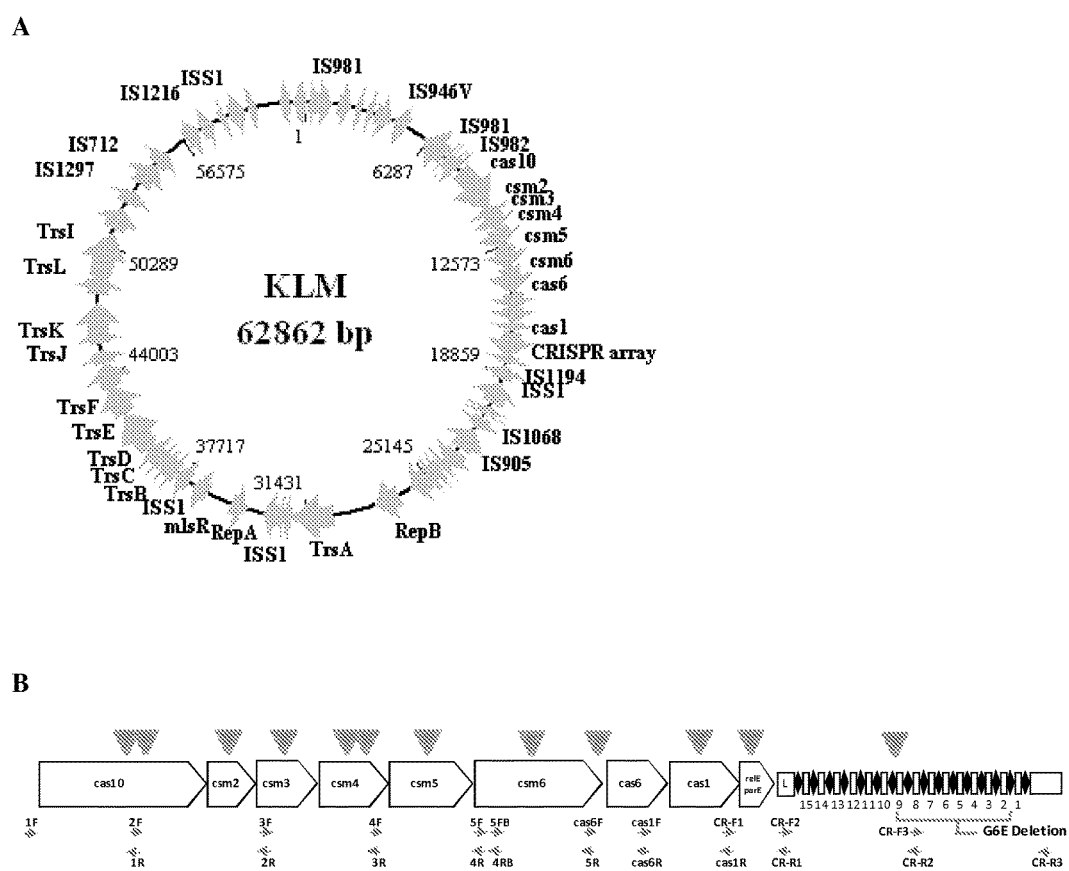
FIG. 2 shows a map of the 62,862-nt self-transmissible, phage resistance encoding cointegrate plasmid pDCD537KLM (Panel A) and resident CRISPR-Cas locus (Panel B). The arrows ⚑ shown above the CRISPR-Cas array in Panel B indicate the position of each unique ISS1 insertion mapped onto the locus from transpositional mutagenesis experiments. Small arrows ⇢ show the position of the various primers used for PCR and sequencing reactions.

The complete sequence of pDCD537KLM identified a plasmid of 62,862-nt that contained (see Sequence Listing and Table 2) 1) a unique CRISPR array (SEQ ID NO 22); 2) nine genes adjacent to the CRISPR array; eight of which were shown to have significant similarity to csm/cas genes (SEQ ID NO 3, 5, 7, 9, 11, 13, 15, and 17) and the ninth with similarity to relE (SEQ ID NO 19); 3) conjugative functions derived from plasmid pMRC01 (Dougherty et al., 1998); 4) the inserted pGhost9::ISS1 (sequencing defined the precise point and nature of the insertion event); 5) ten insertion sequences that include ISS1 (2 copies from pGhost 9::ISS1, plus 3 additional, IS905 (1), IS981 (1), IS1216 (1), IS1297 (1), IS712A (1). Plasmid map of pDCD537KLM and the CRISPR-Cas locus is shown in FIG. 2A Example 2

Phage Resistance is Encoded on p537KLM

To confirm that phage resistance is encoded on plasmid pDCD537KLM, isolate KLM was used as a conjugal donor of Em resistance to plasmid-free recipients LM2301 and 1403-S4. Em resistant transconjugants of both recipients were isolated and found to contain a single plasmid of the same size as pDCD537KLM. All transconjugants were resistant against their homologous phage (Table 3). PCR analysis confirmed the presence of the CRISPR array and cas1 gene in each of the transconjugants.

Further proof that phage resistance is encoded on pDCD537KLM was provided by subjecting strain KLM to plasmid curing. KLM was propagated at 3° C. in the absence of Em and phage selection. Following six sequential transfers, Em sensitive variants were isolated and screened for phage resistance phenotype. Phage sensitive variants were found to have lost pDCD537KLM. PCR analysis confirmed the loss of the CRISPR array, cast gene, and pGhost9::ISS1. Em resistant, phage resistant colonies isolated during the same experiment were found to have retained pDCD537KLM.

Example 3

Analysis of the p537KLM CRISPR-Cas System

The CRISPR array of plasmid p537KLM contains sixteen 36-nt repeats defined by the sequence 5'-AAATACAAC- CGCTCCTCGATAAAAGGGGACGAGAAC-3' (SEQ ID NO 24). Blast analysis determined the repeat sequence as not present in GenBank as of Oct. 10, 2011. The closest relevant similarity was identified as an 18 of 36-nt match to a CRISPR repeat found in *Staphylococcus lugdunensis* (accession N920143) and in two whole genome shotgun sequences from *Staphylococcus epidermidis* isolates (VCU037 contig00025 [accession AFTY01000003] and VCU045 contig00062 [accession AFEI01000033]).

The CRISPR repeats are interspaced by fifteen spacers (SEQ ID NO 25-39) that vary in length from 33 to 39-bp. BLAST analysis of the spacers revealed significant similarities to lactococcal phage sequences (Table 4). In particular, the following spacers were found to have partial identities to lactococcal phage: i) spacer s2 (SEQ ID NO 38): phage P008, type 936; ii) spacers s3 (SEQ ID NO 37) and s4 (SEQ ID NO 36): phage of 936-type including phage p2; iii) s3 also shows partial identity to phage 4268; iv) spacers s5 (SEQ ID NO 35), s8 (SEQ ID NO 32), s10 (SEQ ID NO 30), and s13 (SEQ ID NO 27): phage 949. Based on the current understanding of CRISPR-Cas mediated interference of foreign DNA (Horvath and Barrangou, 2010; Karginov and Hannon, 2010), these results strongly correlate the presence of specific spacers in the lactococcal CRISPR array with phage resistance phenotype.

Immediately flanking the CRISPR array are two regions that are characteristic of CRISPR genetic loci; a 150-bp of non-coding DNA potentially constituting the leader region (SEQ ID NO 21) and a cluster of nine open reading frames (ORFs) as determined using GeneMark for Prokaryotes. BLAST analysis of the ORFs identified significant similarities to CRISPR associated proteins (Table 5). Eight consecutive genes were identified as cas10, csm2, csm3, csm4, csm5, csm6, cash, and cast based on Makarova et al. (2011). The last ORF in the series, adjacent to the leader, was found to contain a conserved domain belonging to pfam05016 plasmid stabilization system protein and was designated relE. In all, plasmid pDCD537KLM contains eight CRISPR-associated genes plus relE organized as a putative operon which is adjacent to the CRISPR array separated by a 150-nt leader sequence. Based on Makarova et al. (2011) the lactococcal CRISPR-Cas is a Type III-A system.

Example 4

Isolation of a "Food-Grade" Lactococcal Conjugative CRISPR-Cas Plasmid

*L. lactis* DGCC7167 was used as a donor for the conjugal transfer of lactose (Lac) fermenting ability to plasmid-free recipient LM2302. Lac fermenting transconjugants were tested for presence of the CRISPR array by PCR. CRISPR-containing isolates were subsequently screened for resistance to phage p2. A representative phage resistant isolate (designated 2302LP) was isolated. 2302LP contained a single plasmid (designated pDCD537LP) that was confirmed to contain the CRISPR array and csm/cas genes identical to pDCD537KLM/pDCD537CC. 2302LP was propagated at 3TC in the absence of lactose, generating a Lac negative (lactose non-fermenting) variant (designated 2302LN) which tested resistant to phage p2. 2302LN contained a single plasmid, designated pDCD537LN, which was confirmed to contain the CRISPR array and csm/cas genes identical to pDCD537KLM/pDCD537CC.

Full functionality of pDCD537LN was demonstrated when it was conjugally transferred from 2302LN into plasmid-free recipients LM2345 and ID 403, selecting for resistance to phage. Phage resistant transconjugants were obtained for both LM2345 (resistance to phage p2) and IL1403 (resistance to phage bIL170). The presence of pDCD537LN in IL1403 transconjugants was confirmed by PCR amplification of the CRISPR array and cast, and resistance to phage 949 in addition to bIL170.

Example 5

Cas Proteins are Necessary for Phage Resistance

Strain 1403LN (IL1403+pDCD537LN) was electroporated with vector pGhost9::ISS1, which encodes Em resistance, and was used as a donor to transfer Em resistance in conjugal mating experiments into plasmid-free recipient LM2345. Insertion sequence ISS1 has been shown to randomly insert in lactococci (Dinsmore et al., 1993; Maguin et al, 1996). Conjugal transfer of Em resistance requires insertion of pGhost9::ISS1, facilitated by insertion sequence ISS1, into self-transmissible plasmid pDCD537LN. Em resistant transconjugants were tested for phage resistance phenotype, and phage sensitive isolates were selected for further characterization. PCR amplification across the csm/cas operon of each phage sensitive transconjugant identified at least one unique ISS1 insertion into eight of the nine csm/cas and the relE genes (FIG. 3B). No insertion was found in cash. In all cases, ISS1 insertion resulted in the loss of phage resistance, indicating that the csm/cas genes are involved in phage resistance.

Example 6

Phage Resistance is Directed by CRISPR Spacers

In *S. thermophilus* when the CRISPR array is interrupted, phage resistance as directed by the downstream (relative to direction of transcription) displaced spacers is lost (Barrangou et al. 2007). Transcription of the CRISPR array is believed to initiate from the leader region, transcribing the proximal spacers (most recently acquired) and progressing 5' to 3' through the length of the array. From the transposon mutagenesis experiments, an Em resistant transconjugant, designated 2345F8-2, was found to be sensitive to phage p2. Examination of the CRISPR determined that ISS1 had inserted into spacer s9 within pDCD537LN array (FIG. 3B). In the lactococcal CRISPR array, spacers s4 and s3 have partial identity to phage p2 and are downstream of the expected direction of transcription from spacer s9. ISS1 insertion into spacer s9 interrupts the CRISPR array, disrupting the expression of downstream spacers that include s4 and s3. Loss of resistance to phage p2 following ISS1 insertion into spacer s9 indicates that spacer s4 and/or s3 are involved in resistance to phage p2.

Subsequently, 2345F8-2 was used as a conjugal donor to transfer the ISS1::s9 inserted variant of pDCD537LN into strain 1403-S4 which is sensitive to phage 949. Within the pDCD537LN CRISPR array, four spacers, s13, s10, s8 and s5, show partial identity to phage 949 and are hypothesized to direct the phage resistance phenotype against phage 949. Insertion of ISS1 into spacer s9 displaced spacers s8 and s5, however spacers S13 and s10 remain in proper context relative to the expected direction of transcription of the array. An Em resistant transconjugant of 1403-S4, confirmed to contain the ISS1::s9 inserted pDCD537LN, tested phage resistant to phage 949 indicating spacers s13 and/or s10 are directing resistance to phage 949 (Table 6).

Spacer s4 has partial identity to phage bIL170 and as noted above is displaced by the insertion of ISS1 into spacer s9. The 1403-S4 transconjugant harboring the ISS1::s9 inserted pDCD537LN was sensitive to bIL170 indicating that spacer s4 is directing the resistance to phage bIL170.

In yet another example, an Em resistant, phage p2 sensitive transconjugant, designated 2345G6E, was isolated from the transpositional mutagenesis experiments. 2345G6E harbors a pDCD537LN::pGhost9::ISS1 cointegrate, designated pDCD537G6E, which was found to have a deletion within the CRISPR array resulting in the precise loss of spacers s2 through s9 (FIG. 3B). Commensurate with the loss of spacers s3 and s4 (identity to phage p2), strain 2345G6E was sensitive to phage p2. pDCD537G6E was then conjugally transferred into 1403-S4. An Em resistant transconjugant, designated 1403-S4G6E (confirmed to contain pDCD537G6E), tested resistant to phage 949 (as directed by spacers s10 and s13) but sensitive to phage bIL170 (spacer s4), confirming the CRISPR-cas system is functional and dependent upon the presence of specific spacers for phage resistance.

Further proof that the lactococcal CRISPR spacers direct phage resistance comes from the analysis of "escape" phage. As demonstrated in S. thermophilus, phages that escaped CRISPR-Cas immunity were found to have a mutation within the corresponding phage genome sequence (protospacer) or PAM (protospacer adjacent motif) (Barrangou et al., 2007, Deveau et al. 2007). In one example, pDCD537KLM was conjugally transferred into industrial starter strain DGCC7192 which is sensitive to phage M5949 and M5952 which are homologous to lactococcal phage 4268 (Trotter et al., 2006). Unexpectedly, DGCC7192 transconjugants harboring pDCD537KLM tested resistant to phages M5949 and M5952. Examination of the 35-nt spacer s3 identified a 22-nt contiguous sequence that is found in the genome of phage 4268 (Trotter et al., 2006). The same sequence identity was confirmed in phages M5949 and M5952, indicating spacer s3 is directing phage resistance against these phage. Escape phage of M5949 and M5952 were isolated from standard plaque assays of DGCC7192+ pDCD537KLM. Sequencing the s3 protospacer and flanking DNA of the respective escape phage genomes found a single nucleotide mutation within the protospacer region corresponding to spacer s3 (Table 7), confirming the involvement of s3 phage resistance.

In addition, plasmid pDCD537LN was conjugally transferred into DGCC7192 using phage resistance as a selection marker. Transconjugants resistant to phage M5952 were isolated at approximately 5E-05 per exit recipient. A representative transconjugant was selected and confirmed to contain pDCD537LN by PCR of the CRISPR array and cas1 gene. In standard plaque assay with phage M5952, escape phages were observed at approximately 1 E-06 pfu/ml. An additional 73 escape phage were characterized and found to have a single nucleotide mutation within the corresponding s3 protospacer sequence of each phage (Table 7).

Example 7

Lactococcal CRISPR Spacer Engineering

To determine if the lactococcal CRISPR could be purposely directed to confer resistance to a specific phage, the array was engineered to exchange a new spacer for the existing complement of spacers. The truncated CRISPR array from plasmid pDCD537G6E was chosen as a starting platform since the loss of phage resistance to p2 and bIL170, as directed by spacer s3 and s4, resulted from the deletion of spacers s2 through s9. In preparation, pDCD537G6E was first cured of pGhost9::ISS1 encoded Em resistance. 1403-S4G6E was subjected to sequential propagation at 37° C. in the absence of erythromycin. An Em sensitive variant was isolated, designated 1403-S4G6, containing a single plasmid, designated pDCD537G6, which was visibly smaller than pDCD537G6E based on plasmid analysis.

A CRISPR array, composed of a single copy of spacer s4 flanked on both ends by a single lactococcal CRISPR repeat with additional sequence derived from the pDCD537KLM CRISPR-Cas locus for homologous recombination was synthesized.

Figure 3:
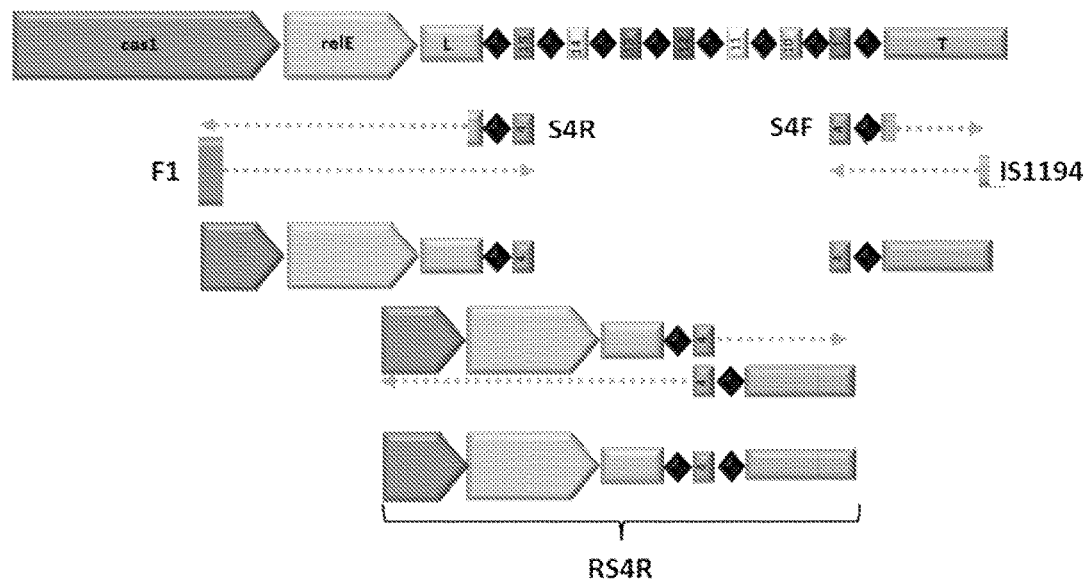
FIG. 3 shows the synthesis of repeat-spacer-repeat construct designed to exchange lactococcal CRISPR spacer s4 into the pDCD537G6 array. The final construct, RS4R contains the s4 spacer flanked by two repeats with sufficient sequence on either end to promote cross-over homologous recombination.

Plasmid DNA from 1403-S4G6 was used as a template to amplify two distinct PCR fragments using primer set CR-F1 and S4R in one reaction, and primer set S4F and IS1194 in another reaction. Both PCR products were subsequently used as templates in another PCR reaction using primers CR-F1 and IS1194 to generate the RS4R construct which spans from the 3' end of gene cast through to the IS1194 fragment (FIG. 3).

The RS4R construct was sub-cloned into the Invitrogen pCR2.1-TOPO system, resulting in plasmid pTOPOS4. SpeI digested pTOPOS4 was cloned into similarly digested pGhost9 (Em resistance) in Escherichia coli JM109, resulting in the pRS4R fusion plasmid whose structure was confirmed by DNA sequencing. pRS4R was then electroporated into 1403-S4G6, and an Em resistant transformant was used as a conjugal donor (conjugation facilitated by self-transmissible pDCD537G6) of pRS4S to plasmid-free recipient LM2345. Em resistant transconjugants, which subsequently tested positive for resistance to phage p2, were found to contain a large plasmid; putatively a pDCD537G6:: pRS4R cointegrate resulting from homologous recombination. PCR amplification of the Em resistant, phage resistant transconjugants using primer cas1F and one primer designed within spacer s4 produced an amplicon of the size expected for the replacement of the pDCD537G6 array with the single s4 spacer RS4R construct. DNA sequencing confirmed the replacement. This result, coupled with the concurrent acquisition of resistance to phage p2, demonstrates that the lactococcal CRISPR can be engineered to confer resistance to specific phage.

Example 8

Identification of the Lactococcal CRISPR-Cas in Other Lactococcal Strains

Figure 4:
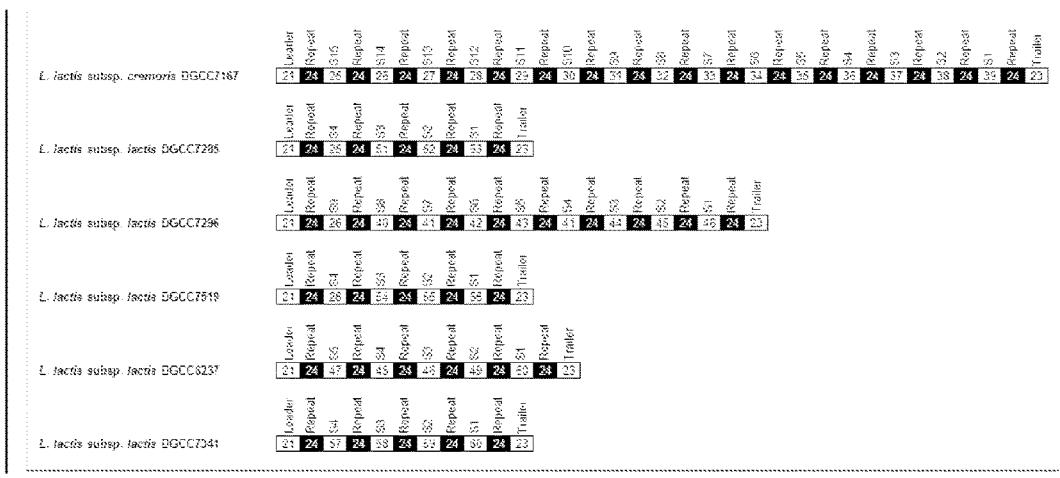
FIG. 4 shows variable spacer content of *Lactococcus lactis* strains found to contain a CRISPR array.

Strains from the Danisco Global Culture Collection were screened for the presence of a lactococcal CRISPR array. Total genomic DNA was amplified with primer set RLa-F5 and RLa-R6 which target the repeat and for detection of a CRISPR array and primer set cas1F and cas1R to detect tcas1, respectively. Strains generating a PCR product were tested for the presence of additional csm/cas genes by PCR amplification. Over 200 strains from the collection were examined from which five strains were confirmed to contain a CRISPR array and a full complement of pDCD537KLM csm/cas genes. The relE gene was sequenced using primer set CR-F1 and CR-R1, and found to be greater than 99% identical to relE in pDCD537KLM. Interestingly, PCR amplification of the CRISPR array using primer set CR-F2 and CR-R3 generated different size amplicons indicating spacer content diversity. DNA sequencing showed that each array contained repeats of identical length and sequence to that found in pDCD537KLM. As predicted by the variable amplicon sizes, spacer content varied in number and sequence as compared to the pDCD537KLM array (FIG. 4). The presence of cas1 and relE suggest a common ancestor for each of the six CRISPR/Cas loci, however the diversity of spacer content would indicate varied exposure to foreign DNA as would be expected of an actively adaptive system. Examination of the spacers at the leader, the proposed "active acquisition" end, identifies examples of common spacer content. The terminal spacer in strains DGCC7519 and 7296 are identical to the penultimate spacer of DGCC7167, although no other spacers are in common. Strains DGCC7167 and 7285 also share the same terminal spacer; again no other spacers are in common. These findings suggest each strain acquired the spacer through recent contact with a foreign invasive genetic element containing the respective spacer DNA. Acquisition of identical spacers in genetically distinct strains has previously been observed (Horvath et al., 2008).

TABLE 1

Efficiency of plaquing of 1403-S4 and 1403-S4 transconjugants A, B, C, D, E, F, G, H, I, J, L, and K.

| | Efficiency of Plaquing | | | |
|---|---|---|---|---|
| Strain | bIL67 (c2-type) | bIL170 (936-type) | 949 | P335 |
| 1403 S4 | 1 | 1 | 1 | 1 |
| A | 1 | $2.1 \times 10^{-5}$ | $1 \times 10^{-4}$ | NT |
| B | 1 | $\sim 1 \times 10^{-1}$ | $1 \times 10^{-2}$ | NT |
| C | 1 | $2.1 \times 10^{-5}$ | $1 \times 10^{-4}$ | NT |
| D | 1 | $2.1 \times 10^{-5}$ | $1 \times 10^{-4}$ | NT |
| F | 1 | $2.1 \times 10^{-5}$ | $1 \times 10^{-4}$ | NT |
| G | 1 | $\sim 1 \times 10^{-1}$ | $1 \times 10^{-3}$ | NT |
| H | $3.3 \times 10^{-5}$ | $2.1 \times 10^{-4}$ | 1 | NT |
| I | 1 | $2.1 \times 10^{-5}$ | $1 \times 10^{-3}$ | NT |
| J | 1 | $2.1 \times 10^{-5}$ | $1 \times 10^{-3}$ | NT |
| K | $<3.3 \times 10^{-7}$ | $<2.1 \times 10^{-7}$ | $1 \times 10^{-5}$ | $<1.9 \times 10^{-7}$ |
| L | 1 | 1 | 1 | NT |

TABLE 2

Listing of *Lactococcus lactis* CRISPR sequences.

| SEQ ID | Length | Description |
|---|---|---|
| SEQ ID 1 | 9873 | DNA sequence of the whole CRISPR/cas region in *Lactococcus lactis* subsp. *cremoris* DGCC7167, including 200 bp of sequence upstream of the first cas gene (csm1), up to the trailer sequence (33 bp downstream of the last CRISPR repeat). |
| SEQ ID 2 | 200 | DNA sequence located upstream of the first cas gene (cas10) in *Lactococcus lactis* subsp. *cremoris* DGCC7167 |
| SEQ ID 3 | 2274 | DNA sequence of the cas10 gene in *Lactococcus lactis* subsp. *cremoris* DGCC7167 |
| SEQ ID 4 | 757 | Protein sequence of Cas10 in *Lactococcus lactis* subsp. *cremoris* DGCC7167 |
| SEQ ID 5 | 423 | DNA sequence of the csm2 gene in *Lactococcus lactis* subsp. *cremoris* DGCC7167 |
| SEQ ID 6 | 140 | Protein sequence of Csm2 in *Lactococcus lactis* subsp. *cremoris* DGCC7167 |
| SEQ ID 7 | 645 | DNA sequence of the csm3 gene in *Lactococcus lactis* subsp. *cremoris* DGCC7167 |
| SEQ ID 8 | 214 | Protein sequence of Csm3 in *Lactococcus lactis* subsp. *cremoris* DGCC7167 |
| SEQ ID 9 | 894 | DNA sequence of the csm4 gene in *Lactococcus lactis* subsp. *cremoris* DGCC7167 |
| SEQ ID 10 | 297 | Protein sequence of Csm4 in *Lactococcus lactis* subsp. *cremoris* DGCC7167 |
| SEQ ID 11 | 1062 | DNA sequence of the csm5 gene in *Lactococcus lactis* subsp. *cremoris* DGCC7167 |
| SEQ ID 12 | 353 | Protein sequence of Csm5 in *Lactococcus lactis* subsp. *cremoris* DGCC7167 |
| SEQ ID 13 | 1230 | DNA sequence of the csm6 gene in *Lactococcus lactis* subsp. *cremoris* DGCC7167 |
| SEQ ID 14 | 409 | Protein sequence of Csm6 in *Lactococcus lactis* subsp. *cremoris* DGCC7167 |
| SEQ ID 15 | 747 | DNA sequence of the cas6 gene in *Lactococcus lactis* subsp. *cremoris* DGCC7167 |
| SEQ ID 16 | 248 | Protein sequence of Cas6 in *Lactococcus lactis* subsp. *cremoris* DGCC7167 |
| SEQ ID 17 | 756 | DNA sequence of the cas1 gene in *Lactococcus lactis* subsp. *cremoris* DGCC7167 |
| SEQ ID 18 | 251 | Protein sequence of Cas1 in *Lactococcus lactis* subsp. *cremoris* DGCC7167 |
| SEQ ID 19 | 333 | DNA sequence of the relE/parE gene in *Lactococcus lactis* subsp. *cremoris* DGCC7167 |
| SEQ ID 20 | 110 | Protein sequence of RelE/ParE in *Lactococcus lactis* subsp. *cremoris* DGCC7167 |
| SEQ ID 21 | 150 | DNA sequence of the CRISPR leader (downstream of relE/parE, and upstream of the first repeat) in *Lactococcus lactis* subsp. *cremoris* DGCC7167 |
| SEQ ID 22 | 1114 | DNA sequence of the CRISPR repeat-spacer array (from the first repeat to the last repeat) in *Lactococcus lactis* subsp. *cremoris* DGCC7167 |
| SEQ ID 23 | 33 | DNA sequence of the CRISPR trailer (downstream of the last repeat) in *Lactococcus lactis* subsp. *cremoris* DGCC7167 |
| SEQ ID 24 | 36 | DNA sequence of the CRISPR repeat in *Lactococcus lactis* subsp. *cremoris* DGCC7167 |
| SEQ ID 25 | 35 | DNA sequence of the CRISPR spacer S15 in *Lactococcus lactis* subsp. *cremoris* DGCC7167 = CRISPR spacer S4 in *Lactococcus lactis* subsp. *lactis* DGCC7285 |
| SEQ ID 26 | 38 | DNA sequence of the CRISPR spacer S14 in *Lactococcus lactis* subsp. *cremoris* DGCC7167 = CRISPR spacer S9 in *Lactococcus lactis* subsp. *lactis* DGCC7296 = CRISPR spacer S4 in *Lactococcus lactis* subsp. *lactis* DGCC7519 |
| SEQ ID 27 | 38 | DNA sequence of the CRISPR spacer S13 in *Lactococcus lactis* subsp. *cremoris* DGCC7167 |
| SEQ ID 28 | 34 | DNA sequence of the CRISPR spacer S12 in *Lactococcus lactis* subsp. *cremoris* DGCC7167 |
| SEQ ID 29 | 35 | DNA sequence of the CRISPR spacer S11 in *Lactococcus lactis* subsp. *cremoris* DGCC7167 |
| SEQ ID 30 | 39 | DNA sequence of the CRISPR spacer S10 in *Lactococcus lactis* subsp. *cremoris* DGCC7167 |
| SEQ ID 31 | 38 | DNA sequence of the CRISPR spacer S9 in *Lactococcus lactis* subsp. *cremoris* DGCC7167 |

TABLE 2-continued

Listing of *Lactococcus lactis* CRISPR sequences.

| SEQ ID | Length | Description |
|---|---|---|
| SEQ ID 32 | 35 | DNA sequence of the CRISPR spacer S8 in *Lactococcus lactis* subsp. *cremoris* DGCC7167 |
| SEQ ID 33 | 33 | DNA sequence of the CRISPR spacer S7 in *Lactococcus lactis* subsp. *cremoris* DGCC7167 |
| SEQ ID 34 | 37 | DNA sequence of the CRISPR spacer S6 in *Lactococcus lactis* subsp. *cremoris* DGCC7167 |
| SEQ ID 35 | 37 | DNA sequence of the CRISPR spacer S5 in *Lactococcus lactis* subsp. *cremoris* DGCC7167 |
| SEQ ID 36 | 35 | DNA sequence of the CRISPR spacer S4 in *Lactococcus lactis* subsp. *cremoris* DGCC7167 |
| SEQ ID 37 | 35 | DNA sequence of the CRISPR spacer S3 in *Lactococcus lactis* subsp. *cremoris* DGCC7167 |
| SEQ ID 38 | 35 | DNA sequence of the CRISPR spacer S2 in *Lactococcus lactis* subsp. *cremoris* DGCC7167 |
| SEQ ID 39 | 34 | DNA sequence of the CRISPR spacer S1 in *Lactococcus lactis* subsp. *cremoris* DGCC7167 |
| SEQ ID 40 | 35 | DNA sequence of the CRISPR spacer S8 in *Lactococcus lactis* subsp. *lactis* DGCC7296 |
| SEQ ID 41 | 37 | DNA sequence of the CRISPR spacer S7 in *Lactococcus lactis* subsp. *lactis* DGCC7296 = CRISPR spacer S4 in *Lactococcus lactis* subsp. *lactis* DGCC7296 |
| SEQ ID 42 | 36 | DNA sequence of the CRISPR spacer S6 in *Lactococcus lactis* subsp. *lactis* DGCC7296 |
| SEQ ID 43 | 41 | DNA sequence of the CRISPR spacer S5 in *Lactococcus lactis* subsp. *lactis* DGCC7296 |
| SEQ ID 44 | 35 | DNA sequence of the CRISPR spacer S3 in *Lactococcus lactis* subsp. *lactis* DGCC7296 |
| SEQ ID 45 | 37 | DNA sequence of the CRISPR spacer S2 in *Lactococcus lactis* subsp. *lactis* DGCC7296 = CRISPR spacer S4 in *Lactococcus lactis* subsp. *lactis* DGCC6237 |
| SEQ ID 46 | 37 | DNA sequence of the CRISPR spacer S1 in *Lactococcus lactis* subsp. *lactis* DGCC7296 |
| SEQ ID 47 | 34 | DNA sequence of the CRISPR spacer S5 in *Lactococcus lactis* subsp. *lactis* DGCC6237 |
| SEQ ID 48 | 35 | DNA sequence of the CRISPR spacer S3 in *Lactococcus lactis* subsp. *lactis* DGCC6237 |
| SEQ ID 49 | 34 | DNA sequence of the CRISPR spacer S2 in *Lactococcus lactis* subsp. *lactis* DGCC6237 |
| SEQ ID 50 | 38 | DNA sequence of the CRISPR spacer S1 in *Lactococcus lactis* subsp. *lactis* DGCC6237 |
| SEQ ID 51 | 38 | DNA sequence of the CRISPR spacer S3 in *Lactococcus lactis* subsp. *lactis* DGCC7285 |
| SEQ ID 52 | 36 | DNA sequence of the CRISPR spacer S2 in *Lactococcus lactis* subsp. *lactis* DGCC7285 |
| SEQ ID 53 | 38 | DNA sequence of the CRISPR spacer S1 in *Lactococcus lactis* subsp. *lactis* DGCC7285 |
| SEQ ID 54 | 36 | DNA sequence of the CRISPR spacer S3 in *Lactococcus lactis* subsp. *lactis* DGCC7519 |
| SEQ ID 55 | 34 | DNA sequence of the CRISPR spacer S2 in *Lactococcus lactis* subsp. *lactis* DGCC7519 |
| SEQ ID 56 | 37 | DNA sequence of the CRISPR spacer S1 in *Lactococcus lactis* subsp. *lactis* DGCC7519 |
| SEQ ID 57 | 34 | DNA sequence of the CRISPR spacer S4 in *Lactococcus lactis* subsp. *lactis* DGCC7341 |
| SEQ ID 58 | 36 | DNA sequence of the CRISPR spacer S3 in *Lactococcus lactis* subsp. *lactis* DGCC7341 |
| SEQ ID 59 | 34 | DNA sequence of the CRISPR spacer S2 in *Lactococcus lactis* subsp. *lactis* DGCC7341 |
| SEQ ID 60 | 34 | DNA sequence of the CRISPR spacer S1 in *Lactococcus lactis* subsp. *lactis* DGCC7341 |

TABLE 3

Phage resistance phenotype of plasmid-free conjugative recipients (1403-S4 and LM2301) and their respective transconjugants containing the CRISPR/Cas plasmid pDCD537KLM.

| Strain | Phage and Resistance Phenotype | | | | | | |
|---|---|---|---|---|---|---|---|
| | bIL67 (c2-type) | bIL170 (936-type) | P008 (936-type) | 949 | P335 | c2 (c2-type) | p2 (936-type) |
| 1403-S4 | S | S | S | S | S | | |
| 1403-S4 + pDCD537KLM | S | R | R | R | S | | |
| LM2301 | | | | | | S | S |
| LM2301 + pDCD537KLM | | | | | | S | R |

S = Sensitive
R = Resistant

TABLE 4

BLAST search hits for spacer sequences in CRISPR/Cas containing plasmid pDCD537KLM.

| Spacer | Length | Sequence | BLAST |
|---|---|---|---|
| s15 | 35-nt | tgcatgtttatagccctgccggatttttaagctgcgNB | |
| s14 | 38-nt | tgcatgtttatagccctgccggatttttaagctgcggb | HQ141410.1\|_*Lactobacillus* phage LF1 (32884-32867); Score = 36.2 bits (18), Expect = 8.5 Identities = 18/18 (100%), Gaps = 0/18 (0%) |

TABLE 4-continued

BLAST search hits for spacer sequences in CRISPR/Cas containing plasmid pDCD537KLM.

| Spacer | Length | Sequence | BLAST |
|---|---|---|---|
| s13 | 38-nt | tgcatgtttatagccctgccggattttaagctgcgg | gb\|HM029250.1\|*Lactococcus* phage 949 (25400-25363); Score = 60.0 bits (30), Expect = 6e-07, Identities = 36/38 (95%), Gaps = 0/38 (0%) |
| s12 | 34-nt | tgcatgtttatagccctgccggattttaagctgcgg | gb\|CP002621.1\|*Enterococcus faecalis* OG1RF (714918-714938); Score = 42.1 bits (21), Expect = 0.11, Identities = 21/21 (100%), Gaps = 0/21 (0%) |
| s11 | 35-nt | tgcatgtttatagccctgccggattttaagctgcg | NB |
| s10 | 39-nt | tgcatgtttatagccctgccggattttaagctgcgg | gb\|HM029250.1\|*Lactococcus* phage 949 (15790-15827); Score = 54.0 bits (27), Expect = 4e-05, Identities = 37/39 (95%), Gaps = 1/39 (3%) |
| s9 | 38-nt | tgcatgtttatagccctgccggattttaagctgcg | dbj\|AP006716.1\|*Staphylococcus haemolyticus* JCSC1435 (162631-162649); Score = 38.2 bits (19), Expect = 2.1, Identities = 19/19 (100%), Gaps = 0/19 (0%) |
| s8 | 35-nt | tgcatgtttatagccctgccggattttaagctgcgg | gb\|HM029250.1\|*Lactococcus* phage 949 (16069-16101); Score = 34.2 bits (17), Expect = 28, Identities = 23/25 (92%), Gaps = 0/25 (0%) |
| s7 | 33-nt | tgcatgtttatagccctgccggattttaagctgcg | NB |
| s6 | 37-nt | tgcatgtttatagccctgccggattttaagctgcg | NB |
| s5 | 37-nt | tgcatgtttatagccctgccggattttaagctgcgg | gb\|HM029250.1\|*Lactococcus* phage 949 (49676-49646); Score = 46.1 bits (23), Expect = 0.008, Identities = 29/31 (94%), Gaps = 0/31(0%) |
| s4 | 35-nt | tgcatgtttatagccctgccggattttaagctgcgg | gb\|GQ979703.1\|*Lactococcus lactis* phage p2 (19290-19325); Score = 44.1 bits (22), Expect = 0.029, Identities = 25/26 (96%), Gaps = 0/26 (0%) additional hits: CB20 CB19, CB14, CB13 SL4, bIBB29, jj50, p008, sk1, bIL170 |
| s3 | 35-nt | tgcatgtttatagccctgccggattttaagctgcgg | gb\|GQ979703.1\|*Lactococcus lactis* phage p2 (22439-22473); Score = 54.0 bits (27), Expect = 3e-05, Identities = 30/31 (97%), Gaps = 0/31 (0%), additional hits: bIBB29, SL4, jj50, sk1, 4268, BK5-T, bIL286, *Lactococci* prophage |
| s2 | 35-nt | tgcatgtttatagccctgccggattttaagctgcgg | gb\|DQ054536.1\|*Lactococcus* phage P008 (18873-18907); Score = 54.0 bits (27), Expect = 3e-05, Identities = 33/35 (94%), Gaps = 0/35 (0%); Additional match bIBB29 |
| s1 | 34-nt | tgcatgtttatagccctgccggattttaagctgcg | dbj\|AB563188.1\|*Enterococcus faecalis* plasmid pTW9 (38877-38858); Score = 40.1 bits (20), Expect = 0.42, Identities = 20/20 (100%), Gaps = 0/20 (0%) |

TABLE 5

BLAST search hits for CRISPR associated proteins in CRISPR/Cas containing plasmid pDCD537KLM.

| Gene | BLAST |
|---|---|
| cas10 | gb|AAW53330.1| CRISPR-associated protein, TM1811 family [*Staphylococcus epidermidis* RP62A] Length = 757 GENE ID: 3240723 SERP2461 | CRISPR-associated Csm1 family protein [*Staphylococcus epidermidis* RP62A] Score = 696 bits (1795), Expect = 0.0, Method: Compositional matrix adjust. Identities = 378/778 (49%), Positives = 520/778 (67%), Gaps = 45/778 (6%) |
| csm2 | gb|EFU73216.1| csm2 family CRISPR-associated protein [*Enterococcus italicus* DSM 15952] Length = 140 Score = 99.8 bits (247), Expect = 5e−25, Method: Compositional matrix adjust. Identities = 46/99 (46%), Positives = 70/99 (71%), Gaps = 0/99 (0%) |
| csm3 | gb|ADC86178.1| putative DNA repair protein, RAMP superfamily [*Staphylococcus lugdunensis* HKU09-01] emb|CCB52451.1| CRISPR associated RAMP family protein [*Staphylococcus lugdunensis* N920143] Length = 214 GENE ID: 8817736 SLGD_00030 | DNA repair protein, RAMP superfamily [*Staphylococcus lugdunensis* HKU09-01] Score = 201 bits (512), Expect = 4e−63, Method: Compositional matrix adjust. Identities = 119/210 (57%), Positives = 157/210 (75%), Gaps = 8/210 (4%) |
| csm4 | gb|AAW53327.1| CRISPR-associated protein, TM1808 family [*Staphylococcus epidermidis* RP62A] Length = 304 GENE ID: 3240720 SERP2458 | CRISPR-associated Csm4 family protein [*Staphylococcus epidermidis* RP62A] Score = 271 bits (693), Expect = 7e−88, Method: Compositional matrix adjust. Identities = 148/305 (49%), Positives = 204/305 (67%), Gaps = 17/305 (6%) |
| csm5 | gb|AAW53326.1| CRISPR-associated protein, TM1807 family [*Staphylococcus epidermidis* RP62A] Length = 340 GENE ID: 3240980 SERP2457 | CRISPR-associated Csm5 family protein [*Staphylococcus epidermidis* RP62A] Score = 215 bits (548), Expect = 7e−65, Method: Compositional matrix adjust. Identities = 131/330 (40%), Positives = 192/330 (58%), Gaps = 31/330 (9%) |
| csm6 | gb|AAW53325.1| hypothetical protein SERP2456 [*Staphylococcus epidermidis* RP62A] Length = 422. GENE ID: 3240979 SERP2456 | hypothetical protein. Score = 113 bits (282), Expect = 3e−27, Identities = 67/174 (39%), Positives = 103/174 (59%), Gaps = 5/174 (3%) |
| cas6 | gb|ADC86183.1| CRISPR-associated protein Cas6 [*Staphylococcus lugdunensis* HKU09-01] Length = 222. GENE ID: 8817741 SLGD_00035 | CRISPR-associated protein Cas6. Score = 169 bits (428), Expect = 4e−50, Identities = 82/219 (37%), Positives = 142/219 (65%), Gaps = 2/219 (1%) |
| cas1 | gb|ADC86174.1| CRISPR-associated protein Cas1 [*Staphylococcus lugdunensis* HKU09-01] Length = 301. GENE ID: 8817732 SLGD_00026 | CRISPR-associated protein Cas1. Score = 253 bits (647), Expect = 1e−81 Identities = 123/251 (49%), Positives = 177/251 (71%), Gaps = 8/251 (3%) |
| relE | >gb|EGV04250.1| addiction module toxin, RelE/StbE family [*Streptococcus infantis* SK970] Length = 112. Score = 65.9 bits (159), Expect = 1e−12, Method: Compositional matrix adjust. Identities = 40/110 (36%), Positives = 62/110 (56%), Gaps = 15/110 (14%) |

TABLE 6

Phage resistance phenotype comparison of host strains harboring

| Strain | Plasmid | Spacer Content | Efficiency of Plaquing |||
|---|---|---|---|---|---|
| | | | p2 | bIL170 | 949 |
| LM2345 | na | na | S | | |
| 2345LN | pDCD537LN | s1-s15 | R | | |
| 2345F8-2 | pDCD537LN::ISS1 (+pGhost9::ISS1) | s1-s8 s9::ISS1 s10-s15* | S | | |
| 1403-S4 | na | na | S | S | |
| 1403LN | pDCD537LN | s1-s15 | | R | R |
| 1403-S4F8-2 | pDCD537LN::ISS1 (+pGhost9::ISS1) | s1-s8 s9::ISS1 s10-s15* | | S | R |

S = Sensitive

R = Resistant

*ISS1 insertion into spacer s9 displaces spacers s10-s15, relative to the expected direction of CRISPR array transcription.

TABLE 7

Comparison of the 22-nt core sequence of spacer s3 with identity to lactococcal phage 4268 and corresponding protospacer region of wild type phages M5949, M5952 and corresponding CRISPR escape phages (m = mutated). The mutated nucleotide is indicated in bold and underline.

| | 22-nt core sequence in phage 4268 |
|---|---|
| s3 | CTGTTAATTTAACTCCCATTTG |
| M5949 | CTGTTAATTTAACTCCCATTTG |
| mM5949 | CAGTTAATTTAACTCCCATTTG |
| M5952 | CTGTTAATTTAACTCCCATTTG |
| mM5952 | CTGTTAATTTAACTGCCATTTG |
| Additional mM5952 escape phage (number of isolates) | |
| A (5) | CTGTTAATTTAACTTCCATTTG |
| B (49) | CTATTAATTTAACTCCCATTTG |
| C (1) | CTGTTAATTTAACTCCCATGTG |
| D (8) | CTTTTAATTTAACTCCCATTTG |
| E (3) | CTGTTAATTTAACACCCATTTG |

TABLE 7-continued

Comparison of the 22-nt core sequence of spacer s3 with identity to lactococcal phage 4268 and corresponding protospacer region of wild type phages M5949, M5952 and corresponding CRISPR escape phages (m = mutated). The mutated nucleotide is indicated in bold and underline.

|   | 22-nt core sequence in phage 4268 |
|---|---|
| F (3) | CTGTTAATTTAACTGCCATTTG |
| G (1) | CTGTTAATTTGACTCCCATTTG |
| H (2) | CTGTTAATTTAACGCCCATTTG |
| I (1) | CTGTTAATTTAACCCCCATTTG |

TABLE 8

List of primer sequences used for PCR and sequence reactions.

| Primer | Sequence (5' → 3') |
|---|---|
| 1F | TTAAGACTAGGATAGCACGAC |
| 1R | GTCAAGCACTCCTTCATTTGC |
| 2F | GCAAATGAAGGAGTGCTTGAC |
| 2R | GGACTACTGGGCTATCAACC |
| 3R | GTTGCATAAGTATCAGACTGG |
| 4F | CCAGTCTGATACTTATGCAAC |
| 5F | CAGCCGTAGGAGATACAGATC |
| 4RB | GTAGCAGTGGTCCATCGTGA |
| 5R | CCTCATAGAAAGAGAACCAATGA |
| 6F | TCATTGGTTCTCTTTCTATGAGG |
| cas1F | AGGTGACATGACGCTCAAAG |
| new cas1 | GGCTGATGCTGTTACCTTCACG |
| cas1R | CTCAAATACCAACACATCAACAA |
| CR-F1 | TTGTTGATGTGTTGGTATTTGAG |
| CR-R1 | CAATGGGCTAGATTGACCTA |
| CR-F2 | TAGGTCAATCTAGCCCATTG |
| CR-R2 | GAGTCTGTTGGTCTTATCCTTA |
| CR-F3 | TAAGGATAAGACCAACAGACTC |
| CR-R3 | GGTAGTTATTAGAGGTGCCC |
| S4R | TCCGAGGGAGTTGAAGCTTGGTTCAAAGAACGTATGTTCTCGTCCCCTTTTATCGAGGAGCGGTTGTATTTAGAGAACTTTAAAAACGTG |
| S4F | ATACGTTCTTTGAACCAAGCTTCAACTCCCTCGGAAAATACAACCGCTCCTCGATAAAAGGGGACGAGAACCATATGATTCAGGTATTGC |
| IS1194 | CATGTTCAATACGGACACGTA |
| RLa-F5 | CGATAAAAGGGGACGAGAAC |
| RLa-R6 | CCCCTTTTATYGAGGAGCGG |

REFERENCES

Altschul, S. F. and W. Gish, W. 1996. Local alignment statistics. Methods Enzymol. 266:460-480.

Altschul, S. F., W. Gish, W. Miller, E. W. Myers, and D. J. Lipman. 1990. A basic local alignment search tool. J. Mol. Biol., 215, 403-410.

Anderson, D. G., and L. L. McKay. 1984. Genetic and physical characterization of recombinant plasmids associated with cell aggregation and high-frequency conjugal transfer in *Streptococcus lactis* ML3. J. Bacteriol. 158: 954-962.

Ausubel, F. M., R. Brent, R. E. Kingston, D. D. Moore, J. G. Seidman, J. A. Smith, and K. Struhl, (eds.) 1995. Current Protocols in Molecular Biology. John Wiley & Sons, New York.

Barrangou, R., C. Fremaux, H. Deveau, M. Richards, P. Boyaval, S. Moineau, D. A. Romero, and P. Horvath. 2007. CRISPR provides acquired resistance against viruses in prokaryotes. Science 315: 1709-1712.

Bland, C., T. L. Ramsey, F. Sabree, M. Lowe, K. Brown, N. C. Kyrpides, and P. Hugenholtz. 2007. CRISPR Recognition Tool (CRT): a tool for automatic detection of clustered regularly interspaced palindromic repeats. BMC Bioinformatics. 8:209

Bolotin, A., B. Quinquis, A. Sorokin, and S. D. Ehrlich. 2005. Clustered regularly interspaced short palindrome repeats (CRISPRs) have spacers of extrachromosomal origin. Microbiol. 151:2551-2561.

Breitbart, M., and F. Rowher. 2005. Here a virus, there a virus, everywhere the same virus? Trends Microbiol. 13:278-284.

Brouns, S. J. J., M. M. Jore, M. Lundgren, E. R. Westra, R. J. H. Slijkhuis, A. P. L. Snijders, M. J. Dickman, K. S. Makarova, E. V. Koonin, J. van der Oost. 2008. Small CRISPR RNAs guide antiviral defense in prokaryotes. Science 321:960-964.

Brüssow, H.2001. Phages of dairy bacteria. Ann. Rev. Microbiol. 55:283-303.

Chibani-Chemoufi, S., A. Bruttin, M.-L. Dillmann, and H. Brüssow. 2004. Phage-host interaction: an ecological perspective. J. Bacteriol. 186: 3677-3686.

Chopin, A., M.-C. Chopin, A. Moillo-Batt, and P. Langella. 1984. Two plasmid-determined restriction and modification systems in *Streptococcus lactis*. Plasmid 11:260-263.

Crutz-Le Coq, A.-M., B. Cesselin, J. Commissaire. and J. Anba. 2002. Sequence analysis of the lactococcal bacteriophage bIL170: insights into structural proteins and HNH endonucleases in dairy Phages. Microbiol. 148:985-1001.

Clewell, D. B., S. E. Flannagan, L. O. Zitzow, Y. A. Su, P. He, E. Senghas, and K. E. Weaver. 1991. Properties of conjugative transposon Tn916, p. 39-44. In G. M. Dunny, P. Patrick, and L. L. Cleary (ed.), Genetics and molecular biology of streptococci, lactococci, and enterococci. American Society for Microbiology, Washington, D.C.

Deveau, H., R. Barrangou, J. E. Garneau, J. Labonte, C. Fremaux, P. Boyaval, D. A. Romero, P. Horvath, and S. Moineau. 2008. Phage response to CRISPR-encoded resistance in *Streptococcus thermophilus*. J. Bacteriol. 190, 1390-1400.

Devereux, J., P. Haeberli, and O. Smithies. 1984. A comprehensive set of sequence analysis programs for the VAX. Nuc. Acids Res. 12:387-395.

Dinsmore, P. K., D. A. Romero, and T. R. Klaenhammer. 1993. Insertional mutagenesis in *Lactococcus lactis* subsp. *lactis* mediated by IS946. FEMS Microbiol. Lett. 107:43-48.

Dougherty, B. A., C. Hill, J. F. Weidman, D. R. Richardson, J. C. Venter, and R. P. Ross. 1998. Sequence and analysis of the 60 kb conjugative, bacteriocin-producing plasmid pMRC01 from *Lactococcus lactis* DPC3147. Mol. Microbiol. 29:1029-1038.

Edgar, R. C. 2007. PILER-CR: fast and accurate identification of CRISPR repeats. BMC Bioinformatics 8:18.

Feng, D. F., and R. F. Doolittle. 1987. Progressive sequence alignment as a prerequisite to correct phylogenetic trees. J. Mol. Evol. 25:351-360.

Garneau, J. E., M.-È. Dupuis, M. Villion, D. A. Romero, R. Barrangou, P. Boyaval, C. Fremaux, P. Horvath, A. H. Magadán, and S. Moineau. 2010. The CRISPR/Cas bacterial immune system cleaves bacteriophage and plasmid DNA. Nature 468:67-71.

Grissa, I., G. Vergnaud, and Pourcel, C. 2007. The CRISPRdb database and tools to display CRISPRs and to generate dictionaries of spacers and repeats. BMC Bioinformatics 8, 172.

Groenen, P. M., A. E. Bunschoten, D. van Soolingen, and J. D. van Embden, 1993. Nature of DNA polymorphism in the direct repeat cluster of *Mycobacterium tuberculosis*; application for strain differentiation by a novel typing method. Mol. Microbiol. 10, 1057-1065.

Haft, D. H., J. Selengut, E. F. Mongodin, and K. E. Nelson, K. E. 2005. A guild of 45 CRISPR-associated (Cas) protein families and multiple CRISPR/Cas subtypes exist in prokaryotic genomes. PloS Comput. Biol. 1:474-483.

Hale, W. G., and J. P. Margham. 1991. The Harper Collins Dictionary of Biology, Harper Perennial, N.Y.

Heap, H. A., and R. C. Lawrence. 1976. The selection of starter strains for cheese making. N.Z.J. Dariy Sci. Technol. 11:16-53.

Heap H. A, and R. C. Lawrence. 1981. The contribution of starter strains to the level of phage infection in a commercial cheese factory. N.Z.J. Dairy Sci. Technol. 12:213-218.

Higgins, D. G., and P. M. Sharp. 1989. Fast and sensitive multiple sequence alignments on a microcomputer. Comput Appl Biosci. 5:151-153.

Hoe, N., K. Nakashima, D. Grigsby, X. Pan, S. J. Dou, S, Naidich, M. Garcia, E. Kahn, D. Bergmire-Sweat, and J. M. Musser. 1999. Rapid molecular genetic subtyping of serotype M1 group A *Streptococcus* strains. Emerg. Infect. Dis. 5, 254-263.

Horvath, P., and R. Barrangou. 2010. CRISPR/Cas, the immune system of bacteria and archaea. Science 327:167-170.

Horvath, P., A.-C. Coûté-Monvoisin, D. A. Romero, P. Boyava, C. Fremaux, R. Barrangou. 2009. Comparative analysis of CRISPR loci in lactic acid bacteria genomes. Int. J. Food Microbiol. 131:62-70.

Horvath, P., D. A. Romero, A.-C. Coûté-Monvoisin, M. Richards, H. Deveau, S. Moineau, P. Boyaval, C. Fremaux, and R. Barrangou. 2008. Diversity, activity, and evolution of CRISPR loci in *Streptococcus thermophilus*. J. Bacteriol. 190, 1401-1412.

Ishino, Y., H. Shinagawa, K. Makino, M. Amemura, A. Nakata. 1987. Nucleotide sequence of the iap gene, responsible for alkaline phosphatase isozyme conversion in *Escherichia coli*, and identification of the gene product. J. Bacteriol. 169, 5429-5433.

Jansen, R., J. D. van Embden, W. Gaastra, and L. M. Schouls. 2002. Identification of a novel family of sequence repeats among prokaryotes. OMICS 6:23-33.

Jansen, R., J. D. Embden, W. Gaastra and L. M. Schouls, 2002. Identification of genes that are associated with DNA repeats in prokaryotes. Mol. Microbiol., 43: 1565-1575.

Karginov, F. V., and G. J. Hannon. 2010. The CRISPR system: small RNA-guided defense in bacteria and Archaea. Molec. Cell 37:7-19.

Karlin, S, and S F Altschul. 1993. Applications and statistics for multiple high-scoring segments in molecular sequences. Proc. Nat. Acad. Sci. 90:5873-5877.

Klaenhammer, T. R. 1984. Interaction of bacteriophages with lactic streptococci. In Advances in Applied Microbiology, A. I. Laskin, ed., Vol 30, pp. 1-29. Academic Press, New York.

Krieger, M. 1990. Gene transfer and expression, a laboratory manual. Stockton Press, New York.

Lawrence, R. C., H. A. Heap, G. Limsowtin, and A. W. Jarvis. 1978. Cheddar cheese starters: current knowledge and practices of phage characteristics and strain selection. J. Dairy Sci. 61:1181-1191.

Lawrence, R. C., T. D. Thomas, and B E. Terzaghi. 1976. Cheese starters. J. Dairy Res. 43:141-193.

Limsowtin, G. K. Y., H. A. Heap, and R. C. Lawrence. 1978. Heterogeneity among strains of lactic streptococci. N.Z.J. Dairy Sci. Technol. 13:1-8.

Limsowtin, G. K. Y., and B. E. Terzaghi. 1976. Phage resistant mutants: their selection and use in cheese factories N.Z.J. Dairy Sci. Technol. 11:251-256.

Lukashin A. and M. Borodovsky. 1988. GeneMark.hmm for Prokaryotes (Version 2.8), GeneMark.hmm: new solutions for gene finding, Nuc. Acid Res. 26:1107-1115.

Maguin, E., H. Prévost, S. D. Ehrlich, and A. Gruss. 1996. Efficient insertional mutagenesis in lactococci and other Gram-positive bacteria. J. Bacteriol. 178:931-935.

Makarova, K. S., Grishin N V, Shabalina S A, Wolf Y I, Koonin E V. 2006. A putative RNA-interference-based immune system in prokaryotes: computational analysis of the predicted enzymatic machinery, functional analogies with eukaryotic RNAi, and hypothetical mechanisms of action. Biol. Direct 1, 7.

Makarova, K. S., D. H. Haft, R. Barrangou, S. J. J. Brouns, E. Charpentier, P. Horvath, S. Moineau, F. J. M. Mojica, Y. I. Wolf, A. F. Yakunin, J. van der Oost, and E. V. Koonin. 2011. Evolution and classification of the CRISPR-Cas systems. Nat. Rev. Microbiol. 9: 467-477

Marraffini, L. A., and E. J. Sontheimer. 2008. CRISPR interference limits horizontal gene transfer in staphylococci by targeting DNA. Science 322:1843-1845.

Marraffini, L. A., and E. J. Sontheimer. 2010. Self versus non-self discrimination during CRISPR RNA-directed immunity. Nature 463:568-571.

Masepohl, B., K. Gorlitz, and H. Bohme. 1996. Long tandemly repeated repetitive (LTRR) sequences in the filamentous cyanobacterium *Anabaena* sp. PCC 7120. Biochim. Biophys. Acta 1307, 26-30.

McKay, L. L., K. A. Baldwin, and P. M. Walsh. 1980. Conjugal transfer of genetic information in group N streptococci. Appl. Environ. Microbiol. 40:84-91.

Mojica, F. J., C. Díez-Villaseñor, C., E. Soria, E., and G. Juez, G. 2000. Biological significance of a family of regularly spaced repeats in the genomes of archaea, bacteria and mitochondria. Mol. Microbiol. 36, 244-246.

Mojica, F. J. M., C. Díez-Villaseñor, J. García-Martínez, E. Soria. 2005. Intervening sequences of regularly spaced prokaryotic repeats derive from foreign genetic elements. J. Mol. Evol. 60:174-182.

Mojica, F. J., C. Ferrer, G. Juez, and F. Rodriguez-Valera. 1995. Long stretches of short tandem repeats are present in the largest replicons of the *Archaea Haloferax mediterranei* and *Haloferax volcanii* and could be involved in replicon partitioning. Mol. Microbiol. 17, 85-93.

Mollet, B., S. Iida, J. Shepherd, and W. Arber. 1981. Nucleotide sequence of IS26, a new prokaryotic mobile genetic element. Nuc. Acids Res. 11:6319-6330.

Nakata, A., Amemura, M., and Makino, K. 1989. Unusual nucleotide arrangement with repeated sequences in the *Escherichia coli* K-12 chromosome. J. Bacteriol. 171, 3553-3556.

Needleman S. B., and C. D. Wunsch. 1970. A general method applicable to the search for similarities in the amino acid sequence of two proteins. J. Mol. Biol. 48:443-453.

Pearce, L. E. 1978. The effect of host-controlled modification on the replication rate of a lactic streptococcal bacteriophage. N.Z. J. Dairy Sci. Technol. 13:166-171.

Pearson, W. R., and D. J. Lipman. 1988. Improved tools for biological sequence comparison. Proc. Natl. Acad. Sci USA 85:2444-2448.

Pourcel, C., G. Salvignol, and G. Vergnaud. 2005. CRISPR elements in *Yersinia pestis* acquire new repeats by preferential uptake of bacteriophage DNA, and provide additional tools for evolutionary studies. Microbiol. 151:653-663.

Rajagopal, S. N., and W. E. Sandine. 1990. Associative growth and proteolysis of *Streptococcus thermophilus* and *Lactobacillus* bulgaricus in skim milk. J. Dairy Sci. 73:894-899.

Russell, W. M., and T. R. Klaenhammer. 2001. Efficient system for directed integration into the *Lactobacillus acidophilus* and *Lactobacillus gasseri* chromosomes via homologous recombination. Appl. Envir. Microbiol. 67:4361-4364.

Sambrook, J., E. Fritsch, and T. Maniatis. 1989. Molecular Cloning: A Laboratory Manual, $2^{nd}$ ed., Cold Spring Harbor Laboratory, New York.

Sanders, M. E., and T. R. Klaenhammer. 1980. Restriction and modification in Group N streptococci: effect of heat on development of modified lytic bacteriophage. Appl. Environ. Microbiol. 40: 500-506

Shah, S. A., Hansen, N. R., Garrett, R. A., 2009. Distributions of CRISPR spacer matches in viruses and plasmids of crenarchaeal acidothermophiles and implications for their inhibitory mechanism. Biochem. Soc. Trans. 37: 23-28.

Singleton, P., and D. Sainsbury. 2006. Dictionary of Microbiology and Molecular Biology, $3^{rd}$ ed, John Wiley and Sons, New York.

Smith, T. F. and M. S. Waterman. 1981. Comparison of biosequences. Adv. Appl. Math. 2: 482-489.

Sonnhammer, E. L. L., and R. Durbin. 1995. A dot-matrix program with dynamic threshold control suited for genomic DNA and protein sequence analysis. Gene 167: GC1-10.

Stanisich, V. A., P. M. Bennet, and M. H. Richmond. 1977. Characterization of a translocation unit encoding resistance to mercuric ions that occurs on a nonconjugative plasmid in *Pseudomonas aeruginosa*. J. Bacteriol. 129: 1227-1233

Stern, A. L., Keren, O. Wurtzel, G. Amitai, and R. Sorek. 2010. Self-targeting by CRISPR: gene regulation or autoimmunity? Trends Genet. 26: 335-340.

Sturino, J. M., and T. R. Klaenhammer. 2004. Bacteriophage defense systems and strategies for lactic acid bacteria. Adv. appl. Microbiol. 56:331-378.

Sturino, J. M., and T. R. Klaenhammer. 2006. Engineered bacteriophage-defence systems in bioprocessing. Nat. Rev. Microbiol. 4:395-404.

Thunell, R. K., W. E. Sandine, and F. W. Bodyfelt. 1981. Phage-insensitive, multiple-strain starter approach to cheddar cheese making. J. Dairy Sci. 64:2270-2277.

Trotter, M., O. McAuliffe, M. Callanan, R. Edwards' G. F. Fitzgerald, A. Coffey, and R. P. Ross. 2006. Genome analysis of the obligately lytic bacteriophage 4268 of Lactococcus lactis provides insight into its adaptable nature. Gene 366:189-199.

van Embden, J. D. A, T. van Gorkom, K. Kremer, R. Jansen, B. A. M. van der Zeijst, and L. M. Schouls. 2000. Genetic variation and evolutionary origin of the direct repeat locus of Mycobacterium tuberculosis complex bacteria. J. Bacteriol. 182: 2393-2401.

Whitehead, H. R., and G. J E. Hunter. 1947. Bacteriophage in cheese manufacture: contamination from farm equipment. J. Dairy Res. 15:112-119.

---

The invention claimed is:

1. A transformed host cell resistant to a target nucleic acid or a transcription product thereof, the host cell comprising:
   a) at least one *Lactococcus* cas gene encoding an amino acid sequence selected from the group consisting of SEQ ID Nos 4, 6, 8, 10, 12, 14, 16, 18 or 20;
   b) at least two *Lactococcus* CRISPR repeats as defined in SEQ ID No: 24, and
   c) a spacer flanked by two of the at least two *Lactococcus* CRISPR repeats, wherein said spacer is homologous to a target nucleic acid or transcription product thereof, wherein the at least two CRISPR repeats, the spacer and the at least one *Lactococcus* cas gene form a functional combination that confers resistance to the target nucleic acid
   wherein said host cell is selected from the group consisting of a *Bifidobacterium* species, a *Brevibacterium* species, a *Propionibacterium* species, a *Lactococcus* species, a *Streptococcus* species, a *Lactobacillus* species including the *Enterococcus* species, *Pediococcus* species, a *Leuconostoc* species and *Oenococcus* species, and wherein when the host cell is a *Lactococcus* species, this host cell is selected from the group consisting of *Lactococcus chungangensis*, *Lactococcus fujiensis*, *Lactococcus garvieae*, *Lactococcus lactis* subsp. *hordniae*, *Lactococcus lactis* subsp. *tructae*, *Lactococcus piscium*, *Lactococcus plantarum* and *Lactococcus raffinolactis*.

2. The host cell according to claim 1 wherein said target nucleic is the nucleic acid of a phage and said transformed host cell has an increased resistance to the phage as compared to a non-transformed cell.

3. A method for preparing a transformed host cell resistant to a phage comprising:
   (a) preparing a nucleic acid or a vector comprising:
   1) at least one *Lactococcus* cas gene encoding an amino acid sequence selected from the group consisting of SEQ ID Nos: 4, 6, 8, 10, 12, 14, 16, 18 or 20;
   2) at least two *Lactococcus* CRISPR repeats as defined in SEQ ID No: 24, and
   3) a spacer flanked by two of the at least two *Lactococcus* CRISPR repeats, wherein said spacer is homologous to the target nucleic acid wherein said target nucleic is the nucleic acid of a phage and said transformed host cell has an increased resistance to the phage as compared to a non-transformed cell; and
   b) transforming a host cell sensitive to the phage with the nucleic acid or vector of step a),
   wherein said host cell is selected from the group consisting of a *Bifidobacterium* species, a *Brevibacterium* species, a *Propionibacterium* species, a *Lactococcus* species, a *Streptococcus* species, a *Lactobacillus* species including the *Enterococcus* species, *Pediococcus* species, a *Leuconostoc* species and *Oenococcus* species, and wherein when the host cell is a *Lactococcus* species, this host cell is selected from the group consisting of *Lactococcus chungangensis*, *Lactococcus fujiensis*, *Lactococcus garvieae*, *Lactococcus lactis* subsp. *hordniae*, *Lactococcus lactis* subsp. *tructae*, *Lactococcus piscium*, *Lactococcus plantarum* and *Lactococcus raffinolactis*.

4. The method according to claim 3, wherein the *Lactococcus* CRISPR spacer sequence is selected from at least one of SEQ ID NOs: 25-60 or a sequence having at least 95% identity to any one of SEQ ID Nos: 25 to 60.

5. The method according to claim 3, wherein the nucleic acid comprises a repeat-spacer unit sequence, wherein the spacer sequence is selected from at least one of SEQ ID NOs: 25 to 60 or a sequence having at least 97% identity to any one of SEQ ID Nos: 25 to 60.

6. The method according to claim 4, wherein the nucleic acid comprises SEQ ID NO: 22 or a portion thereof comprising at least 200 nucleotides.

7. The method according to claim 3, wherein the at least one *Lactococcus* cas gene is a sequence having at least 95% identity to SEQ ID No: 3, 5, 7, 9, 11, 13, 15, 17, and/or 19 over the full length of the sequences.

8. The method according to claim 3 wherein the host cell selected from the group consisting of a *Bifidobacterium* species, a *Brevibacterium* species, a *Propionibacterium* species, a *Streptococcus* species, a *Lactobacillus* species including the *Enterococcus* species, a *Pediococcus* species, a *Leuconostoc* species and a *Oenococcus* species.

9. The method according to claim 3 wherein the host cell is selected from the group consisting of a *Lactococcus chungangensis, Lactococcus fujiensis, Lactococcus garvieae, Lactococcus lactis* subsp. *hordniae, Lactococcus lactis* subsp. *tructae, Lactococcus piscium, Lactococcus plantarum* and *Lactococcus raffinolactis* strain.

10. A phage-resistant bacterial strain obtained using the method according to claim 3.

11. A cell culture comprising a host cell according to claim 1.

12. The cell culture according to claim 11, wherein the cell culture is a bacterial culture selected from the group consisting of a starter culture, a probiotic culture, a dietary supplement culture.

13. A product comprising the cell culture of claim 11.

14. The product according to claim 13 wherein said product is selected from the group consisting of: a food product, a feed product, a personal care product, a health care product, a veterinary product and a dietary supplement.

15. The host cell according to claim 1, wherein the target nucleic acid or transcription product thereof is from a phage.

16. The host cell according to claim 1, wherein the at least one *Lactococcus* cas gene, the at least two *Lactococcus* CRISPR repeats and the spacer are on the same nucleic acid.

17. The host cell according to claim 1 wherein the at least one *Lactococcus* cas gene, the at least two *Lactococcus* CRISPR repeats and the spacer are on a vector.

18. The host cell according to claim 17, wherein said vector is a plasmid.

19. The host cell according to claim 1, wherein the at least one *Lactococcus* cas gene, the at least two *Lactococcus* CRISPR repeats and the spacer are integrated into the host cell genome.

20. The host cell according to claim 1 wherein the at least one *Lactococcus* cas gene is a sequence having at least 95% identity to SEQ ID No: 3, 5, 7, 9, 11, 13, 15, 17, and/or 19 over the full length of the sequences.

21. The host cell according to claim 1 wherein the at least one *Lactococcus* cas gene is a sequence having at least 97% identity to SEQ ID No: 3, 5, 7, 9, 11, 13, 15, 17, and/or 19 over the full length of the sequences.

22. The host cell according to claim 1 wherein the at least one *Lactococcus* cas gene is a sequence having at least 98% identity to SEQ ID No: 3, 5, 7, 9, 11, 13, 15, 17, and/or 19 over the full length of the sequences.

23. The host cell according to claim 1 wherein the at least one *Lactococcus* cas gene is a sequence having at least 99% identity to SEQ ID No: 3, 5, 7, 9, 11, 13, 15, 17, and/or 19 over the full length of the sequences.

24. The host cell according to claim 1, wherein the host cell comprises at least one *Lactococcus* cas gene selected from the group consisting of SEQ ID Nos: 3, 5, 7, 9, 11, 13, 15, 17, and 19.

25. A cell culture comprising a host cell according to claim 24.

26. The cell culture according to claim 25, wherein the cell culture is a bacterial culture selected from the group consisting of a starter culture, a probiotic culture, a dietary supplement culture.

27. A product, wherein:
the product comprises the cell culture of claim 25; and
the product is selected from the group consisting of: a food product, a feed product, a personal care product, a health care product, a veterinary product and a dietary supplement.

* * * * *

SEQUENCE LISTING

<160> NUMBER OF SEQ ID NOS: 60

<210> SEQ ID NO 1
<211> LENGTH: 9873
<212> TYPE: DNA
<213> ORGANISM: Lactococcus lactis

<400> SEQUENCE: 1

```
tcgtgcgctt tctaattctt agtggtttaa gactaggata gcacgactta tatattttc      60 aatgaaatca actagcaatt cgggtttata atgtgtttat ttatggaaaa aattatcatt    120
aaaaatcaag aaaatagttg gcaaacaaga ttgtttaacg taaaataata tcctttacca    180
aaaaaggtag aaagaatttt atggacaaaa taaatttagt atgtggttca cttttacacg    240
atattggaaa aattatttat cgtggtacta gcgaacgagc aaagcactct aaacttggtg    300
gagatttcat caaatccttt gagcaattta gaaatacaga attgactgat tgtatccgat    360
atcatcatgc ccaagaaatc acatctgtga aatcaaataa ggaaaaaaac tcactgtttt    420
atataactta tatcgctgat aacatttcat cgggtatgga tagacgaaaa gatttggaag    480
aaggtgcaga aggatttaat tgggataaaa aagttgcgct tggtagtgtt tttaatgtac    540
tgaacgaaaa agaaaaggga cggcaaaact attcatatcc gtttgtggca agaacacgga    600
taaaagaaga gccactaaat tttccaactg ctactcaaaa tcagtataca acttcctatt    660
atgacggttt aattactgat atgaaaacga ttttacagcg acttaagcca gataaggaac    720
acatcaactc tttgctgcaa atgatggaaa gtctgtggtc ttacgtccca agttcgactg    780
ataaaaatca gttggttgat atttctcttt acgaccattc gagaacgact gcggcgattg    840
caagtgctat ttatgactat tttcaggcag aaaatatcac tgattatcaa aaagaattat    900
ttgattataa tgctacggaa ttttatgata aaaatgcctt tttgatgatg aattttgata    960
tgagcggtgt tcagaatttt atttataata tttctggtag taaagctttg aaatcgttac   1020
gagcgcgaag tttttatctg gatatgttgt tggaatatat ttctgataat ttactcgaaa   1080
aactggaatt atctcgtgct aatattctat atgttggtgg cggtcatgcc tatcttttat   1140
tagccaatac gaacaaaact aaggctattt tatctgattt tgagcatgac ttaaaaacat   1200 ggttttttgga taaattcaag atagatttgt atgttgcaat ggcttataca gaagtttctg   1260
ctaatgactt gatgaatcat aatggtcatt accgtgatat ttatcgtcgt ttatcccaaa   1320
aaacatcagc taagaaagct aaccgctata ctgctgaaga aattttaaat ttaaaccatc   1380
aaggtacgga aaatgctcgt gagtgtcgcg aatgtaaacg aagtgattta ttgatagaag   1440
aagatgatat ttgtgaaatt tgtgatagtc tacaaaaagt ttcgagagat ttgacaagag   1500
aaaatatttt tgtgattgca aatgaaggag tgcttgacat gccttttggt aaaaagatgt   1560
```

```
ctgcactatc ttatagtcaa gctgataagc taaagaaaag caatgccgaa gttcaaattt    1620
atgccaagaa catctctgaa attggacaaa atttgatgac acgaattgat atgggagatt    1680
atacttatcg ttcagacttt catgaaatgt tagaagaagt tgaagtaggc atcaatcgtc    1740
taggcgtact tcgagcagat gttgataatc ttggtcaagc ctttattaac ggtattccag    1800
atgactattt gtcaatctct agaaccgcaa cattctcacg tgccatgagt agatttttca    1860
aaaattatct caatcaactt ttggctgaga aaagctataa aatcaacgtt atttatgctg    1920
gcggtgatga cttattcatg attggcgctt ggcaagatat tttagatttt tcgattgtgc    1980
ttaagcaaaa gtttgctgac tttacacaaa ataaattgtc gatttctgca ggtattggca    2040
tgttcagaga aaaatatcct gtggctagaa tggcaagtct gacaggagat ttagaggacg    2100
cagcaaagga ctataagcct gatgaaagag ctgtccaagc aacaaaaaat gcggtgacat    2160
tatttgatgc tacaaatgtc ttttcgtggg acacacttga aaatgatatt tttgtcaagc    2220
ttgatgccat tactaagaat tttgagaagc ttgatgaaac tggtaaggca tttatctacc    2280
gcctaattga tttgttgcgt ggggtaaatg agaatcagca aatcaacatt gcacgacttg    2340 cttatacccct ttcgagaatg gaagaaaaaa ttggcaaaac atttgctcaa gagctttata    2400
actgggcaaa tgctgataga aaaacattga taatggcact tgaaatttat atattgaaaa    2460
cgagggagag ataatgactg aattaaaaat cggtaatgag aaggtgaact caacgaactt    2520
tggagatttt gccgaaaaag caatcagagg gattaatcac aaaccatttg ttaattcaaa    2580
aggaggtgag caaaaaatta cgacatcaaa aattcgtggt atttttagaac tggtaaacaa    2640 agtttataat cgtgtcataa atactaatga tgttgaactt tcagaaaata ttttagctga    2700
tattgcgtat atcaaagtaa aaatcgctta tgaatcaggt cgcgaacctg ttgtgaaaga    2760
ttttattcaa agaacagcat ttaccgctgc aattactgat gtgatgaatc aaagaacccg    2820
cgaaagtttc ttgttattcg cacgttatgt tgaaagtttg attgcctatt ttaaattta    2880 cggagggaaa gattaatgaa attagtaata gaaggaacga ttgttcttaa aacaggtatg    2940
cacattggtg gttctagtga tttttcggcg attggtgcgg ttgatagccc agtagtccga    3000
gatacgctga cacgtttacc gctcattcca ggaagttcac ttaaaggtaa aatgcgatat    3060
ttgcttgcaa aagagttgaa taatggtatt ttgttgaatg aaccaaataa cgatcaagac    3120
gaaattttgc gactttttgg gtcatcagaa aaagataaga ttcgtcgcgc tcgtctgaaa    3180
ttcaatgata ttaagttatc caatttggct gaacttgaaa ctttcaatgt ctcatcaaca    3240
gaagtgaagt tgaaaatac gataaataga aaaactgctg ttgctaatcc tcgtcaaatt    3300
gaacgggtga ttgcaggttc aaaattcgat ttcgaaatct tctataatct tgatgatata    3360
aaggaagttg agaaggactt tgaaatatt aaacaggggt ttgatttact agagtttgac    3420
tacctaggtg gtcatgggac acgtggtagt ggtcgtattg catttgaaaa tttgtcagtc    3480
ataacagccg ttgggaactt tgaaaaaata aatactttaa atgaaatctt aggagcttga    3540
tatgaaaatt atcaaattat atttgaaag tccagttcat tttggtgaaa agcgcctatc    3600
ggagagcaaa ataactttt cggcagatac cttatttca gctttgatga tcgaggcggt    3660
tggacttgaa aaagaagatg aattttatca acttgcttca aataatctcg tcaaattttc    3720
agatgctttc ccttttattg atcaatatta ctatatacca aaaccaatgt tcaatcttaa    3780
attggaaaaa gaagatgaaa atccgtctaa agcttttaaa aaattgctct atgttccgat    3840
agatagttta gaggattatt tatcaggtgg attagatgct tacttgaaa gagaaagctt    3900 taatttagga aaacttgcct tatcggaaaa agttcaacag catgatttta aggactctga    3960
```

```
accttacaat gttggcacat ttaccttcaa agaaaataca ggtctttatg tcttgataga   4020
acagactcac ccattattag aggaattatt agaaaaccct tcaatattcag gaataggtgg   4080
taaacgaaat tcaggctatg gaaaatttaa gtttgaaata ctagaggatt cagacattga   4140
ggacttgttt tcggcaaaag gtaatcgaaa aatttttactt tccggtgcct tacccaaaga   4200
tgcagagctt gaacaagccc taaaaaatgc ctcatatctt ttagaacgtc gaggaggttt   4260
tgtccagtct gatacttatg caacaaatct tgtcaaaaaa caagatctat atgttttcaa   4320
aagcggttca acattcgaaa atagctttga cggagacatt tatcaagtag gcaaaaaagg   4380
aaatcatcca gtctataaat atgcgaagtc atttttcttg gaggttagtg tatgaagaag   4440
acatatcgag tgactttaac tgcacttgga ccgattttta ttggcggggg tgagaagctt   4500
aaaaagtatg agtatatttt tgataaacaa aaaaaagttg cacatatgat tgatcatacg   4560
aagtttacta atacttgtt agaaaaaaat ctattagacg atttcacgag tcgagtcaat   4620
tctcattttg atttatatga ttatttagtc aataaaaaag gaattgtttt catgccatta   4680
gttaagtatt cagtacctgt tgctcaattt agaacagagg taaaaaatag gtttggtaaa   4740
cctatttcta gccctccaat gaatgatttg aataccttttg tcaaagatgc ttttggtaga   4800
ccatatattc caggtagttc tttaaaaggc gctttacgca cagcgatttt gaatgattta   4860
aaggaagata cgaaagaaaa tgaagtcttt gcccatttac aggtatcaga tagtgaaacc   4920
attgaccttg aaaatcttaa ggtttatcaa aaagttgatt attctaaaac ggcaaaaccc   4980
ttgccgcttt atcgagaatg cctgaaaccg aatactgaaa ttactttttac agtatctttt   5040
gatgatgaat atttaacact taaaaaaatt caaaatgctt tgcataaaac ctatcagcat   5100
tattatatta aatggttaaa gggtggaaaa gttggagaaa cttttgataaa gggtgtttat   5160
gatagtcatg ctgacgagtt aaagaaaaat acttttgcat tggatcaacc aagtcaaaat   5220
caaggtgaga tcatttatat cggtggcggt gcagggttttg ttagtaagac cttacattat   5280
aaatcaaaaa atcgcgatca agctcgtaat gattcttttg atatttttaaa acagctattt   5340
cgtacaacct acagcaagat gcgttcggta cctgacaatg tcccagttgc tttgaaattg   5400
gctgttgaaa ctaaaacttt taacgggcga gtgacaggga aacactatct tgaaatgggg   5460
aaagcaagaa taaaattgga ggaattgaaa tgaaaatatt gatttcagcc gtaggagata   5520
cagatcctat acgtaatttt cacgatggac cactgctaca tattgtaaga gtttatcgtc   5580
ctgaaaaaat tgttttagtc catagtgaga gaagtttgac taagcatgac aaacttgtca   5640
aggcattgaa aagtatcaaa gactattcac ctgaaatcat tcaagatggg gtcgttttac   5700
cagatgcgca agttgccatc tttgatgaga tgtatgatac tgtatcaagt attgttaaaa   5760
aatatatatc tgatgatgaa attatcttaa atatctccag tgcgacaccg caaatcatca   5820
gtgctatgtt tgcggtgaat cgtatctctg atttaatgt cacagctgtt caagttaaga   5880
caccgcagca taagtcaaac gaagggctgc ggcatgataa tcaagaagat attgataaat   5940
tgattgagac gaatcttgat aatcagtctg attatgagaa tagaacactt gcagatactg   6000
gtatgaaatt ttcacaagat ttgacgaaac gaaatttaaa agctttgatt gataattatg   6060
attatcaggg agctttagaa cttcttaaaa aacagaaatc attttcaaat attaaggagt   6120
taagaaaaaa attaacagag atttcagata caatcaaaat tcaaggaatg ccagataaaa   6180
tcgttaaatc taaattatcc aatcaagcaa agagtgcttt aaattcctat ttaaatattg   6240
accgaaatca caagcaaggt aatattgcag aggtgttgat tcgagtaaaa tctccttgtag   6300
```

```
aatttatttt agaagattat ctaaataatc attttttaga tgtcatcact tacaaagatg    6360
gcaaaccatt tttaaatgct tcaaaatatc ctgagattct gaaaaagttt caggaagatg    6420
ccgaaatgag gggtaaggaa taccatagcg gttatttgag cctccctgct tacattggta    6480
ttctcaaatt tttcgaacca aatcatgact tattaaaaca tatttataag attcaagaaa    6540
ttaaccaaga cagaaataaa gtagcgcaca gtctacaagc ttttgatagg aaaaatttga    6600
agaaagtatc tagcgcagtt tttgcaagta aacaaattct gttagcttct tttgacattg    6660
ataatcattg gttctctttc tatgaggatt taaatcagga aataaaaaaa ttactatgat    6720
cgttaaactc cgatacaaaa taaacctgcc aaattcgctt cgtacccaaa acatcgggag    6780
cactctccat ggtgttttga tggaattatt acccagtgaa ctggtagagc accttcataa    6840
cttaagctac aatccatttc gtcagagatt aattttgaa aaagagctag tcatttggga     6900
aattgtgggc ttgcacaaaa tggtctcgga agagctgtta aaactcgaaa atttaaggga    6960
aataacaatc aaacgtgccc aaaagactgt tccttatcc ttactctcca aagatgcaat     7020
cgcagttgat gatttggtga aaaagaaat gggacgcgaa attgacagtc gaattatctc     7080
gcttaaattt acaagtccaa cctcatttaa agccaatggg cattatgaca ttttccaga     7140 tattcgaaaa attttccgtt ctttaatgat gaattttgat ttttttagtg aaacaactaa    7200
aatttatgat tacgaggttt tgtcgtacat tgaagaaaat gtccatattg tcagctataa    7260
attgatgaca aagaattttc atctcgagaa gataaaagta aaaggttttc aaggtgacat    7320
gacgctcaaa gtaactggcg cagaacagtt cgtaaaatta gtcttactta tgatcaaata    7380
tgcgactttc gcaggcattg gtatgaaaac aagccttggt atgggaggag tttccatcaa    7440
tgagagacat tatctacgtt gaaaataggt attttatcag tagtcgagaa aatgcgctca    7500
gatttcatga ctatattaat aaagcgaccc atttcattgc ttttgatgac attgatattt    7560
tagttttgga taatgcaaga agttacttgt caaatggtgt gattaacgac tgtttggatc    7620
gaaatatttt gattttaact tgcgataata acattctcc taaagcgatt ttaagcaatg      7680
cttttgctaa taaaaacgc ttagaacgct taagaaatca attgcaatta tcctctaagt      7740
caaagaatcg tctttggcgt aaaattgtga tggcgaaaat taataatcag gctgatgctg    7800
ttaccttcac ggttcaagat ggaacagttc atcgagagat aattgaacta ggaaaaatgg    7860
tcacagaagg agataaagat aatcgcgaag ctgtcgttgc acgaaaatat tttcggacat    7920
tatttggtgg taattttaag cgtggtcgtt ttgatgatgt catcaattca gcgctcaatt    7980
atggctatgc acttgtgagg gctgtcatca gacgagaatt ggctatctgt ggttttgaga    8040
tgagctttgg tattcatcat atgtcaacag aaaatccttt taatctctct gatgatatga    8100
ttgaagtttt tcggccttt gttgatgtgt tggtatttga gataattgtg acgaactaca      8160
agcggaagtt caaagggct atcaaagttt tttaactgaa aaacactatt cactttctga      8220
catgcgtaag gattttggca tcaatggcgc atgaatttaa acttgtattc tcagaagaat    8280
ctaaacgtta tttaaagaag atttacgact acattgtttt aaatttcttc tctgaaattt    8340
ctgctcgtag aaaagttgac ttacttttgt taggaagtga agtgttggag aaaattccag    8400
aattaggttt tgatgttttt caaaagacag gtaaaaaatt tctgggaatg gaaaatattc    8460
ggattctagt gattgaaaaa tatttggcag tttatcagat tgattttgaa gaaaacacaa    8520
tcaatatttt tcgttttta aatattaaaa ccaattattt acggtacttg agatagcttt      8580
ttactttgat ttttgctata cttaagaaat aacaattaaa cttttcaat ctacctgtag      8640 gtcaatctag cccattgttt tggtcgatat ttgaccaaga caatagcgcg gaaaagctta    8700
```

```
ctacaaacac gttttttaaag ttctctaaat acaaccgctc ctcgataaaa ggggacgaga    8760
actgcatgtt tatagccctg ccggatttta agctgcgaaa tacaaccgct cctcgataaa    8820
aggggacgag aactttccat tccgttaac tgctgccaga agatttcat caaatacaac      8880 cgctcctcga taaaggggga cgagaactgg ttgttgtcat tagctgtatc gtgaatgacg    8940
atataaaata caaccgctcc tcgataaaag gggacgagaa caacttggaa tggtaattca    9000 tataatttt tcataaaata caaccgctcc tcgataaaag gggacgagaa ctgctggttt     9060
tatttgctca atttttgaat tgtcaaaaat acaaccgctc ctcgataaaa ggggacgaga    9120
actttgttgt aaaatatttc atgttttgtt ttctcttttc taaatacaac cgctcctcga    9180
taaaggggga cgagaacaga gagtattcag tcatgaatga aatgattgca atttgaaata    9240
caaccgctcc tcgataaaag gggacgagaa cacaactgtt ttaactctat cctgatatat    9300
aaacccaaat acaaccgctc ctcgataaaa ggggacgaga acaactttt aaggataaga    9360 ccaacagact ctgacaaata caaccgctcc tcgataaaag gggacgagaa ctttatttgt    9420
ggcaacaagt tcagcaataa tagggtttaa atacaaccgc tcctcgataa aagggggacga   9480 gaacgaactt agcaagctat tttgtttctt ttcaagagcc aaaatacaac cgctcctcga    9540
taaaggggga cgagaacata cgttctttga accaagcttc aactccctcg aaaatacaa     9600 ccgctcctcg ataaaggggg acgagaactt ctgttaattt aactcccatt tgttagttct    9660
cctaaataca accgctcctc gataaaaggg gacgagaact ttttaaaatg ttgcaaatgt    9720
ttagctactt catgaaatac aaccgctcct cgataaaagg ggacgagaac atatgtcggt    9780 ttgtctttg gtctaacgta tgcaaaatac aaccgctcct cgataaaagg gggacgagaac    9840 catatgattc aggtattgct tctacaccaa gtt                                  9873

<210> SEQ ID NO 2
<211> LENGTH: 200
<212> TYPE: DNA
<213> ORGANISM: Lactococcus lactis

<400> SEQUENCE: 2
tcgtgcgctt tctaattctt agtggtttaa gactaggata gcacgactta tatattttc      60 aatgaaatca actagcaatt cgggtttata atgtgtttat ttatggaaaa aattatcatt    120
aaaaatcaag aaaatagttg gcaaacaaga ttgttaacg taaaataata tcctttacca    180
aaaaaggtag aaagaatttt                                                200

<210> SEQ ID NO 3
<211> LENGTH: 2274
<212> TYPE: DNA
<213> ORGANISM: Lactococcus lactis

<400> SEQUENCE: 3
atggacaaaa taatttagt atgtggttca cttttacacg atattggaaa aattatttat     60
cgtggtacta gcgaacgagc aaaagcactct aaacttggtg gagatttcat caaatccttt   120
gagcaattta gaaatacaga attgactgat tgtatccgat atcatcatgc ccaagaaatc    180
acatctgtga atcaaataa ggaaaaaaac tcactgtttt atataactta tatcgctgat    240
aacatttcat cgggtatgga tagacgaaaa gatttggaag aaggtgcaga aggattaat    300 tgggataaaa aagttgcgct tggtagtgtt tttaatgtac tgaacgaaaa agaaagggga   360
cggcaaaact attcatatcc gttgtgtggca agaacacgga taaagaaga gccactaaat   420
```

```
tttccaactg ctactcaaaa tcagtataca acttcctatt atgacggttt aattactgat    480
atgaaaacga ttttacagcg acttaagcca gataaggaac acatcaactc tttgctgcaa    540
atgatggaaa gtctgtggtc ttacgtccca gttcgactg ataaaaatca gttggttgat    600
atttctcttt acgaccattc gagaacgact gcggcgattg caagtgctat ttatgactat    660
tttcaggcag aaaatatcac tgattatcaa aagaattat ttgattataa tgctacggaa     720
ttttatgata aaaatgcctt tttgatgatg aatttttgata tgagcggtgt tcagaatttt   780
atttataata tttctggtag taaagctttg aaatcgttac gagcgcgaag tttttatctg    840
gatatgttgt tggaatatat ttctgataat ttactcgaaa aactggaatt atctcgtgct    900
aatattctat atgttggtgg cggtcatgcc tatcttttat tagccaatac gaacaaaact    960
aaggctattt tatctgattt tgagcatgac ttaaaaacat ggttttttgga taaattcaag   1020 atagatttgt atgttgcaat ggcttataca gaagtttctg ctaatgactt gatgaatcat    1080
aatggtcatt accgtgatat ttatcgtcgt ttatcccaaa aaacatcagc taagaaagct    1140
aaccgctata ctgctgaaga aattttaaat ttaaaccatc aaggtacgga aaatgctcgt    1200
gagtgtcgcg aatgtaaacg aagtgattta ttgatagaag aagatgatat ttgtgaaatt    1260
tgtgatagtc tacaaaaagt ttcgagagat ttgacaagaa aaatatttt tgtgattgca    1320 aatgaaggag tgcttgacat gccttttggt aaaaagatgt ctgcactatc ttatagtcaa    1380
gctgataagc taaagaaaag caatgccgaa gttcaaattt atgccaagaa catctctgaa    1440
attggacaaa atttgatgac acgaattgat atgggagatt atacttatcg ttcagacttt    1500
catgaaatgt tagaagaagt tgaagtaggc atcaatcgtc taggcgtact tcgagcagat    1560
gttgataatc ttggtcaagc ctttattaac ggtattccag atgactattt gtcaatctct    1620
agaaccgcaa cattctcacg tgccatgagt agatttttca aaaattatct caatcaactt    1680
ttggctgaga aaagctataa aatcaacgtt atttatgctg gcggtgatga cttattcatg    1740
attggcgctt ggcaagatat tttagatttt tcgattgtgc ttaagcaaaa gtttgctgac    1800
tttacacaaa ataaattgtc gatttctgca ggtattggca tgttcagaga aaaatatcct    1860
gtggctagaa tggcaagtct gacaggagat ttagaggacg cagcaaagga ctataagcct    1920
gatgaaagag ctgtccaagc aacaaaaaat gcggtgacat tatttgatgc tacaaatgtc    1980
ttttcgtggg acacacttga aaatgatatt tttgtcaagc ttgatgccat tactaagaat    2040
tttgagaagc ttgatgaaac tggtaaggca tttatctacc gcctaattga tttgttgcgt    2100
ggggtaaatg agaatcagca atcaacatt gcacgacttg cttatacccct ttcgagaatg    2160 gaagaaaaaa ttggcaaaac atttgctcaa gagctttata actgggcaaa tgctgataga    2220
aaaacattga taatggcact tgaaatttat atattgaaaa cgagggagag ataa           2274
```

<210> SEQ ID NO 4
<211> LENGTH: 757
<212> TYPE: PRT
<213> ORGANISM: Lactococcus lactis

<400> SEQUENCE: 4

Met Asp Lys Ile Asn Leu Val Cys Gly Ser Leu Leu His Asp Ile Gly
1               5                   10                  15

Lys Ile Ile Tyr Arg Gly Thr Ser Glu Arg Ala Lys His Ser Lys Leu
            20                  25                  30

Gly Gly Asp Phe Ile Lys Ser Phe Glu Gln Phe Arg Asn Thr Glu Leu
        35                  40                  45

```
Thr Asp Cys Ile Arg Tyr His His Ala Gln Glu Ile Thr Ser Val Lys
 50                      55                      60

Ser Asn Lys Glu Lys Asn Ser Leu Phe Tyr Ile Thr Tyr Ile Ala Asp
 65                      70                      75                      80

Asn Ile Ser Ser Gly Met Asp Arg Arg Lys Asp Leu Glu Gly Ala
                 85                      90                      95

Glu Gly Phe Asn Trp Asp Lys Lys Val Ala Leu Gly Ser Val Phe Asn
                100                     105                     110

Val Leu Asn Glu Lys Glu Lys Gly Arg Gln Asn Tyr Ser Tyr Pro Phe
             115                     120                     125

Val Ala Arg Thr Arg Ile Lys Glu Glu Pro Leu Asn Phe Pro Thr Ala
 130                     135                     140

Thr Gln Asn Gln Tyr Thr Thr Ser Tyr Tyr Asp Gly Leu Ile Thr Asp
 145                     150                     155                     160

Met Lys Thr Ile Leu Gln Arg Leu Lys Pro Asp Lys Glu His Ile Asn
                 165                     170                     175

Ser Leu Leu Gln Met Met Glu Ser Leu Trp Ser Tyr Val Pro Ser Ser
             180                     185                     190

Thr Asp Lys Asn Gln Leu Val Asp Ile Ser Leu Tyr Asp His Ser Arg
     195                     200                     205

Thr Thr Ala Ala Ile Ala Ser Ala Ile Tyr Asp Tyr Phe Gln Ala Glu
 210                     215                     220

Asn Ile Thr Asp Tyr Gln Lys Glu Leu Phe Asp Tyr Asn Ala Thr Glu
 225                     230                     235                     240

Phe Tyr Asp Lys Asn Ala Phe Leu Met Met Asn Phe Asp Met Ser Gly
                 245                     250                     255

Val Gln Asn Phe Ile Tyr Asn Ile Ser Gly Ser Lys Ala Leu Lys Ser
             260                     265                     270

Leu Arg Ala Arg Ser Phe Tyr Leu Asp Met Leu Leu Glu Tyr Ile Ser
     275                     280                     285

Asp Asn Leu Leu Glu Lys Leu Glu Leu Ser Arg Ala Asn Ile Leu Tyr
 290                     295                     300

Val Gly Gly His Ala Tyr Leu Leu Leu Ala Asn Thr Asn Lys Thr
 305                     310                     315                     320

Lys Ala Ile Leu Ser Asp Phe Glu His Asp Leu Lys Thr Trp Phe Leu
                 325                     330                     335

Asp Lys Phe Lys Ile Asp Leu Tyr Val Ala Met Ala Tyr Thr Glu Val
             340                     345                     350

Ser Ala Asn Asp Leu Met Asn His Asn Gly His Tyr Arg Asp Ile Tyr
     355                     360                     365

Arg Arg Leu Ser Gln Lys Thr Ser Ala Lys Lys Ala Asn Arg Tyr Thr
 370                     375                     380

Ala Glu Glu Ile Leu Asn Leu Asn His Gln Gly Thr Glu Asn Ala Arg
 385                     390                     395                     400

Glu Cys Arg Glu Cys Lys Arg Ser Asp Leu Leu Ile Glu Glu Asp Asp
                 405                     410                     415

Ile Cys Glu Ile Cys Asp Ser Leu Gln Lys Val Ser Arg Asp Leu Thr
             420                     425                     430

Arg Glu Asn Ile Phe Val Ile Ala Asn Glu Gly Val Leu Asp Met Pro
     435                     440                     445

Phe Gly Lys Lys Met Ser Ala Leu Ser Tyr Ser Gln Ala Asp Lys Leu
 450                     455                     460

Lys Lys Ser Asn Ala Glu Val Gln Ile Tyr Ala Lys Asn Ile Ser Glu
```

```
                    465                 470                 475                 480
Ile Gly Gln Asn Leu Met Thr Arg Ile Asp Met Gly Asp Tyr Thr Tyr
                485                 490                 495

Arg Ser Asp Phe His Glu Met Leu Glu Glu Val Glu Val Gly Ile Asn
                500                 505                 510

Arg Leu Gly Val Leu Arg Ala Asp Val Asp Asn Leu Gly Gln Ala Phe
                515                 520                 525

Ile Asn Gly Ile Pro Asp Asp Tyr Leu Ser Ile Ser Arg Thr Ala Thr
                530                 535                 540

Phe Ser Arg Ala Met Ser Arg Phe Phe Lys Asn Tyr Leu Asn Gln Leu
545                 550                 555                 560

Leu Ala Glu Lys Ser Tyr Lys Ile Asn Val Ile Tyr Ala Gly Gly Asp
                565                 570                 575

Asp Leu Phe Met Ile Gly Ala Trp Gln Asp Ile Leu Asp Phe Ser Ile
                580                 585                 590

Val Leu Lys Gln Lys Phe Ala Asp Phe Thr Gln Asn Lys Leu Ser Ile
                595                 600                 605

Ser Ala Gly Ile Gly Met Phe Arg Glu Lys Tyr Pro Val Ala Arg Met
                610                 615                 620

Ala Ser Leu Thr Gly Asp Leu Glu Asp Ala Ala Lys Asp Tyr Lys Pro
625                 630                 635                 640

Asp Glu Arg Ala Val Gln Ala Thr Lys Asn Ala Val Thr Leu Phe Asp
                645                 650                 655

Ala Thr Asn Val Phe Ser Trp Asp Thr Leu Glu Asn Asp Ile Phe Val
                660                 665                 670

Lys Leu Asp Ala Ile Thr Lys Asn Phe Glu Lys Leu Asp Glu Thr Gly
                675                 680                 685

Lys Ala Phe Ile Tyr Arg Leu Ile Asp Leu Leu Arg Gly Val Asn Glu
                690                 695                 700

Asn Gln Gln Ile Asn Ile Ala Arg Leu Ala Tyr Thr Leu Ser Arg Met
705                 710                 715                 720

Glu Glu Lys Ile Gly Lys Thr Phe Ala Gln Glu Leu Tyr Asn Trp Ala
                725                 730                 735

Asn Ala Asp Arg Lys Thr Leu Ile Met Ala Leu Glu Ile Tyr Ile Leu
                740                 745                 750

Lys Thr Arg Glu Arg
            755

<210> SEQ ID NO 5
<211> LENGTH: 423
<212> TYPE: DNA
<213> ORGANISM: Lactococcus lactis

<400> SEQUENCE: 5
atgactgaat taaaatcgg taatgagaag gtgaactcaa cgaactttgg agattttgcc       60
gaaaaagcaa tcagagggat taatcacaaa ccatttgtta attcaaaagg aggtgagcaa      120
aaaattacga catcaaaaat tcgtggtatt ttagaactgg taaacaaagt ttataatcgt      180
gtcataaata ctaatgatgt tgaactttca gaaatatttt agctgatat tgcgtatatc       240 aaagtaaaaa tcgcttatga atcaggtcgc gaacctgttg tgaaagattt tattcaaaga      300
acagcattta ccgctgcaat tactgatgtg atgaatcaaa gaacccgcga agtttcttg      360 ttattcgcac gttatgttga agtttgatt gcctatttta aatttacgg agggaaagat       420 taa                                                                    423
```

```
<210> SEQ ID NO 6
<211> LENGTH: 140
<212> TYPE: PRT
<213> ORGANISM: Lactococcus lactis

<400> SEQUENCE: 6

Met Thr Glu Leu Lys Ile Gly Asn Glu Lys Val Asn Ser Thr Asn Phe
1               5                   10                  15

Gly Asp Phe Ala Glu Lys Ala Ile Arg Gly Ile Asn His Lys Pro Phe
            20                  25                  30

Val Asn Ser Lys Gly Glu Gln Lys Ile Thr Thr Ser Lys Ile Arg
        35                  40                  45

Gly Ile Leu Glu Leu Val Asn Lys Val Tyr Asn Arg Val Ile Asn Thr
    50                  55                  60

Asn Asp Val Glu Leu Ser Glu Asn Ile Leu Ala Asp Ile Ala Tyr Ile
65                  70                  75                  80

Lys Val Lys Ile Ala Tyr Glu Ser Gly Arg Glu Pro Val Val Lys Asp
                85                  90                  95

Phe Ile Gln Arg Thr Ala Phe Thr Ala Ala Ile Thr Asp Val Met Asn
            100                 105                 110

Gln Arg Thr Arg Glu Ser Phe Leu Leu Phe Ala Arg Tyr Val Glu Ser
        115                 120                 125

Leu Ile Ala Tyr Phe Lys Phe Tyr Gly Gly Lys Asp
    130                 135                 140

<210> SEQ ID NO 7
<211> LENGTH: 645
<212> TYPE: DNA
<213> ORGANISM: Lactococcus lactis

<400> SEQUENCE: 7
atgaaattag taatagaagg aacgattgtt cttaaaacag gtatgcacat tggtggttct      60 agtgatttt cggcgattgg tgcggttgat agcccagtag tccgagatac gctgacacgt      120
ttaccgctca ttccaggaag ttcacttaaa ggtaaaatgc gatatttgct tgcaaaagag     180
ttgaataatg gtattttgtt gaatgaacca ataacgatc aagacgaaat tttgcgactt      240
tttgggtcat cagaaaaaga taagattcgt cgcgctcgtc tgaaattcaa tgatattaag     300
ttatccaatt tggctgaact tgaaactttc aatgtctcat caacagaagt gaagtttgaa     360
aatacgataa atagaaaaac tgctgttgct aatcctcgtc aaattgaacg ggtgattgca     420
ggttcaaaat tcgatttcga atcttctat aatcttgatg atataaagga agttgagaag      480
gactttgaaa atattaaaca gggtttgat ttactagagt ttgactacct aggtggtcat      540
gggacacgtg gtagtggtcg tattgcattt gaaaatttgt cagtcataac agccgttggg     600
aactttgaaa aataaatac tttaaatgaa atcttaggag cttga                      645

<210> SEQ ID NO 8
<211> LENGTH: 214
<212> TYPE: PRT
<213> ORGANISM: Lactococcus lactis

<400> SEQUENCE: 8

Met Lys Leu Val Ile Glu Gly Thr Ile Val Leu Lys Thr Gly Met His
1               5                   10                  15

Ile Gly Gly Ser Ser Asp Phe Ser Ala Ile Gly Ala Val Asp Ser Pro
            20                  25                  30
```

Val Val Arg Asp Thr Leu Thr Arg Leu Pro Leu Ile Pro Gly Ser Ser
     35                   40                  45

Leu Lys Gly Lys Met Arg Tyr Leu Leu Ala Lys Glu Leu Asn Asn Gly
 50                  55                  60

Ile Leu Leu Asn Glu Pro Asn Asn Asp Gln Asp Glu Ile Leu Arg Leu
 65                  70                  75                  80

Phe Gly Ser Ser Glu Lys Asp Lys Ile Arg Arg Ala Arg Leu Lys Phe
                 85                  90                  95

Asn Asp Ile Lys Leu Ser Asn Leu Ala Glu Leu Glu Thr Phe Asn Val
             100                 105                 110

Ser Ser Thr Glu Val Lys Phe Glu Asn Thr Ile Asn Arg Lys Thr Ala
             115                 120                 125

Val Ala Asn Pro Arg Gln Ile Glu Arg Val Ile Ala Gly Ser Lys Phe
 130                 135                 140

Asp Phe Glu Ile Phe Tyr Asn Leu Asp Asp Ile Lys Glu Val Glu Lys
145                 150                 155                 160

Asp Phe Glu Asn Ile Lys Gln Gly Phe Asp Leu Leu Glu Phe Asp Tyr
                 165                 170                 175

Leu Gly Gly His Gly Thr Arg Gly Ser Gly Arg Ile Ala Phe Glu Asn
             180                 185                 190

Leu Ser Val Ile Thr Ala Val Gly Asn Phe Glu Lys Ile Asn Thr Leu
             195                 200                 205

Asn Glu Ile Leu Gly Ala
            210

<210> SEQ ID NO 9
<211> LENGTH: 894
<212> TYPE: DNA
<213> ORGANISM: Lactococcus lactis

<400> SEQUENCE: 9
atgaaaatta tcaaattata ttttgaaagt ccagttcatt ttggtgaaaa gcgcctatcg      60
gagagcaaaa taactttttc ggcagatacc ttatttttcag ctttgatgat cgaggcggtt    120
ggacttggaa agaagatga attttatcaa cttgcttcaa ataatctcgt caaattttca     180
gatgctttcc cttttattga tcaatattac tataccaa accaatgtt caatcttaaa       240 ttggaaaaag aagatgaaaa tccgtctaaa gcttttaaaa aattgctcta tgttccgata    300
gatagtttag aggattattt atcaggtgga ttagatgctt actttgaaag agaaagcttt    360
aatttaggaa aacttgcctt atcggaaaaa gttcaacagc atgatttta ggactctgaa    420 ccttacaatg ttggcacatt taccttcaaa gaaaatacag gtctttatgt cttgatagaa    480
cagactcacc cattattaga ggaattatta gaaaaccttc aatatccagg aataggtggt    540
aaacgaaatt caggctatgg aaaatttaag tttgaaatac tagaggattc agacattgag    600
gacttgtttt cggcaaaagg taatcgaaaa attttacttt ccggtgcctt acccaaagat    660
gcagagcttg aacaagccct aaaaaatgcc tcatatcttt tagaacgtcg aggaggtttt    720
gtccagtctg atacttatgc aacaaatctt gtcaaaaaac aagatctata tgttttcaaa    780
agcggttcaa cattcgaaaa tagctttgac ggagacattt atcaagtagg caaaaaagga   840
aatcatccag tctataaata tgcgaagtca ttttttcttgg aggttagtgt atga         894

<210> SEQ ID NO 10
<211> LENGTH: 297
<212> TYPE: PRT

<213> ORGANISM: Lactococcus lactis

<400> SEQUENCE: 10

```
Met Lys Ile Ile Lys Leu Tyr Phe Glu Ser Pro Val His Phe Gly Glu
1               5                   10                  15
Lys Arg Leu Ser Glu Ser Lys Ile Thr Phe Ser Ala Asp Thr Leu Phe
            20                  25                  30
Ser Ala Leu Met Ile Glu Ala Val Gly Leu Gly Lys Glu Asp Glu Phe
        35                  40                  45
Tyr Gln Leu Ala Ser Asn Asn Leu Val Lys Phe Ser Asp Ala Phe Pro
    50                  55                  60
Phe Ile Asp Gln Tyr Tyr Tyr Ile Pro Lys Pro Met Phe Asn Leu Lys
65                  70                  75                  80
Leu Glu Lys Glu Asp Glu Asn Pro Ser Lys Ala Phe Lys Lys Leu Leu
                85                  90                  95
Tyr Val Pro Ile Asp Ser Leu Glu Asp Tyr Leu Ser Gly Gly Leu Asp
            100                 105                 110
Ala Tyr Phe Glu Arg Glu Ser Phe Asn Leu Gly Lys Leu Ala Leu Ser
        115                 120                 125
Glu Lys Val Gln Gln His Asp Phe Lys Asp Ser Glu Pro Tyr Asn Val
    130                 135                 140
Gly Thr Phe Thr Phe Lys Glu Asn Thr Gly Leu Tyr Val Leu Ile Glu
145                 150                 155                 160
Gln Thr His Pro Leu Leu Glu Leu Leu Glu Asn Leu Gln Tyr Ser
                165                 170                 175
Gly Ile Gly Gly Lys Arg Asn Ser Gly Tyr Gly Lys Phe Lys Phe Glu
            180                 185                 190
Ile Leu Glu Asp Ser Asp Ile Glu Asp Leu Phe Ser Ala Lys Gly Asn
        195                 200                 205
Arg Lys Ile Leu Leu Ser Gly Ala Leu Pro Lys Asp Ala Glu Leu Glu
    210                 215                 220
Gln Ala Leu Lys Asn Ala Ser Tyr Leu Leu Glu Arg Arg Gly Gly Phe
225                 230                 235                 240
Val Gln Ser Asp Thr Tyr Ala Thr Asn Leu Val Lys Lys Gln Asp Leu
                245                 250                 255
Tyr Val Phe Lys Ser Gly Ser Thr Phe Glu Asn Ser Phe Asp Gly Asp
            260                 265                 270
Ile Tyr Gln Val Gly Lys Lys Gly Asn His Pro Val Tyr Lys Tyr Ala
        275                 280                 285
Lys Ser Phe Phe Leu Glu Val Ser Val
    290                 295
```

<210> SEQ ID NO 11
<211> LENGTH: 1062
<212> TYPE: DNA
<213> ORGANISM: Lactococcus lactis

<400> SEQUENCE: 11

```
atgaagaaga catatcgagt gactttaact gcacttggac cgattttat tggcgggggt      60 gagaagctta aaaagtatga gtatatttt gataaacaaa aaaagttgc acatatgatt      120 gatcatacga agtttactaa atacttgtta gaaaaaaatc tattagacga tttcacgagt    180
cgagtcaatt ctcattttga tttatatgat tatttagtca ataaaaaagg aattgttttc    240
atgccattag ttaagtattc agtacctgtt gctcaattta gaacagaggt aaaaaatagg    300
```

```
tttggtaaac ctatttctag ccctccaatg aatgatttga ataccttgt caaagatgct      360 tttggtagac catatattcc aggtagttct ttaaaaggcg ctttacgcac agcgattttg      420
aatgatttaa aggaagatac gaaagaaaat gaagtctttg cccatttaca ggtatcagat      480
agtgaaacca ttgaccttga aaatcttaag gtttatcaaa aagttgatta ttctaaaacg      540
gcaaaaccct tgccgcttta tcgagaatgc ctgaaaccga atactgaaat tacttttaca      600
gtatcttttg atgatgaata tttaacactt aaaaaaattc aaaatgcttt gcataaaacc      660
tatcagcatt attatattaa atggttaaag ggtggaaaag ttggagaaac tttgataaag      720
ggtgtttatg atagtcatgc tgacgagtta aagaaaaata cttttgcatt ggatcaacca      780
agtcaaaatc aaggtgagat catttatatc ggtggcggtg cagggtttgt tagtaagacc      840
ttacattata aatcaaaaaa tcgcgatcaa gctcgtaatg attcttttga tattttaaaa      900
cagctatttc gtacaaccta cagcaagatg cgttcggtac ctgacaatgt cccagttgct      960
ttgaaattgg ctgttgaaac taaaactttt aacgggcgag tgacagggaa acactatctt     1020
gaaatgggga agcaagaat aaaattggag gaattgaaat ga                         1062
```

<210> SEQ ID NO 12
<211> LENGTH: 353
<212> TYPE: PRT
<213> ORGANISM: Lactococcus lactis

<400> SEQUENCE: 12

```
Met Lys Lys Thr Tyr Arg Val Thr Leu Thr Ala Leu Gly Pro Ile Phe
1               5                   10                  15

Ile Gly Gly Gly Glu Lys Leu Lys Tyr Glu Tyr Ile Phe Asp Lys
            20                  25                  30

Gln Lys Lys Val Ala His Met Ile Asp His Thr Lys Phe Thr Lys Tyr
        35                  40                  45

Leu Leu Glu Lys Asn Leu Leu Asp Asp Phe Thr Ser Arg Val Asn Ser
    50                  55                  60

His Phe Asp Leu Tyr Asp Tyr Leu Val Asn Lys Lys Gly Ile Val Phe
65                  70                  75                  80

Met Pro Leu Val Lys Tyr Ser Val Pro Val Ala Gln Phe Arg Thr Glu
                85                  90                  95

Val Lys Asn Arg Phe Gly Lys Pro Ile Ser Ser Pro Met Asn Asp
            100                 105                 110

Leu Asn Thr Phe Val Lys Asp Ala Phe Gly Arg Pro Tyr Ile Pro Gly
        115                 120                 125

Ser Ser Leu Lys Gly Ala Leu Arg Thr Ala Ile Leu Asn Asp Leu Lys
    130                 135                 140

Glu Asp Thr Lys Glu Asn Glu Val Phe Ala His Leu Gln Val Ser Asp
145                 150                 155                 160

Ser Glu Thr Ile Asp Leu Glu Asn Leu Lys Val Tyr Gln Lys Val Asp
                165                 170                 175

Tyr Ser Lys Thr Ala Lys Pro Leu Pro Leu Tyr Arg Glu Cys Leu Lys
            180                 185                 190

Pro Asn Thr Glu Ile Thr Phe Thr Val Ser Phe Asp Asp Glu Tyr Leu
        195                 200                 205

Thr Leu Lys Lys Ile Gln Asn Ala Leu His Lys Thr Tyr Gln His Tyr
    210                 215                 220

Tyr Ile Lys Trp Leu Lys Gly Gly Lys Val Gly Glu Thr Leu Ile Lys
225                 230                 235                 240
```

```
Gly Val Tyr Asp Ser His Ala Asp Glu Leu Lys Lys Asn Thr Phe Ala
                245                 250                 255

Leu Asp Gln Pro Ser Gln Asn Gln Gly Glu Ile Ile Tyr Ile Gly Gly
            260                 265                 270

Gly Ala Gly Phe Val Ser Lys Thr Leu His Tyr Lys Ser Lys Asn Arg
        275                 280                 285

Asp Gln Ala Arg Asn Asp Ser Phe Asp Ile Leu Lys Gln Leu Phe Arg
    290                 295                 300

Thr Thr Tyr Ser Lys Met Arg Ser Val Pro Asp Asn Val Pro Val Ala
305                 310                 315                 320

Leu Lys Leu Ala Val Glu Thr Lys Thr Phe Asn Gly Arg Val Thr Gly
                325                 330                 335

Lys His Tyr Leu Glu Met Gly Lys Ala Arg Ile Lys Leu Glu Glu Leu
            340                 345                 350

Lys

<210> SEQ ID NO 13
<211> LENGTH: 1230
<212> TYPE: DNA
<213> ORGANISM: Lactococcus lactis

<400> SEQUENCE: 13
atgaaaatat tgatttcagc cgtaggagat acagatccta tacgtaattt tcacgatgga      60
ccactgctac atattgtaag agtttatcgt cctgaaaaaa ttgttttagt ccatagtgag     120
agaagtttga ctaagcatga caaacttgtc aaggcattga aaagtatcaa agactattca     180
cctgaaatca ttcaagatgg ggtcgtttta ccagatgcgc aagttgccat ctttgatgag     240
atgtatgata ctgtatcaag tattgttaaa aaatatatat ctgatgatga aattatctta     300
aatatctcca gtgcgacacc gcaaatcatc agtgctatgt ttgcggtgaa tcgtatctct     360
gattttaatg tcacagctgt tcaagttaag acaccgcagc ataagtcaaa cgaagggctg     420
cggcatgata atcaagaaga tattgataaa ttgattgaga cgaatcttga taatcagtct     480
gattatgaga atagaacact tgcagatact ggtatgaaat tttcacaaga tttgacgaaa     540
cgaaatttaa aagctttgat tgataattat gattatcagg gagctttaga acttcttaaa     600
aaacagaaat cattttcaaa tattaaggag ttaagaaaaa aattaacaga gatttcagat     660
acaatcaaaa ttcaaggaat gccagataaa atcgttaaat ctaaattatc caatcaagca     720
aagagtgctt taaattccta tttaaatatt gaccgaaatc acaagcaagg taatattgca     780
gaggtgttga ttcgagtaaa atctcttgta gaatttattt tagaagatta tctaaataat     840
cattttttag atgtcatcac ttacaaagat ggcaaaccat ttttaaatgc ttcaaaatat     900
cctgagattc tgaaaaagtt tcaggaagat gccgaaatga ggggtaagga ataccatagc     960
ggttatttga gcctccctgc ttacattggt attctcaaat ttttcgaacc aaatcatgac    1020
ttattaaaac atatttataa gattcaagaa attaaccaag acagaaataa agtagcgcac    1080
agtctacaag cttttgatag gaaaaatttg aagaaagtat ctagcgcagt ttttgcaagt    1140
aaacaaattc tgttagcttc ttttgacatt gataatcatt ggttctcttt ctatgaggat    1200
ttaaatcagg aaataaaaaa attactatga                                    1230

<210> SEQ ID NO 14
<211> LENGTH: 409
<212> TYPE: PRT
<213> ORGANISM: Lactococcus lactis
```

<400> SEQUENCE: 14

```
Met Lys Ile Leu Ile Ser Ala Val Gly Asp Thr Asp Pro Ile Arg Asn
1               5                   10                  15

Phe His Asp Gly Pro Leu Leu His Ile Val Arg Val Tyr Arg Pro Glu
            20                  25                  30

Lys Ile Val Leu Val His Ser Glu Arg Ser Leu Thr Lys His Asp Lys
        35                  40                  45

Leu Val Lys Ala Leu Lys Ser Ile Lys Asp Tyr Ser Pro Glu Ile Ile
    50                  55                  60

Gln Asp Gly Val Val Leu Pro Asp Ala Gln Val Ala Ile Phe Asp Glu
65                  70                  75                  80

Met Tyr Asp Thr Val Ser Ser Ile Val Lys Lys Tyr Ile Ser Asp Asp
                85                  90                  95

Glu Ile Ile Leu Asn Ile Ser Ser Ala Thr Pro Gln Ile Ile Ser Ala
            100                 105                 110

Met Phe Ala Val Asn Arg Ile Ser Asp Phe Asn Val Thr Ala Val Gln
        115                 120                 125

Val Lys Thr Pro Gln His Lys Ser Asn Glu Gly Leu Arg His Asp Asn
    130                 135                 140

Gln Glu Asp Ile Asp Lys Leu Ile Glu Thr Asn Leu Asp Asn Gln Ser
145                 150                 155                 160

Asp Tyr Glu Asn Arg Thr Leu Ala Asp Thr Gly Met Lys Phe Ser Gln
                165                 170                 175

Asp Leu Thr Lys Arg Asn Leu Lys Ala Leu Ile Asp Asn Tyr Asp Tyr
            180                 185                 190

Gln Gly Ala Leu Glu Leu Leu Lys Gln Lys Ser Phe Ser Asn Ile
        195                 200                 205

Lys Glu Leu Arg Lys Leu Thr Glu Ile Ser Asp Thr Ile Lys Ile
    210                 215                 220

Gln Gly Met Pro Asp Lys Ile Val Lys Ser Lys Leu Ser Asn Gln Ala
225                 230                 235                 240

Lys Ser Ala Leu Asn Ser Tyr Leu Asn Ile Asp Arg Asn His Lys Gln
                245                 250                 255

Gly Asn Ile Ala Glu Val Leu Ile Arg Val Lys Ser Leu Val Glu Phe
            260                 265                 270

Ile Leu Glu Asp Tyr Leu Asn Asn His Phe Leu Asp Val Ile Thr Tyr
        275                 280                 285

Lys Asp Gly Lys Pro Phe Leu Asn Ala Ser Lys Tyr Pro Glu Ile Leu
    290                 295                 300

Lys Lys Phe Gln Glu Asp Ala Glu Met Arg Gly Lys Glu Tyr His Ser
305                 310                 315                 320

Gly Tyr Leu Ser Leu Pro Ala Tyr Ile Gly Ile Leu Lys Phe Phe Glu
                325                 330                 335

Pro Asn His Asp Leu Leu Lys His Ile Tyr Lys Ile Gln Glu Ile Asn
            340                 345                 350

Gln Asp Arg Asn Lys Val Ala His Ser Leu Gln Ala Phe Asp Arg Lys
        355                 360                 365

Asn Leu Lys Lys Val Ser Ser Ala Val Phe Ala Ser Lys Gln Ile Leu
    370                 375                 380

Leu Ala Ser Phe Asp Ile Asp Asn His Trp Phe Ser Phe Tyr Glu Asp
385                 390                 395                 400

Leu Asn Gln Glu Ile Lys Lys Leu Leu
                405
```

<210> SEQ ID NO 15
<211> LENGTH: 747
<212> TYPE: DNA
<213> ORGANISM: Lactococcus lactis

<400> SEQUENCE: 15

```
atgatcgtta aactccgata caaaataaac ctgccaaatt cgcttcgtac ccaaaacatc      60
gggagcactc tccatggtgt tttgatggaa ttattaccca gtgaactggt agagcacctt     120
cataacttaa gctacaatcc atttcgtcag agattaattt ttgaaaaaga gctagtcatt     180
tgggaaattg tgggcttgca caaatggtc tcggaagagc tgttaaaact cgaaaattta     240
agggaaataa caatcaaacg tgcccaaaag actgtttcct tatccttact ctccaaagat     300
gcaatcgcag ttgatgattt ggtgaaaaaa gaaatgggac gcgaaattga cagtcgaatt     360
atctcgctta aatttacaag tccaacctca tttaaagcca atgggcatta tgacattttt     420
ccagatattc gaaaaatttt ccgttcttta atgatgaatt ttgatttttt tagtgaaaca     480
actaaaattt atgattacga ggttttgtcg tacattgaag aaaatgtcca tattgtcagc     540
tataaattga tgacaaagaa ttttcatctc gagaagataa agtaaaagg ttttcaaggt     600
gacatgacgc tcaaagtaac tggcgcagaa cagttcgtaa aattagtctt acttatgatc     660
aaatatgcga ctttcgcagg cattggtatg aaaacaagcc ttggtatggg aggagttttcc     720
atcaatgaga gacattatct acgttga                                         747
```

<210> SEQ ID NO 16
<211> LENGTH: 248
<212> TYPE: PRT
<213> ORGANISM: Lactococcus lactis

<400> SEQUENCE: 16

```
Met Ile Val Lys Leu Arg Tyr Lys Ile Asn Leu Pro Asn Ser Leu Arg
1               5                   10                  15

Thr Gln Asn Ile Gly Ser Thr Leu His Gly Val Leu Met Glu Leu Leu
            20                  25                  30

Pro Ser Glu Leu Val Glu His Leu His Asn Leu Ser Tyr Asn Pro Phe
        35                  40                  45

Arg Gln Arg Leu Ile Phe Glu Lys Glu Leu Val Ile Trp Glu Ile Val
    50                  55                  60

Gly Leu His Lys Met Val Ser Glu Glu Leu Leu Lys Leu Glu Asn Leu
65                  70                  75                  80

Arg Glu Ile Thr Ile Lys Arg Ala Gln Lys Thr Val Ser Leu Ser Leu
                85                  90                  95

Leu Ser Lys Asp Ala Ile Ala Val Asp Asp Leu Val Lys Lys Glu Met
            100                 105                 110

Gly Arg Glu Ile Asp Ser Arg Ile Ile Ser Leu Lys Phe Thr Ser Pro
        115                 120                 125

Thr Ser Phe Lys Ala Asn Gly His Tyr Asp Ile Phe Pro Asp Ile Arg
    130                 135                 140

Lys Ile Phe Arg Ser Leu Met Met Asn Phe Asp Phe Ser Glu Thr
145                 150                 155                 160

Thr Lys Ile Tyr Asp Tyr Glu Val Leu Ser Tyr Ile Glu Glu Asn Val
                165                 170                 175

His Ile Val Ser Tyr Lys Leu Met Thr Lys Asn Phe His Leu Glu Lys
            180                 185                 190
```

```
Ile Lys Val Lys Gly Phe Gln Gly Asp Met Thr Leu Lys Val Thr Gly
            195                 200                 205

Ala Glu Gln Phe Val Lys Leu Val Leu Leu Met Ile Lys Tyr Ala Thr
    210                 215                 220

Phe Ala Gly Ile Gly Met Lys Thr Ser Leu Gly Met Gly Gly Val Ser
225             230                 235                 240

Ile Asn Glu Arg His Tyr Leu Arg
                245
```

<210> SEQ ID NO 17
<211> LENGTH: 756
<212> TYPE: DNA
<213> ORGANISM: Lactococcus lactis

<400> SEQUENCE: 17

```
atgagagaca ttatctacgt tgaaaatagg tattttatca gtagtcgaga aaatgcgctc      60
agatttcatg actatattaa taaagcgacc catttcattg cttttgatga cattgatatt    120
ttagttttgg ataatgcaag aagttacttg tcaaatggtg tgattaacga ctgtttggat    180
cgaaatattt tgattttaac ttgcgataat aaacattctc ctaaagcgat tttaagcaat    240
gcttttgcta ataaaaaacg cttagaacgc ttaagaaatc aattgcaatt atcctctaag    300
tcaaagaatc gtctttggcg taaaattgtg atggcgaaaa ttaataatca ggctgatgct    360
gttaccttca cggttcaaga tggaacagtt catcgagaga taattgaact aggaaaaatg    420
gtcacagaag gagataaaga taatcgcgaa gctgtcgttg cacgaaaata ttttcggaca    480
ttatttggtg gtaattttaa gcgtggtcgt tttgatgatg tcatcaattc agcgctcaat    540
tatggctatg cacttgtgag ggctgtcatc agacgagaat ggctatctg  tggttttgag    600
atgagctttg gtattcatca tatgtcaaca gaaaatcctt ttaatctctc tgatgatatg    660
attgaagttt ttcggccttt tgttgatgtg ttggtatttg agataattgt gacgaactac    720
aagcggaagt tcaaaagggc tatcaaagtt ttttaa                              756
```

<210> SEQ ID NO 18
<211> LENGTH: 251
<212> TYPE: PRT
<213> ORGANISM: Lactococcus lactis

<400> SEQUENCE: 18

```
Met Arg Asp Ile Ile Tyr Val Glu Asn Arg Tyr Phe Ile Ser Ser Arg
1               5                   10                  15

Glu Asn Ala Leu Arg Phe His Asp Tyr Ile Asn Lys Ala Thr His Phe
            20                  25                  30

Ile Ala Phe Asp Asp Ile Asp Ile Leu Val Leu Asp Asn Ala Arg Ser
        35                  40                  45

Tyr Leu Ser Asn Gly Val Ile Asn Asp Cys Leu Asp Arg Asn Ile Leu
    50                  55                  60

Ile Leu Thr Cys Asp Asn Lys His Ser Pro Lys Ala Ile Leu Ser Asn
65                  70                  75                  80

Ala Phe Ala Asn Lys Lys Arg Leu Glu Arg Leu Arg Asn Gln Leu Gln
                85                  90                  95

Leu Ser Ser Lys Ser Lys Asn Arg Leu Trp Arg Lys Ile Val Met Ala
            100                 105                 110

Lys Ile Asn Asn Gln Ala Asp Ala Val Thr Phe Thr Val Gln Asp Gly
        115                 120                 125

Thr Val His Arg Glu Ile Ile Glu Leu Gly Lys Met Val Thr Glu Gly
```

```
                    130                 135                 140
Asp Lys Asp Asn Arg Glu Ala Val Val Ala Arg Lys Tyr Phe Arg Thr
145                 150                 155                 160

Leu Phe Gly Gly Asn Phe Lys Arg Gly Arg Phe Asp Asp Val Ile Asn
                165                 170                 175

Ser Ala Leu Asn Tyr Gly Tyr Ala Leu Val Arg Ala Val Ile Arg Arg
                180                 185                 190

Glu Leu Ala Ile Cys Gly Phe Glu Met Ser Phe Gly Ile His His Met
            195                 200                 205

Ser Thr Glu Asn Pro Phe Asn Leu Ser Asp Asp Met Ile Glu Val Phe
            210                 215                 220

Arg Pro Phe Val Asp Val Leu Val Phe Glu Ile Ile Val Thr Asn Tyr
225                 230                 235                 240

Lys Arg Lys Phe Lys Arg Ala Ile Lys Val Phe
                245                 250

<210> SEQ ID NO 19
<211> LENGTH: 333
<212> TYPE: DNA
<213> ORGANISM: Lactococcus lactis

<400> SEQUENCE: 19
atggcgcatg aatttaaact tgtattctca gaagaatcta aacgttattt aaagaagatt      60
tacgactaca ttgttttaaa tttcttctct gaaatttctg ctcgtagaaa agttgactta     120
cttttgttag gaagtgaagt gttggagaaa attccagaat taggttttga tgttttcaa     180 aagacaggta aaaaatttct gggaatggaa atattcgga ttctagtgat tgaaaaatat     240
ttggcagttt atcagattga ttttgaagaa aacacaatca atattttcg ttttttaaat     300 attaaaacca attatttacg gtacttgaga tag                                  333

<210> SEQ ID NO 20
<211> LENGTH: 110
<212> TYPE: PRT
<213> ORGANISM: Lactococcus lactis

<400> SEQUENCE: 20

Met Ala His Glu Phe Lys Leu Val Phe Ser Glu Glu Ser Lys Arg Tyr
1               5                   10                  15

Leu Lys Lys Ile Tyr Asp Tyr Ile Val Leu Asn Phe Phe Ser Glu Ile
                20                  25                  30

Ser Ala Arg Arg Lys Val Asp Leu Leu Leu Gly Ser Glu Val Leu
            35                  40                  45

Glu Lys Ile Pro Glu Leu Gly Phe Asp Val Phe Gln Lys Thr Gly Lys
        50                  55                  60

Lys Phe Leu Gly Met Glu Asn Ile Arg Ile Leu Val Ile Glu Lys Tyr
65                  70                  75                  80

Leu Ala Val Tyr Gln Ile Asp Phe Glu Glu Asn Thr Ile Asn Ile Phe
                85                  90                  95

Arg Phe Leu Asn Ile Lys Thr Asn Tyr Leu Arg Tyr Leu Arg
                100                 105                 110

<210> SEQ ID NO 21
<211> LENGTH: 150
<212> TYPE: DNA
<213> ORGANISM: Lactococcus lactis

<400> SEQUENCE: 21
```

```
cttttttactt tgattttttgc tatacttaag aaataacaat taaacttttt caatctacct      60
gtaggtcaat ctagcccatt gttttggtcg atatttgacc aagacaatag cgcggaaaag     120
cttactacaa acacgttttt aaagttctct                                      150
```

<210> SEQ ID NO 22
<211> LENGTH: 1114
<212> TYPE: DNA
<213> ORGANISM: Lactococcus lactis

<400> SEQUENCE: 22

```
aaatacaacc gctcctcgat aaaaggggac gagaactgca tgtttatagc cctgccggat      60
tttaagctgc gaaatacaac cgctcctcga taaaagggga cgagaacttt ccattccgtt     120
taactgctgc cagaaagatt tcatcaaata caaccgctcc tcgataaaag gggacgagaa     180
ctggttgttg tcattagctg tatcgtgaat gacgatataa aatacaaccg ctcctcgata     240
aaaggggacg agaacaactt ggaatggtaa ttcatataat ttttcataa aatacaaccg      300 ctcctcgata aaaggggacg agaactgctg gttttatttg ctcaattttt gaattgtcaa     360
aaatacaacc gctcctcgat aaaaggggac gagaactttg ttgtaaaata tttcatgttt     420
tgttttctct tttctaaata caaccgctcc tcgataaaag gggacgagaa cagagagtat     480
tcagtcatga atgaaatgat tgcaatttga aatacaaccg ctcctcgata aaaggggacg     540
agaacacaac tgttttaact ctatcctgat atataaaccc aaatacaacc gctcctcgat     600
aaaaggggac gagaacaact ttttaaggat aagaccaaca gactctgaca aatacaaccg     660
ctcctcgata aaaggggacg agaactttat tgtggcaac aagttcagca ataataggt       720 ttaaatacaa ccgctcctcg ataaaagggg acgagaacga acttagcaag ctattttgtt     780
tcttttcaag agccaaaata caaccgctcc tcgataaaag gggacgagaa catacgttct     840
ttgaaccaag cttcaactcc ctcggaaaat acaaccgctc ctcgataaaa ggggacgaga     900
acttctgtta atttaactcc catttgttag ttctcctaaa tacaaccgct cctcgataaa     960
aggggacgag aactttttaa aatgttgcaa atgtttagct acttcatgaa atacaaccgc    1020
tcctcgataa aaggggacga gaacatatgt cggtttgtct tttggtctaa cgtatgcaaa    1080
atacaaccgc tcctcgataa aaggggacga gaac                                 1114
```

<210> SEQ ID NO 23
<211> LENGTH: 33
<212> TYPE: DNA
<213> ORGANISM: Lactococcus lactis

<400> SEQUENCE: 23

```
catatgattc aggtattgct tctacaccaa gtt                                   33
```

<210> SEQ ID NO 24
<211> LENGTH: 36
<212> TYPE: DNA
<213> ORGANISM: Lactococcus lactis

<400> SEQUENCE: 24

```
aaatacaacc gctcctcgat aaaaggggac gagaac                                36
```

<210> SEQ ID NO 25
<211> LENGTH: 35
<212> TYPE: DNA
<213> ORGANISM: Lactococcus lactis

```
<400> SEQUENCE: 25
tgcatgttta tagccctgcc ggattttaag ctgcg                    35

<210> SEQ ID NO 26
<211> LENGTH: 38
<212> TYPE: DNA
<213> ORGANISM: Lactococcus lactis

<400> SEQUENCE: 26
tttccattcc gtttaactgc tgccagaaag atttcatc                 38

<210> SEQ ID NO 27
<211> LENGTH: 38
<212> TYPE: DNA
<213> ORGANISM: Lactococcus lactis

<400> SEQUENCE: 27
tggttgttgt cattagctgt atcgtgaatg acgatata                 38

<210> SEQ ID NO 28
<211> LENGTH: 34
<212> TYPE: DNA
<213> ORGANISM: Lactococcus lactis

<400> SEQUENCE: 28
aacttggaat ggtaattcat ataatttttt cata                     34

<210> SEQ ID NO 29
<211> LENGTH: 35
<212> TYPE: DNA
<213> ORGANISM: Lactococcus lactis

<400> SEQUENCE: 29
tgctggtttt atttgctcaa ttttgaatt gtcaa                     35

<210> SEQ ID NO 30
<211> LENGTH: 39
<212> TYPE: DNA
<213> ORGANISM: Lactococcus lactis

<400> SEQUENCE: 30
tttgttgtaa aatatttcat gttttgtttt ctcttttct                39

<210> SEQ ID NO 31
<211> LENGTH: 38
<212> TYPE: DNA
<213> ORGANISM: Lactococcus lactis

<400> SEQUENCE: 31
agagagtatt cagtcatgaa tgaaatgatt gcaatttg                 38

<210> SEQ ID NO 32
<211> LENGTH: 35
<212> TYPE: DNA
<213> ORGANISM: Lactococcus lactis

<400> SEQUENCE: 32
acaactgttt taactctatc ctgatatata aaccc                    35

<210> SEQ ID NO 33
<211> LENGTH: 33
<212> TYPE: DNA
<213> ORGANISM: Lactococcus lactis
```

```
<400> SEQUENCE: 33 aacttttaa ggataagacc aacagactct gac                                      33

<210> SEQ ID NO 34
<211> LENGTH: 37
<212> TYPE: DNA
<213> ORGANISM: Lactococcus lactis

<400> SEQUENCE: 34
tttatttgtg gcaacaagtt cagcaataat agggttt                                 37

<210> SEQ ID NO 35
<211> LENGTH: 37
<212> TYPE: DNA
<213> ORGANISM: Lactococcus lactis

<400> SEQUENCE: 35
gaacttagca agctattttg tttcttttca agagcca                                 37

<210> SEQ ID NO 36
<211> LENGTH: 35
<212> TYPE: DNA
<213> ORGANISM: Lactococcus lactis

<400> SEQUENCE: 36
atacgttctt tgaaccaagc ttcaactccc tcgga                                   35

<210> SEQ ID NO 37
<211> LENGTH: 35
<212> TYPE: DNA
<213> ORGANISM: Lactococcus lactis

<400> SEQUENCE: 37
ttctgttaat ttaactccca tttgttagtt ctcct                                   35

<210> SEQ ID NO 38
<211> LENGTH: 35
<212> TYPE: DNA
<213> ORGANISM: Lactococcus lactis

<400> SEQUENCE: 38
tttttaaaat gttgcaaatg tttagctact tcatg                                   35

<210> SEQ ID NO 39
<211> LENGTH: 34
<212> TYPE: DNA
<213> ORGANISM: Lactococcus lactis

<400> SEQUENCE: 39
atatgtcggt ttgtcttttg gtctaacgta tgca                                    34

<210> SEQ ID NO 40
<211> LENGTH: 35
<212> TYPE: DNA
<213> ORGANISM: Lactococcus lactis

<400> SEQUENCE: 40
tcattgacaa ggcgttcaag gtcatcaaaa tcatt                                   35

<210> SEQ ID NO 41
<211> LENGTH: 37
<212> TYPE: DNA
```

<213> ORGANISM: Lactococcus lactis

<400> SEQUENCE: 41
attatcgata tagtatgttt ggttggtgta tttgtca  37

<210> SEQ ID NO 42
<211> LENGTH: 36
<212> TYPE: DNA
<213> ORGANISM: Lactococcus lactis

<400> SEQUENCE: 42
tcagctagtg attcaaaaga tgttatcata cttctt  36

<210> SEQ ID NO 43
<211> LENGTH: 41
<212> TYPE: DNA
<213> ORGANISM: Lactococcus lactis

<400> SEQUENCE: 43
agacaagatg ataatgaaat acgtatggta atttttccac t  41

<210> SEQ ID NO 44
<211> LENGTH: 35
<212> TYPE: DNA
<213> ORGANISM: Lactococcus lactis

<400> SEQUENCE: 44
agcacctgct tcagcccatg tcaagataaa ttctt  35

<210> SEQ ID NO 45
<211> LENGTH: 37
<212> TYPE: DNA
<213> ORGANISM: Lactococcus lactis

<400> SEQUENCE: 45
agtcagggct tatggttttg ttaccaaggg ataaaaa  37

<210> SEQ ID NO 46
<211> LENGTH: 37
<212> TYPE: DNA
<213> ORGANISM: Lactococcus lactis

<400> SEQUENCE: 46
tagagtgcgt agaattttgt tttagacata gtgtttt  37

<210> SEQ ID NO 47
<211> LENGTH: 34
<212> TYPE: DNA
<213> ORGANISM: Lactococcus lactis

<400> SEQUENCE: 47
taatgctcaa cttgcaagta aaccatttta cctt  34

<210> SEQ ID NO 48
<211> LENGTH: 35
<212> TYPE: DNA
<213> ORGANISM: Lactococcus lactis

<400> SEQUENCE: 48
ccaggtgtgc gtggtacatt gatgtttaga gttgc  35

<210> SEQ ID NO 49
<211> LENGTH: 34

<212> TYPE: DNA
<213> ORGANISM: Lactococcus lactis

<400> SEQUENCE: 49
attcccaatt acaaaaatgt agttttcctt tagg                                34

<210> SEQ ID NO 50
<211> LENGTH: 38
<212> TYPE: DNA
<213> ORGANISM: Lactococcus lactis

<400> SEQUENCE: 50
tgtagctctc ttaatgttgt caatttaata ctccctca                            38

<210> SEQ ID NO 51
<211> LENGTH: 38
<212> TYPE: DNA
<213> ORGANISM: Lactococcus lactis

<400> SEQUENCE: 51
tgaacagagg gctttaccat ttaagctata gaaccaaa                            38

<210> SEQ ID NO 52
<211> LENGTH: 36
<212> TYPE: DNA
<213> ORGANISM: Lactococcus lactis

<400> SEQUENCE: 52
cgtttgataa gtggctgaat ctctctaagt cgttgc                              36

<210> SEQ ID NO 53
<211> LENGTH: 38
<212> TYPE: DNA
<213> ORGANISM: Lactococcus lactis

<400> SEQUENCE: 53
acaatagcga agcgttttgc gtgggtttct ttgtttgt                            38

<210> SEQ ID NO 54
<211> LENGTH: 36
<212> TYPE: DNA
<213> ORGANISM: Lactococcus lactis

<400> SEQUENCE: 54
tagacatgag catcaccaga gacccgagcg ttgtca                              36

<210> SEQ ID NO 55
<211> LENGTH: 34
<212> TYPE: DNA
<213> ORGANISM: Lactococcus lactis

<400> SEQUENCE: 55
tatcaaattc ttttgcgctt gtcaagtata aact                                34

<210> SEQ ID NO 56
<211> LENGTH: 37
<212> TYPE: DNA
<213> ORGANISM: Lactococcus lactis

<400> SEQUENCE: 56
tttagtaagt aacgttgtgc atctggcaag attgcat                             37

<210> SEQ ID NO 57

```
<211> LENGTH: 34
<212> TYPE: DNA
<213> ORGANISM: Lactococcus lactis

<400> SEQUENCE: 57
cgtttacrat gttattgtgt tttttattca tttt                              34

<210> SEQ ID NO 58
<211> LENGTH: 36
<212> TYPE: DNA
<213> ORGANISM: Lactococcus lactis

<400> SEQUENCE: 58
ttcaaaacat catcgatgat tttgttttg tctttt                             36

<210> SEQ ID NO 59
<211> LENGTH: 34
<212> TYPE: DNA
<213> ORGANISM: Lactococcus lactis

<400> SEQUENCE: 59
tattttattt atttagcatt ttttcgataa catt                              34

<210> SEQ ID NO 60
<211> LENGTH: 34
<212> TYPE: DNA
<213> ORGANISM: Lactococcus lactis

<400> SEQUENCE: 60
gtaccgtcta acaaattcaa attcggataa atar                              34
```